United States Patent
Kubacki et al.

(10) Patent No.: US 12,396,737 B2
(45) Date of Patent: Aug. 26, 2025

(54) CHAMFER GUIDANCE SYSTEMS AND METHODS

(71) Applicant: WRIGHT MEDICAL TECHNOLOGY, INC., Memphis, TN (US)

(72) Inventors: Meghan Kubacki, Cookeville, TN (US); Braham K. Dhillon, Memphis, TN (US); Kian-Ming Wong, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 422 days.

(21) Appl. No.: 17/758,641

(22) PCT Filed: Apr. 6, 2021

(86) PCT No.: PCT/US2021/025873
§ 371 (c)(1),
(2) Date: Jul. 12, 2022

(87) PCT Pub. No.: WO2021/211323
PCT Pub. Date: Oct. 21, 2021

(65) Prior Publication Data
US 2023/0034361 A1    Feb. 2, 2023

Related U.S. Application Data

(60) Provisional application No. 63/010,895, filed on Apr. 16, 2020.

(51) Int. Cl.
*A61B 17/15* (2006.01)
*A61B 17/16* (2006.01)
(Continued)

(52) U.S. Cl.
CPC .......... *A61B 17/15* (2013.01); *A61B 17/1659* (2013.01); *A61B 17/154* (2013.01);
(Continued)

(58) Field of Classification Search
CPC ..... A61B 17/1775; A61B 17/17; A61B 17/14; A61B 17/16; A61B 17/15; A61B 17/1659;
(Continued)

(56) References Cited

U.S. PATENT DOCUMENTS 3,839,742 A    10/1974   Link
3,872,519 A    3/1975    Giannestras et al.
(Continued)

FOREIGN PATENT DOCUMENTS

CA    2836651      3/2016
CN    101790353    7/2010
(Continued)

OTHER PUBLICATIONS

Extended European Search Report issued in connection with corresponding European Patent Application No. 21788454.3, Mar. 1, 2024, 10 pages.
(Continued)

*Primary Examiner* — Marcela I. Shirsat
(74) *Attorney, Agent, or Firm* — DUANE MORRIS LLP

(57) ABSTRACT

A surgical tool includes a handle and a trial section coupled to the handle by an engagement section. The trial section includes an upper surface and a lower surface. The upper surface has a shape that corresponds to an upper surface of an implant. The trial section defines a first slot extending from the upper surface to the lower surface and inwardly from a first side. A second slot extends from the upper surface to the lower surface and inwardly from a second side.

7 Claims, 71 Drawing Sheets

(51) Int. Cl.
*A61B 17/17* (2006.01)
*A61B 17/56* (2006.01)
*A61B 17/84* (2006.01)
*A61F 2/42* (2006.01)
*A61F 2/46* (2006.01)
*A61F 2/64* (2006.01)

(52) U.S. Cl.
CPC ........... *A61B 17/155* (2013.01); *A61B 17/157* (2013.01); *A61B 17/1662* (2013.01); *A61B 17/1675* (2013.01); *A61B 17/1682* (2013.01); *A61B 17/1728* (2013.01); *A61B 17/1732* (2013.01); *A61B 17/1735* (2013.01); *A61B 17/1739* (2013.01); *A61B 17/1764* (2013.01); *A61B 17/1775* (2016.11); *A61B 2017/564* (2013.01); *A61B 17/848* (2013.01); *A61F 2/4202* (2013.01); *A61F 2/461* (2013.01); *A61F 2/4684* (2013.01); *A61F 2/64* (2013.01)

(58) Field of Classification Search
CPC . A61B 17/1682; A61B 17/848; A61B 17/155; A61B 17/157; A61B 17/154; A61B 17/1662; A61B 17/1675; A61B 17/1728; A61B 17/1732; A61B 17/1735; A61B 17/1739; A61B 17/1764; A61B 2017/564; A61F 2/4684; A61F 2/4202; A61F 2/461; A61F 2/46; A61F 2/42; A61F 2/64
USPC .......................... 623/21.18; 606/86 R, 87, 96
See application file for complete search history.

(56) References Cited

U.S. PATENT DOCUMENTS

| | | |
|---|---|---|
| 3,886,599 A | 6/1975 | Schlein |
| 3,889,300 A | 6/1975 | Smith |
| 3,896,502 A | 7/1975 | Lennox |
| 3,896,503 A | 7/1975 | Freeman et al. |
| 3,975,778 A | 8/1976 | Newton, III |
| 3,987,500 A | 10/1976 | Schlein |
| 4,021,864 A | 5/1977 | Waugh |
| 4,069,518 A | 1/1978 | Groth, Jr. et al. |
| 4,156,944 A | 6/1979 | Schreiber et al. |
| 4,166,292 A | 9/1979 | Bokros |
| 4,204,284 A | 5/1980 | Koeneman |
| 4,232,404 A | 11/1980 | Samuelson et al. |
| 4,309,778 A | 1/1982 | Buechel et al. |
| 4,470,158 A | 9/1984 | Pappas et al. |
| 4,755,185 A | 7/1988 | Tarr |
| 4,968,316 A | 11/1990 | Hergenroeder |
| 5,041,139 A | 8/1991 | Brånemark |
| 5,312,412 A | 5/1994 | Whipple |
| 5,326,365 A | 7/1994 | Alvine |
| 5,354,300 A | 10/1994 | Goble et al. |
| 5,423,825 A | 6/1995 | Levine |
| 5,476,466 A | 12/1995 | Barrette et al. |
| 5,601,563 A | 2/1997 | Burke et al. |
| 5,628,749 A | 5/1997 | Vendrely et al. |
| 5,634,927 A | 6/1997 | Houston et al. |
| 5,667,511 A | 9/1997 | Vendrely et al. |
| 5,674,223 A | 10/1997 | Cipolletti et al. |
| 5,735,904 A | 4/1998 | Pappas |
| 5,766,259 A * | 6/1998 | Sammarco ............. A61B 17/15 623/21.18 |
| 5,776,200 A | 7/1998 | Johnson et al. |
| 5,817,097 A | 10/1998 | Howard et al. |
| 5,824,106 A | 10/1998 | Fournal |
| 5,879,389 A | 3/1999 | Koshino |
| 5,885,299 A | 3/1999 | Winslow et al. |
| 5,888,203 A | 3/1999 | Goldberg |
| 5,897,559 A | 4/1999 | Masini |
| 5,935,132 A | 8/1999 | Bettuchi et al. |
| 6,002,859 A | 12/1999 | DiGioia, III et al. |
| 6,033,405 A | 3/2000 | Winslow et al. |
| 6,102,952 A | 8/2000 | Koshino |
| 6,183,519 B1 | 2/2001 | Bonnin et al. |
| 6,245,109 B1 | 6/2001 | Mendes et al. |
| 6,342,056 B1 | 1/2002 | Mac-Thiong et al. |
| 6,344,043 B1 | 2/2002 | Pappas |
| 6,409,767 B1 | 6/2002 | Pericé et al. |
| 6,436,146 B1 | 8/2002 | Hassler et al. |
| 6,478,800 B1 | 11/2002 | Fraser et al. |
| 6,520,964 B2 | 2/2003 | Tallarida et al. |
| 6,530,930 B1 | 3/2003 | Marino et al. |
| 6,602,259 B1 | 8/2003 | Masini |
| 6,610,067 B2 | 8/2003 | Tallarida et al. |
| 6,610,095 B1 | 8/2003 | Pope et al. |
| 6,620,168 B1 | 9/2003 | Lombardo et al. |
| 6,645,215 B1 | 11/2003 | McGovern et al. |
| 6,663,669 B1 | 12/2003 | Reiley |
| 6,673,116 B2 | 1/2004 | Reiley |
| 6,679,917 B2 | 1/2004 | Ek |
| 6,719,799 B1 | 4/2004 | Kropf |
| 6,824,567 B2 | 11/2004 | Tornier et al. |
| 6,852,130 B2 | 2/2005 | Keller et al. |
| 6,860,902 B2 | 3/2005 | Reiley |
| 6,863,691 B2 | 3/2005 | Short et al. |
| 6,875,222 B2 | 4/2005 | Long et al. |
| 6,875,236 B2 | 4/2005 | Reiley |
| 6,926,739 B1 | 8/2005 | O'Connor et al. |
| 6,939,380 B2 | 9/2005 | Guzman |
| 6,942,670 B2 | 9/2005 | Heldreth et al. |
| 7,001,394 B2 | 2/2006 | Gundlapalli et al. |
| 7,011,687 B2 | 3/2006 | Deffenbaugh et al. |
| 7,025,790 B2 | 4/2006 | Parks et al. |
| 7,163,541 B2 | 1/2007 | Ek |
| 7,238,190 B2 | 7/2007 | Schon et al. |
| 7,252,684 B2 | 8/2007 | Dearnaley |
| 7,314,488 B2 | 1/2008 | Reiley |
| 7,323,012 B1 | 1/2008 | Stone et al. |
| 7,476,227 B2 | 1/2009 | Tornier et al. |
| 7,481,814 B1 | 1/2009 | Metzger |
| 7,485,147 B2 | 2/2009 | Papps et al. |
| 7,534,246 B2 | 5/2009 | Reiley et al. |
| 7,534,270 B2 | 5/2009 | Ball |
| 7,615,082 B2 | 11/2009 | Naegerl et al. |
| 7,618,421 B2 | 11/2009 | Axelson, Jr. et al. |
| 7,625,409 B2 | 12/2009 | Saltzman et al. |
| 7,641,697 B2 | 1/2010 | Reiley |
| 7,678,151 B2 | 3/2010 | Ek |
| 7,713,305 B2 | 5/2010 | Ek |
| 7,717,920 B2 | 5/2010 | Reiley |
| 7,763,080 B2 | 7/2010 | Southworth |
| 7,803,158 B2 | 9/2010 | Hayden |
| 7,850,698 B2 | 12/2010 | Straszheim-Morley et al. |
| 7,896,883 B2 | 3/2011 | Ek et al. |
| 7,896,885 B2 | 3/2011 | Miniaci et al. |
| 7,909,882 B2 | 3/2011 | Stinnette |
| 7,963,996 B2 | 6/2011 | Saltzman et al. |
| 8,002,841 B2 | 8/2011 | Hasselman |
| 8,012,217 B2 | 9/2011 | Strzepa et al. |
| 8,034,114 B2 | 10/2011 | Reiley |
| 8,034,115 B2 | 10/2011 | Reiley |
| 8,048,164 B2 | 11/2011 | Reiley |
| 8,110,006 B2 | 2/2012 | Reiley |
| 8,114,091 B2 | 2/2012 | Ratron et al. |
| 8,167,888 B2 | 5/2012 | Steffensmeier |
| 8,172,850 B2 | 5/2012 | McMinn |
| 8,177,841 B2 | 5/2012 | Ek |
| 8,268,007 B2 | 9/2012 | Barsoum et al. |
| 8,303,667 B2 | 11/2012 | Younger |
| 8,313,492 B2 | 11/2012 | Wong et al. |
| 8,317,797 B2 | 11/2012 | Rasmussen |
| 8,323,346 B2 | 12/2012 | Tepic |
| 8,337,503 B2 | 12/2012 | Lian |
| 8,361,159 B2 | 1/2013 | Ek |
| 8,475,463 B2 | 7/2013 | Lian |
| 8,491,596 B2 | 7/2013 | Long et al. |
| 8,808,303 B2 | 8/2014 | Stemniski et al. |
| 8,911,444 B2 | 12/2014 | Bailey |
| 9,492,281 B2 | 11/2016 | Rouyer et al. |
| 9,907,561 B2 | 3/2018 | Luna et al. |
| 10,034,678 B2 | 7/2018 | Park et al. |

(56) References Cited

U.S. PATENT DOCUMENTS

| | | |
|---|---|---|
| 10,039,558 B2 | 8/2018 | Park et al. |
| 10,149,687 B2 | 12/2018 | McGinley et al. |
| 10,182,832 B1 | 1/2019 | Saltzman et al. |
| 10,206,688 B2 | 2/2019 | Park et al. |
| 10,940,012 B2 | 3/2021 | Sander et al. |
| 2002/0068977 A1 | 6/2002 | Jackson |
| 2002/0082607 A1 | 6/2002 | Heldreth et al. |
| 2002/0133164 A1 | 9/2002 | Williamson |
| 2002/0173853 A1 | 11/2002 | Corl, III et al. |
| 2003/0208280 A1 | 11/2003 | Tohidi |
| 2003/0236522 A1 | 12/2003 | Long et al. |
| 2004/0030399 A1 | 2/2004 | Asencio |
| 2004/0039394 A1 | 2/2004 | Conti et al. |
| 2004/0068322 A1 | 4/2004 | Ferree |
| 2004/0167631 A1 | 8/2004 | Luchesi et al. |
| 2004/0186585 A1 | 9/2004 | Feiwell |
| 2004/0216259 A1 | 11/2004 | Ponziani |
| 2004/0236431 A1 | 11/2004 | Sekel |
| 2005/0004676 A1 | 1/2005 | Schon et al. |
| 2005/0165408 A1 | 7/2005 | Puno et al. |
| 2005/0192674 A1 | 9/2005 | Ferree |
| 2005/0273113 A1 | 12/2005 | Kuczynski |
| 2006/0009857 A1 | 1/2006 | Gibbs et al. |
| 2006/0020345 A1 | 1/2006 | O'Connor et al. |
| 2006/0036257 A1 | 2/2006 | Steffensmeier |
| 2006/0116679 A1 | 6/2006 | Lutz et al. |
| 2006/0142870 A1 | 6/2006 | Robinson et al. |
| 2006/0235541 A1 | 10/2006 | Hodorek |
| 2006/0247788 A1 | 11/2006 | Ross |
| 2007/0038303 A1 | 2/2007 | Myerson et al. |
| 2007/0100346 A1 | 5/2007 | Wyss et al. |
| 2007/0112431 A1 | 5/2007 | Kofoed |
| 2007/0162025 A1 | 7/2007 | Tornier et al. |
| 2007/0173944 A1 | 7/2007 | Keller et al. |
| 2007/0173947 A1 | 7/2007 | Ratron |
| 2007/0213830 A1 | 9/2007 | Ammann et al. |
| 2007/0233129 A1 | 10/2007 | Bertagnoli et al. |
| 2007/0276400 A1 | 11/2007 | Moore et al. |
| 2007/0288030 A1 | 12/2007 | Metzger et al. |
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0312745 A1 | 12/2008 | Keller et al. |
| 2009/0024131 A1 | 1/2009 | Metzger et al. |
| 2009/0043309 A1 | 2/2009 | Rasmussen |
| 2009/0043310 A1 | 2/2009 | Rasmussen |
| 2009/0054992 A1 | 2/2009 | Landes et al. |
| 2009/0082875 A1 | 3/2009 | Long |
| 2009/0088758 A1* | 4/2009 | Bennett .............. A61B 17/155 606/82 |
| 2009/0105767 A1 | 4/2009 | Reiley |
| 2009/0105840 A1 | 4/2009 | Reiley |
| 2009/0182433 A1 | 7/2009 | Reiley et al. |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0212138 A1 | 8/2010 | Carroll et al. |
| 2010/0241237 A1 | 9/2010 | Pappas |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0071645 A1 | 3/2011 | Bojarski et al. |
| 2011/0106268 A1 | 5/2011 | Deffenbaugh et al. |
| 2011/0112542 A1 | 5/2011 | Gross |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0245835 A1 | 10/2011 | Dodd et al. |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053591 A1 | 3/2012 | Haines et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271430 A1 | 10/2012 | Arnett et al. |
| 2012/0277745 A1 | 11/2012 | Lizee |
| 2013/0041473 A1 | 2/2013 | Rouyer et al. |
| 2013/0116797 A1 | 5/2013 | Coulange et al. |
| 2014/0107655 A1* | 4/2014 | Song .................... A61B 17/157 606/88 |
| 2014/0276853 A1* | 9/2014 | Long .................... A61F 2/4202 606/87 |
| 2014/0309640 A1 | 10/2014 | Smith et al. |
| 2015/0045801 A1 | 2/2015 | Axelson et al. |
| 2016/0135815 A1 | 5/2016 | Loring et al. |
| 2018/0177511 A1 | 6/2018 | Luna et al. |
| 2018/0263639 A1 | 9/2018 | McGinley et al. |
| 2019/0059917 A1 | 2/2019 | Saltzman |
| 2019/0059918 A1 | 2/2019 | Saltzman et al. |
| 2019/0133612 A1 | 5/2019 | McGinley et al. |

FOREIGN PATENT DOCUMENTS

| | | |
|---|---|---|
| EP | 2967697 | 4/2018 |
| EP | 3354233 | 10/2019 |
| GB | 2480846 | 12/2011 |
| JP | H11-500035 | 1/1999 |
| JP | 2006150055 | 6/2006 |
| JP | 2007518453 | 7/2007 |
| JP | 2007519477 | 7/2007 |
| JP | 2007536011 | 12/2007 |
| JP | 2011526189 | 10/2011 |
| JP | 2012518517 | 8/2012 |
| JP | 2013500810 | 1/2013 |
| JP | 2013511358 | 4/2013 |
| JP | 2014131738 | 7/2014 |
| WO | WO 9625106 | 8/1996 |
| WO | WO 0166021 A1 | 9/2001 |
| WO | WO 2005011523 A2 | 2/2005 |
| WO | WO 2006022923 | 3/2006 |
| WO | WO 2006023824 | 3/2006 |
| WO | WO 2006099270 | 9/2006 |
| WO | WO 2007084846 | 7/2007 |
| WO | WO 2009158522 | 12/2009 |
| WO | WO 2010099142 | 9/2010 |
| WO | WO 2011015863 | 2/2011 |
| WO | WO 2011063281 | 5/2011 |
| WO | WO 2011151657 | 12/2011 |
| WO | WO 2012088036 | 6/2012 |
| WO | WO 2012116089 | 8/2012 |

(56) References Cited

FOREIGN PATENT DOCUMENTS

| WO | WO 2016039762 | 3/2016 |
|---|---|---|
| WO | 2019091537 A1 | 5/2019 |

OTHER PUBLICATIONS

Search report issued for European patent application No. 13198280 dated Feb. 5, 2014.
International Search Report for International patent application No. PCT/US2014/027448 dated Jul. 7, 2014.
International Preliminary Report on Patentability issued for International patent application No. PCT/US2014/027448, Sep. 15, 2015, 8 pages.
Partial European Search Report issued in connection with European patent application No. 14768333.8, Oct. 26, 2016, 6 pages.
Patent Examination Report No. 1 issued in connection with Australian patent application No. 2015202080, Jul. 5, 2016, 4 pages.
First Office Action issued for Japanese patent application No. 2016-117842, Sep. 12, 2017, 5 pages.
First Office Action issued in connection with corresponding Japanese Patent Application No. 2020-016447, Apr. 6, 2021, 4 pages.
Office Action in corresponding Canadian Patent Application No. 2,904,652, Jun. 2, 2020, 6 pages.
First Examination Report issued in corresponding Australian Patent Application No. 2019213412, Sep. 3, 2020, 5 pages.
First Office Action in corresponding Canadian Patent Application No. 2,904,652, Jan. 28, 2020, 5 pages.
Final Office Action issued in connection with corresponding Japanese Patent Application No. 206-502443, May 15, 2018, 3 pages.
Extended European Search Report issued in connection with corresponding European Patent Application No. 18160378.8, Jun. 29, 2018, 7 pages.
Second Office Action issued in connection with corresponding Chinese Patent Application No. 2018071101785100, dated Jul. 16, 2016, 6 pages.
First Office Action in corresponding Japanese Patent Application No. 2018-178853, Sep. 3, 2018, 3 pages.
Examination Report No. 1 issued in connection with corresponding Australian Patent Application No. 20182000073, Dec. 24, 2018, 3 pages.
First Office Action in corresponding Japanese Patent Application No. 2018-092289, Mar. 5, 2019, 2 pages.
Extended European Search Report and Opinion in connection with European Patent Application No. 14768333.8, dated Jan. 30, 2017, 10 pages.
First Office Action issued in connection with Chinese Patent Application No. 2017800899442 dated Apr. 6, 2022, 8 pages.
International Search Report and Written Opinion issued in connection with International Patent Application No. PCT/US2021/025873, Sep. 2, 2021.

\* cited by examiner

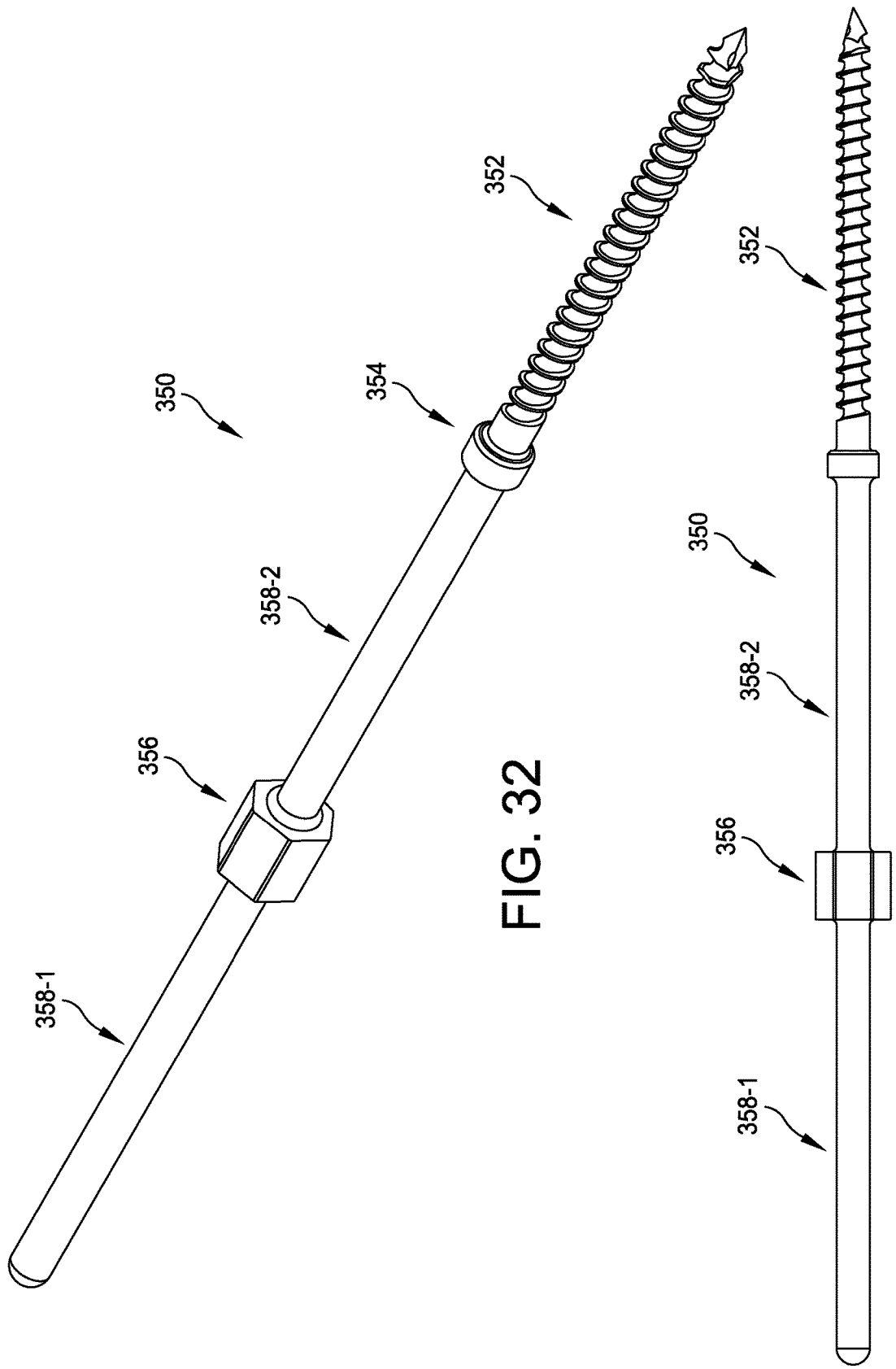

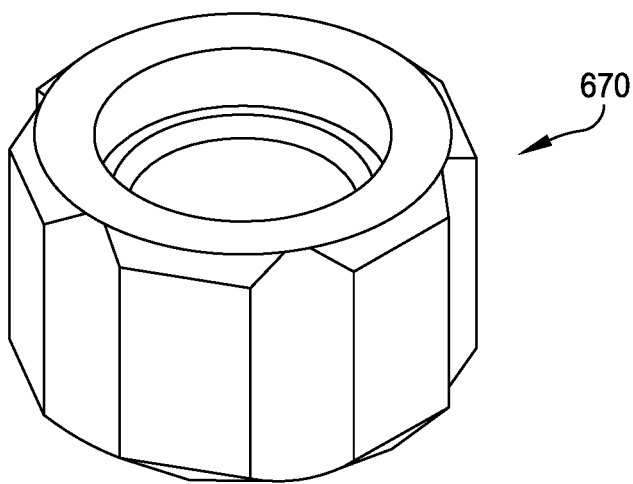
FIG. 68
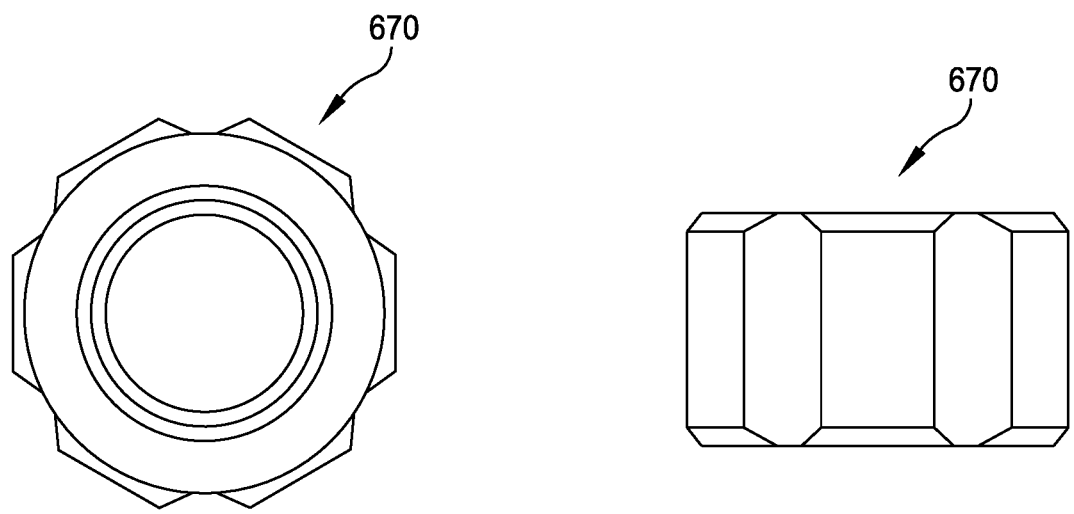
FIG. 69
FIG. 70

CHAMFER GUIDANCE SYSTEMS AND METHODS

CROSS-REFERENCE TO RELATED APPLICATIONS

This application is a National Stage Application, filed under 35 U.S.C. 371, of International Patent Application No. PCT/US2021/025873, filed on Apr. 6, 2021, which claims priority to U.S. Provisional Patent Application No. 63/010,895, filed on Apr. 16, 2020, the entire contents of which are incorporated herein by reference.

INCORPORATION BY REFERENCE

This application also incorporates by reference in its entirety U.S. Pat. No. 9,907,561, entitled "Ankle Replacement System and Method," which issued from U.S. patent application Ser. No. 14/446,921 on Mar. 6, 2018.

FIELD OF DISCLOSURE

The disclosure relates to surgical devices and methods. More specifically, the disclosure relates to system and methods for total ankle replacement.

BACKGROUND

U.S. Pat. No. 9,907,561 (the "'561 Patent"), which patent has been incorporated by reference in its entirety as set forth above, discloses various tools for performing total ankle arthroplasty. The procedure for preparing the talus in the '561 Patent requires numerous steps and surgical tools. Accordingly, systems and methods for talus preparation using fewer components or steps would be beneficial, as it would reduce the length of the surgeries and manufacturing costs.

SUMMARY

In some embodiments, a surgical tool includes a handle and a trial section coupled to the handle by an engagement section. The trial section includes an upper surface and a lower surface. The upper surface has a shape that corresponds to an upper surface of an implant. The trial section defines a first slot extending from the upper surface to the lower surface and inwardly from a first side. A second slot extends from the upper surface to the lower surface and inwardly from a second side.

A tool includes a base component and arm component. The base component has a first surface for engaging a bone, a second surface disposed on an opposite side of the base component with respect to the first surface, and a third surface extending between the first surface and the second surface. The first surface defines a first slot that extends inwardly from a first side of the base component to a second side of the base component. The base component defines a second slot extending inwardly from the third surface and being in communication with the first slot, and the second surface defining a passageway. The arm component has a base from which a peg extends. The peg is size and configured to be at least partially received within the passageway defined by the base component for coupling the arm component to the base component. The arm component defines an opening sized and configured to receive a first cutting tool therein.

In some embodiments, a tool includes a body extending from a first end to a second end. The body includes a first surface disposed adjacent to the first end that is adapted to contact a bone. The surface defines a first slot extending from a first side of the body to a second side of the body. The body includes an extension having a second surface disposed at the second end. The extension defines a second slot sized and configured to receive a cutting tool therein. The second slot has a longitudinal axis that extends in a widthwise direction across the body. The body defines a third slot along a length of the body between the first end and the second end, and the third slot extending through the body such that the third slot is in communication with the first slot.

In some embodiments, a tool includes a base component and a guide component for coupling to the base component. The base component defines a slot, a first pair of holes located on a first side of the slot, and a second pair of holes located on a second side of the slot. The guide component includes a pair of pegs extending from a first surface. The pair of pegs sized and arranged to be received in the first pair of holes and the second pair of holes of the base component. The guide component defines a first slot and a second slot that extend parallel to one another. The first slot defined by the guide is aligned with the slot defined by the base component when the pair of pegs are received within the first pair of holes, and the second slot defined by the guide is aligned with the slot defined by the base component when the pair of pegs are received within the second pair of holes.

In some embodiments, a tool includes a base component and an arm component for coupling to the base component. The base component extends from a first end to a second end and defines at least one hole adjacent to the first end and including a beam disposed at the second end. The beam includes at least one projection extending along its length. The arm component includes a coupling end defining a recess for receiving at least a portion of the beam and the at least one projection to couple the arm component to the base component. The arm component defines at least one hole sized and configured to receive a cutting tool therethrough.

In some embodiments, a tool includes locator guide. The locator guide extends from a first end to a second end and defines at least one hole sized and configured to receive a fixation element. The locator guide contains features that interact with mating features of a cutting guide.

BRIEF DESCRIPTION OF THE DRAWINGS

FIG. 32 is an isometric view of one example of a fixation element in accordance with some embodiments;

FIG. 33 is a side view of the fixation element illustrated in FIG. 32 in accordance with some embodiments;

FIG. 68 is an isometric view of one example of a nut in accordance with some embodiments;

FIG. 69 is a top side plan view of the nut illustrated in FIG. 68 in accordance with some embodiments;

FIG. 70 is a side view of the nut illustrated in FIG. 68 in accordance with some embodiments;

FIG. 121 is an isometric view of a base component in accordance with some embodiments;

FIG. 122 is a top side view of the base component illustrated in FIG. 121 in accordance with some embodiments;

FIG. 123 is a bottom side view of the base component illustrated in FIG. 121 in accordance with some embodiments;

FIG. 124 is a rear side view of the base component illustrated in FIG. 121 in accordance with some embodiments;

FIG. 125 is a front side view of the base component illustrated in FIG. 121 in accordance with some embodiments;

FIG. 126 is a side view of the base component illustrated in FIG. 121 in accordance with some embodiments;

FIG. 127 is an isometric view of a cutting guide that may be coupled to the base component illustrated in FIGS. 121-126 in accordance with some embodiments;

FIG. 128 is a front side view of the cutting guide illustrated in FIG. 127 in accordance with some embodiments;

FIG. 129 is a rear side view of the cutting guide illustrated in FIG. 127 in accordance with some embodiments;

FIG. 130 is a top side view of the cutting guide illustrated in FIG. 127 in accordance with some embodiments;

FIG. 131 is a bottom side view of the cutting guide illustrated in FIG. 127 in accordance with some embodiments; and FIGS. 132 and 133 are opposing side views of the cutting guide illustrated in FIG. 126 in accordance with some embodiments.

DETAILED DESCRIPTION

This description of the exemplary embodiments is intended to be read in connection with the accompanying drawings, which are to be considered part of the entire written description.

The inventors have identified certain improvements to various components disclosed in the '561 Patent that advantageously enables the procedures to be performed using fewer components, which also enables the procedures to be performed faster. Although the disclosed systems and methods are described in connection with the systems and methods disclosed in the '561 Patent, a person of ordinary skill in the art will understand that the disclosure is not so limited as the disclosed systems and methods may be used in a variety of different surgical procedures and with other systems or components.

Multi-Purpose Talar Dome Trial

FIGS. 1-5 illustrate one example of an improved multi-purpose talar dome trial in accordance with some embodiments. As described below, in addition to being used as a trial, trial 100 may also be used as a cutting guide for making bony cuts, including chamfer cuts to the talus.

Figure 1:
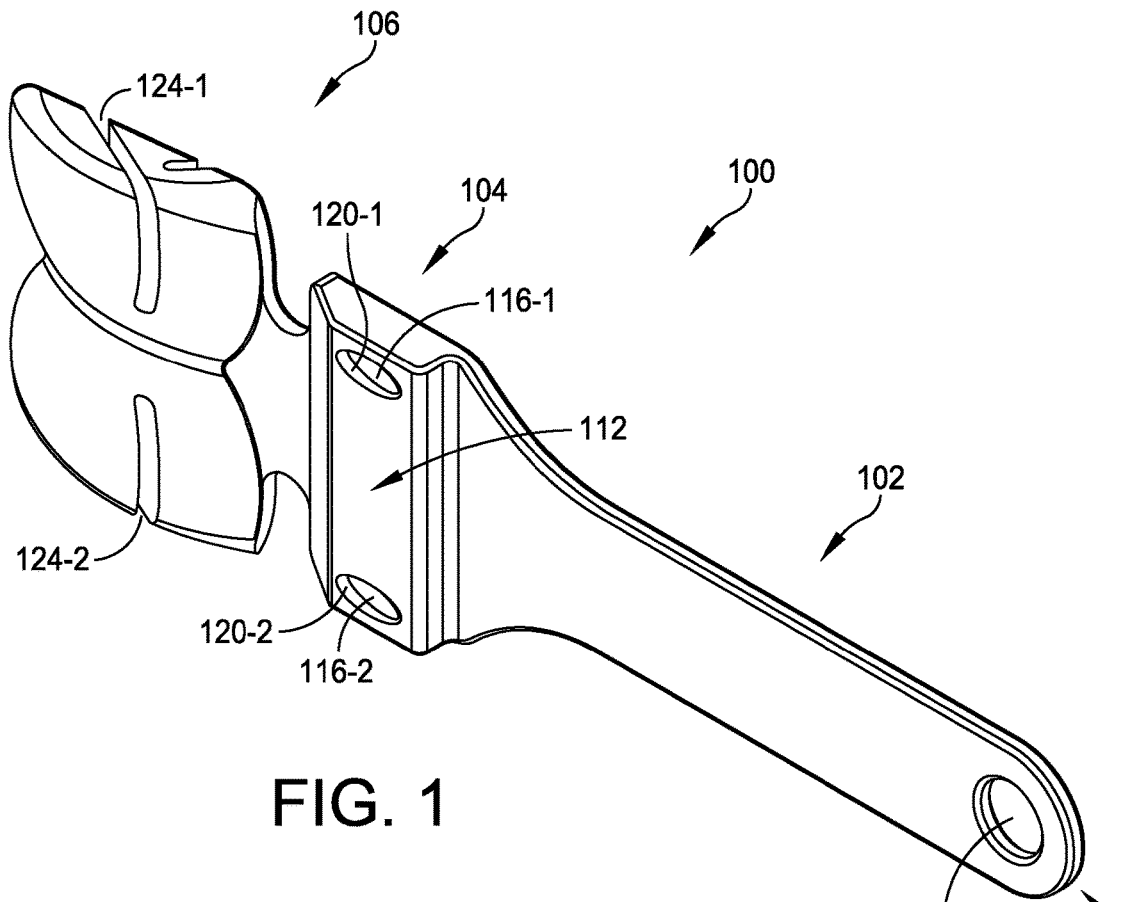
FIG. 1 is an isometric view of one example of a multi-purpose tool in accordance with some embodiments.
Figure 2:
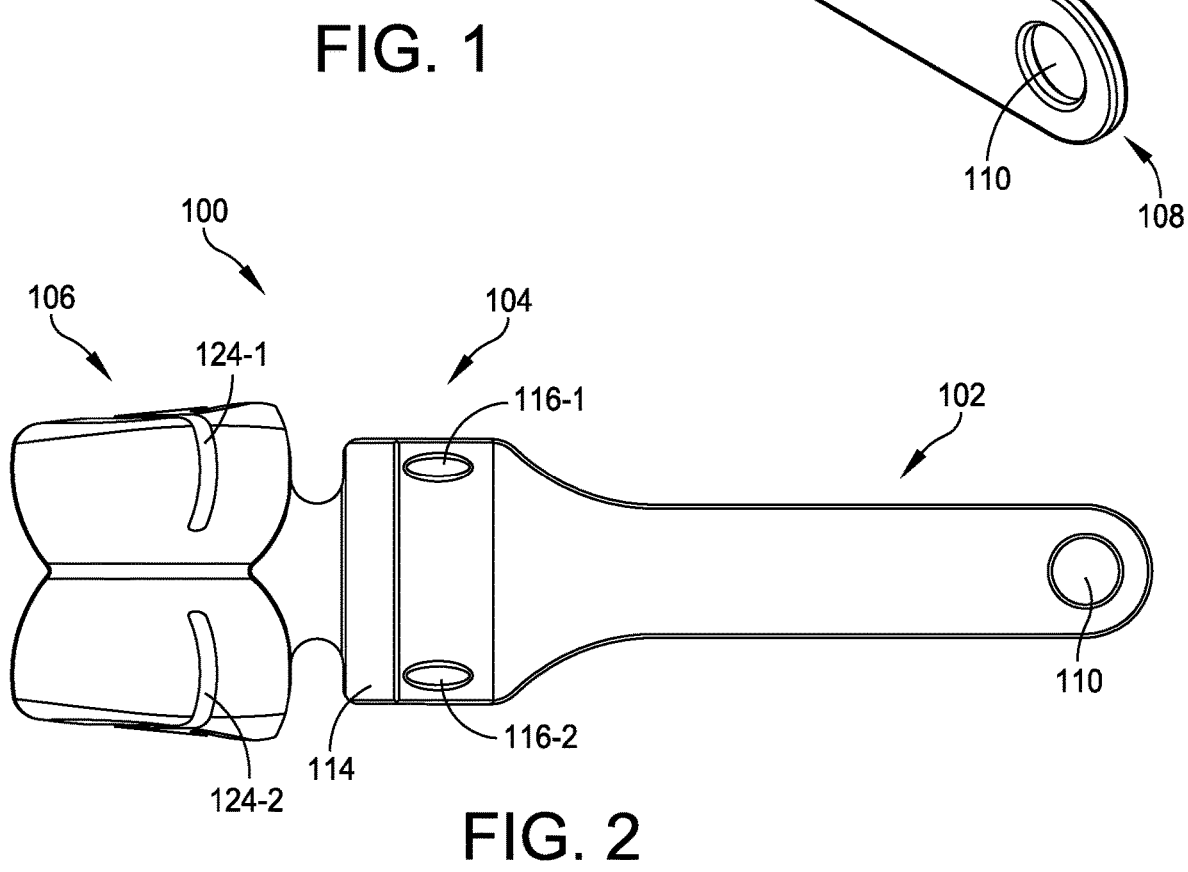
FIG. 2 is a top side plan view of the multi-purpose tool illustrated in FIG. 1 in accordance with some embodiments.

The talar dome trial 100 illustrated in FIG. 1 includes a handle section 102, an engagement section 104, and a trial section 106. In some embodiments, handle section 102 has an elongate shape extending from a first end 108 of the trial 100 to the engagement section 104. As best seen in FIGS. 1 and 2, handle section 102 may define a hole 110 adjacent to first end 108 of trial 100.

Figure 4:
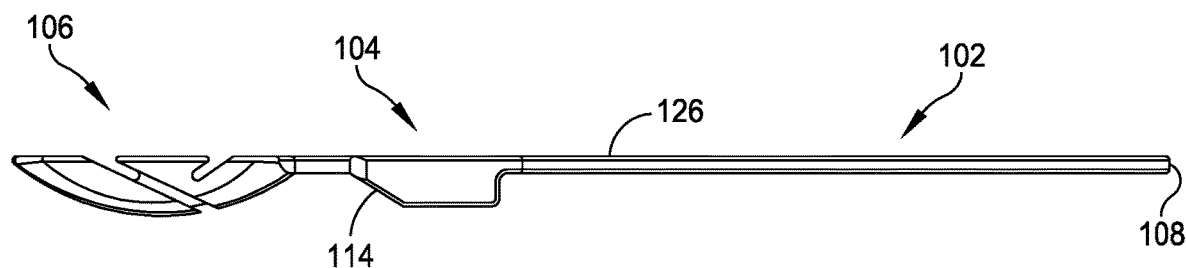
FIG. 4 is a side view of the multi-purpose tool illustrated in FIG. 1 in accordance with some embodiments.
Figure 5:
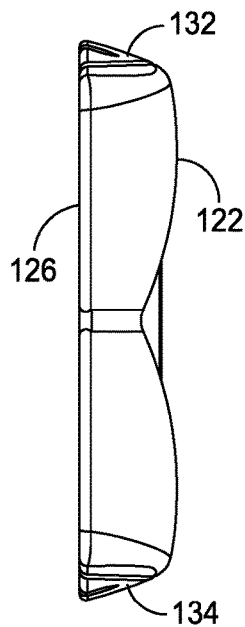
FIG. 5 is an end view of the multi-purpose tool illustrated in FIG. 1 in accordance with some embodiments.

In some embodiments, engagement section 104 includes a body 112 having a thickness that is greater than a thickness of the handle section 102 as best seen in FIG. 4. However, one of ordinary skill in the art will understand that the thickness of handle section 102 may be varied such that the thickness of engagement section 104 may be equal to or less than the thickness of handle section 102. Body 112 may have a generally rectangular shape with a sloped leading side 114, as best seen in FIGS. 1 and 4, and define a pair of spaced apart holes 116-1, 116-2 (collectively, "holes 116"). In some embodiments, holes 116 extend through the entirety of body 112 and may have central axes that are parallel to a plane defined by side 114 of body 112.

Trial section 106 has at least one convex upper surface 122 that corresponds to the size and shape of a prosthetic talar dome of an ankle replacement system. As best seen in FIGS. 1-2, a pair of spaced apart slots 124-1, 124-2 (collectively, "slots 124") are defined by the trial section 106 such that the slots 124 extend from the upper surface 122 to the bottom surface 126. In some embodiments, the angle at which the slots extend at an angle through trial section 106 is parallel to an angle at which the holes 116 extend through engagement section 104.

Figure 3:
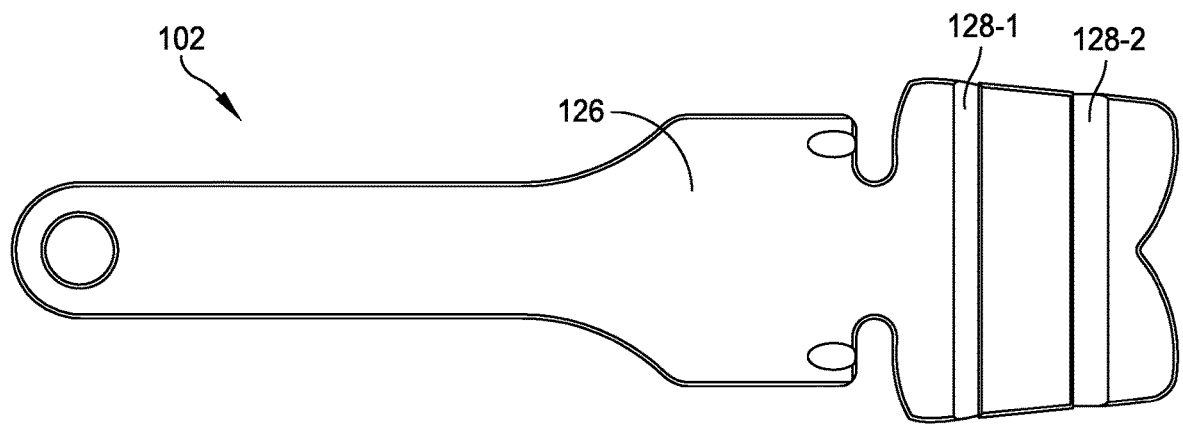
FIG. 3 is a bottom side plan view of the multi-purpose tool illustrated in FIG. 1 in accordance with some embodiments.

As best seen in FIG. 3, trial section 106 further defines a pair of angle slots 128-1, 128-2 (collectively, "slots 128") that inwardly extend from the bottom surface 126 of trial 100 from a first side 132 (e.g., a lateral side) to a second side (e.g., a medial side) 134. A portion of slots 128 are aligned and communicate with slots 124 as best seen in FIG. 3. As described in greater detail below, slots 128 may be used to by a surgeon or other practitioner as a visual indicator under fluoroscopy for checking where the posterior chamfer cut will be made.

In use, the multi-purpose trial 100 may be inserted into a resected joint space formed between the inferior portion of a tibia and the superior portion of the talus. The trial 100 may be inserted into the resected joint space along with a poly trial insert, such as poly trial insert 230 disclosed in the '561 Patent. The location of the trial 100 may be checked using sagittal plane fluoroscopy to confirm that the posterior portion of the trial section 106 of trial 100 rests on the posterior portion of the talus (e.g., to establish congruence between the talus and the implant). Slots 128, which are visible under fluoroscopy, also may be used to visualize to location at which the posterior chamfer cuts will be made (i.e., extending along an axis defined by the slots 128).

When the desired positioning of trial 100 is achieved, the trial 100 may be secured to the talus by inserting one or more pins, k-wires, or other fixation elements through holes 116. Other instruments, such as a poly insert, may be removed from the resected joint space leaving behind the trial 100. Posterior chamfer cuts may then be made using the trial 100 as a cutting guide. For example, with trial 100 secured to the talus, a surgeon or other practitioner may make bony cuts using a bone saw by inserting the bone saw into slots 124, 128. Advantageously, the trial 100 enables saw cuts to be made through the medial and lateral edges of the talus. Once the talar cut has been made, the trial 100 may be removed from its engagement leaving the pins within the talus.

Anterior/Posterior Resection Guide

FIGS. 6-21 illustrate one example of a chamfer guide 200 in accordance with some embodiments. Chamfer guide 200 includes a base component 202 that supports an arm component 240. The body 204 of base component 202 includes a first leg 206 and a second leg 208 that extends away from first leg 206 at an angle. Leg 206 includes a planar bottom surface 210 that defines a slot 212, which extends from a first side 214 to a second side 216.

Figure 7:
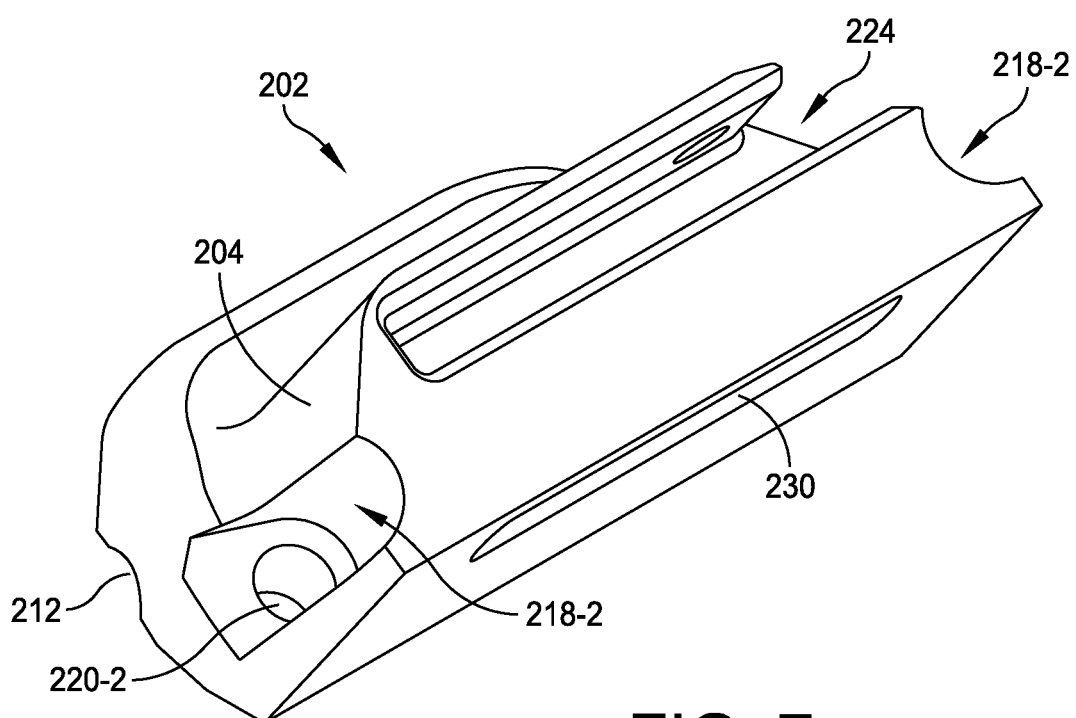
FIG. 7 is an isometric view of a base component of the resection guide illustrated in FIG. 6 in accordance with some embodiments.
Figure 8:
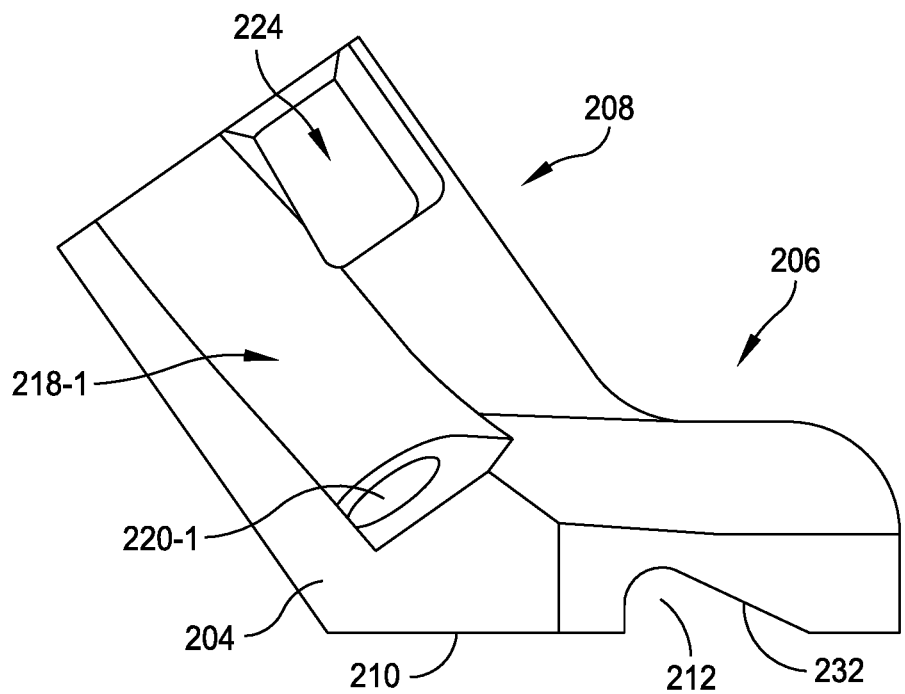
FIG. 8 is a side view of the base component illustrated in FIG. 7 in accordance with some embodiments.
Figure 9:
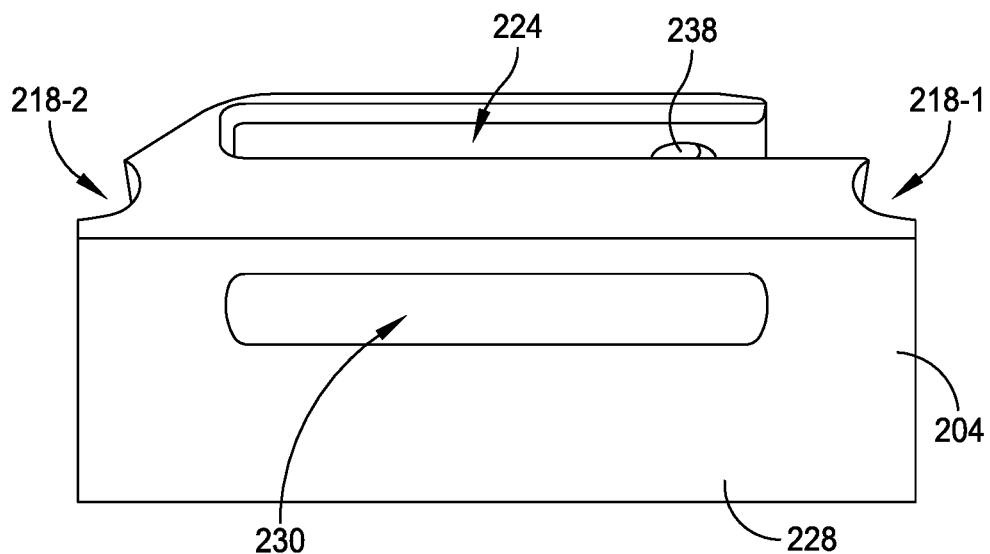
FIG. 9 is a rear side view of the base component illustrated in FIG. 7 in accordance with some embodiments.
Figure 10:
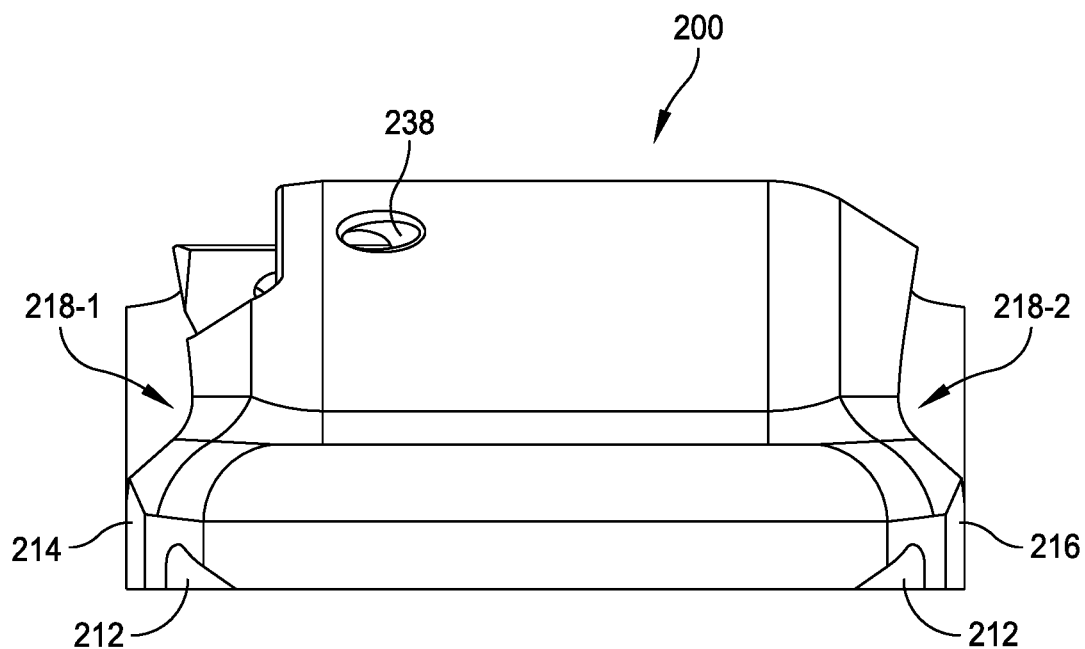
FIG. 10 is a front side view of the base component illustrated in FIG. 7 in accordance with some embodiments.
Figure 11:
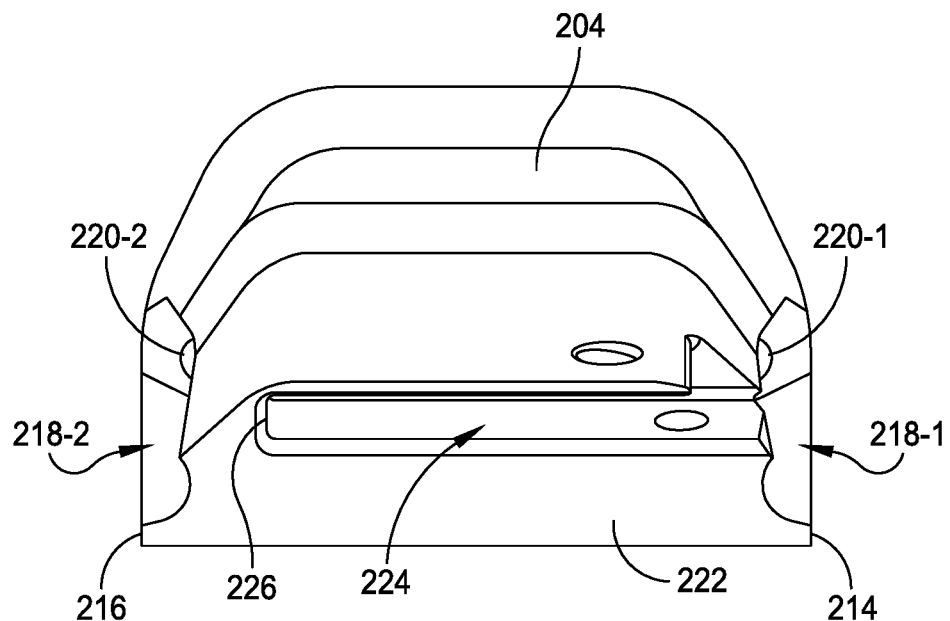
FIG. 11 is a top side view of the base component illustrated in FIG. 7 in accordance with some embodiments.
Figure 12:
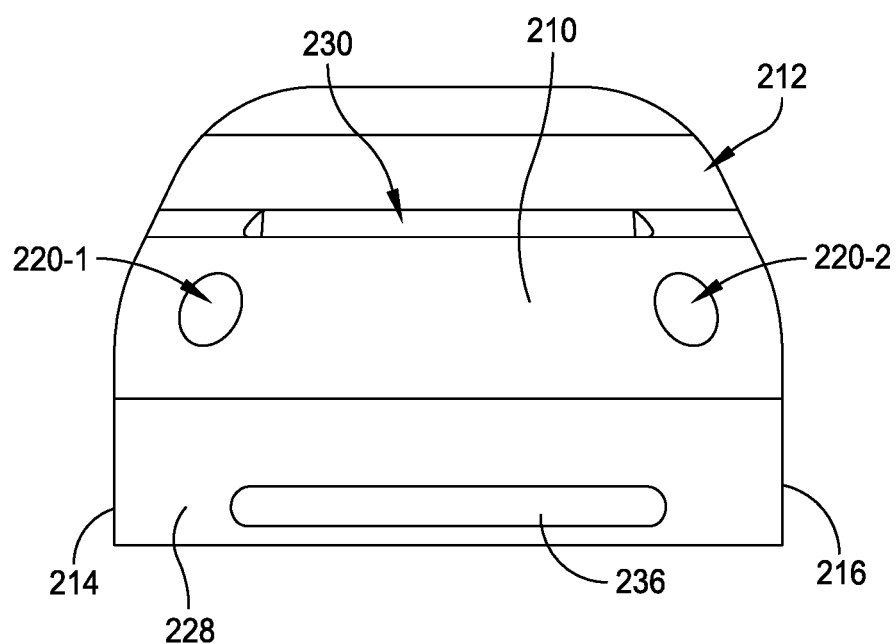
FIG. 12 is a bottom side view of the base component illustrated in FIG. 7 in accordance with some embodiments.
Figure 13:
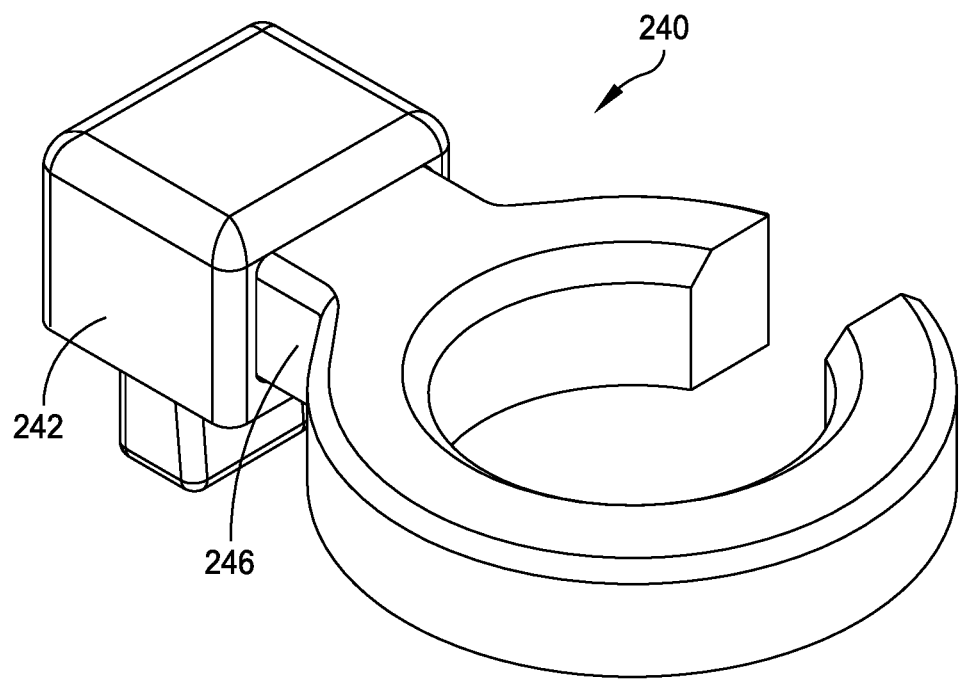
FIG. 13 is an isometric view of the arm component of the resection guide illustrated in FIG. 6 in accordance with some embodiments.

As best seen in FIGS. 7, 9, and 11, body 204 defines a pair of spaced apart recesses 218-1, 218-2 (collectively, "recesses 218") each defining a respective hole 220-1, 220-2 (collectively, "holes 220"). Holes 220 extend through body 204, extending through bottom surface 210, and being sized and configured to receive a pin, k-wire, or other fixation element therein. In some embodiments, holes 220 extend through body 204 parallel to one another; however, one of ordinary skill in the art will understand that holes 220 may extend through body such that they are not disposed parallel to one another. Leg 208 includes a planar upper surface 222 defining a passageway 224. As best seen in FIG. 11, in some embodiments, passageway 224 extends from side 214 across body 204 terminating at end wall 226. Rear surface 228 defines a slot 230 that extends at an angle through body 204 to bottom surface 210 where it intersects with slot 212 as best seen in FIG. 12. Slot 230 is sized and configured to receive a cutting instrument, such as a saw, therein. In some embodiments, as described below, slot 230 is used as a cutting guide for performing a posterior chamfer cut on a bone, such as a talus. A person of ordinary skill in the art will understand that slot 230 may be used for performing other cuts.

Turning now to FIGS. 13-19, arm component 240 includes a base 242 from which a peg 244 and an arm 246 extend. Peg 244 extends from surface 248 of base 242 and is sized and configured to be received within passageway 224 defined by body 204 of base component 202. In some embodiments, peg 244 may be received within passageway 224 such that peg 224 can be slid along the length of passageway 224. Although not shown, one of ordinary skill in the art will understand that peg 224 may include a dovetail or other coupling configuration to mate with a complementary configuration provided by passageway 224 to prevent peg 224 from being easily disengaged from passageway 224.

Figure 14:
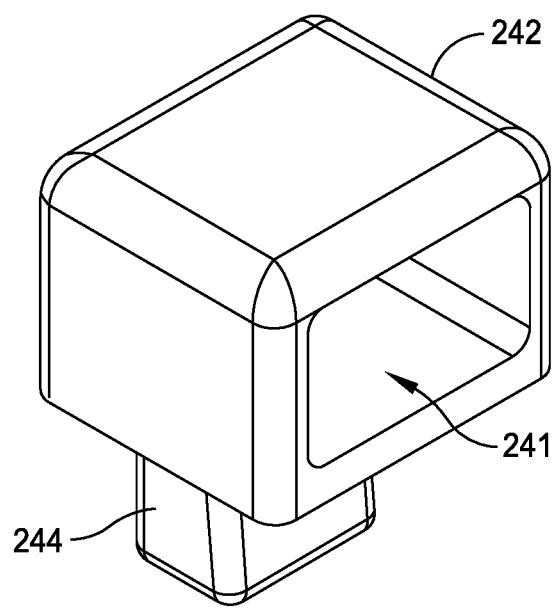
FIG. 14 is an isometric view of a base of the arm component illustrated in FIG. 13 in accordance with some embodiments.
Figure 15:
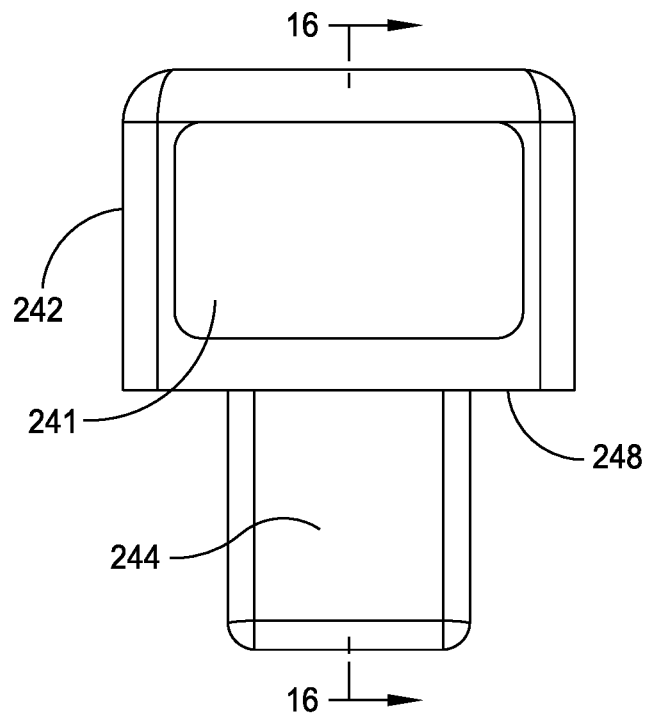
FIG. 15 is a front side view of the base illustrated in FIG. 14 in accordance with some embodiments.
Figure 16:
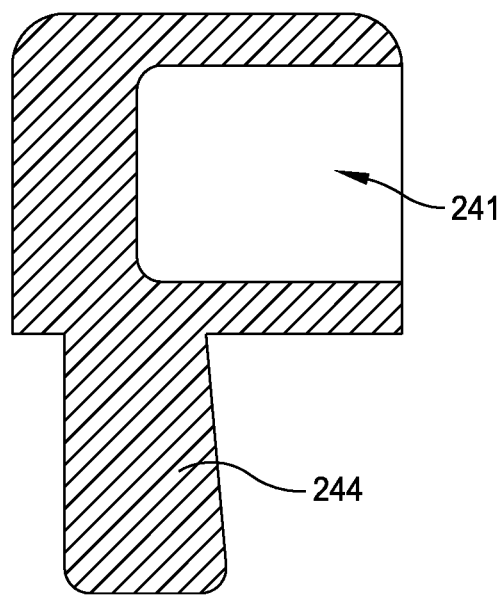
FIG. 16 is a section view of the base taken along line 16-16 in FIG. 15 in accordance with some embodiments.

In some embodiments, the base 242 and arm 246 may be formed separately and joined together to form arm component 240. In such embodiments, baes 242 may define a cavity 241, as illustrated in FIGS. 14-16, sized and configured to receive at least a portion of arm 246. However, one of ordinary skill in the art will understand that arm component 240 may be a monolith in some embodiments.

Figure 6:
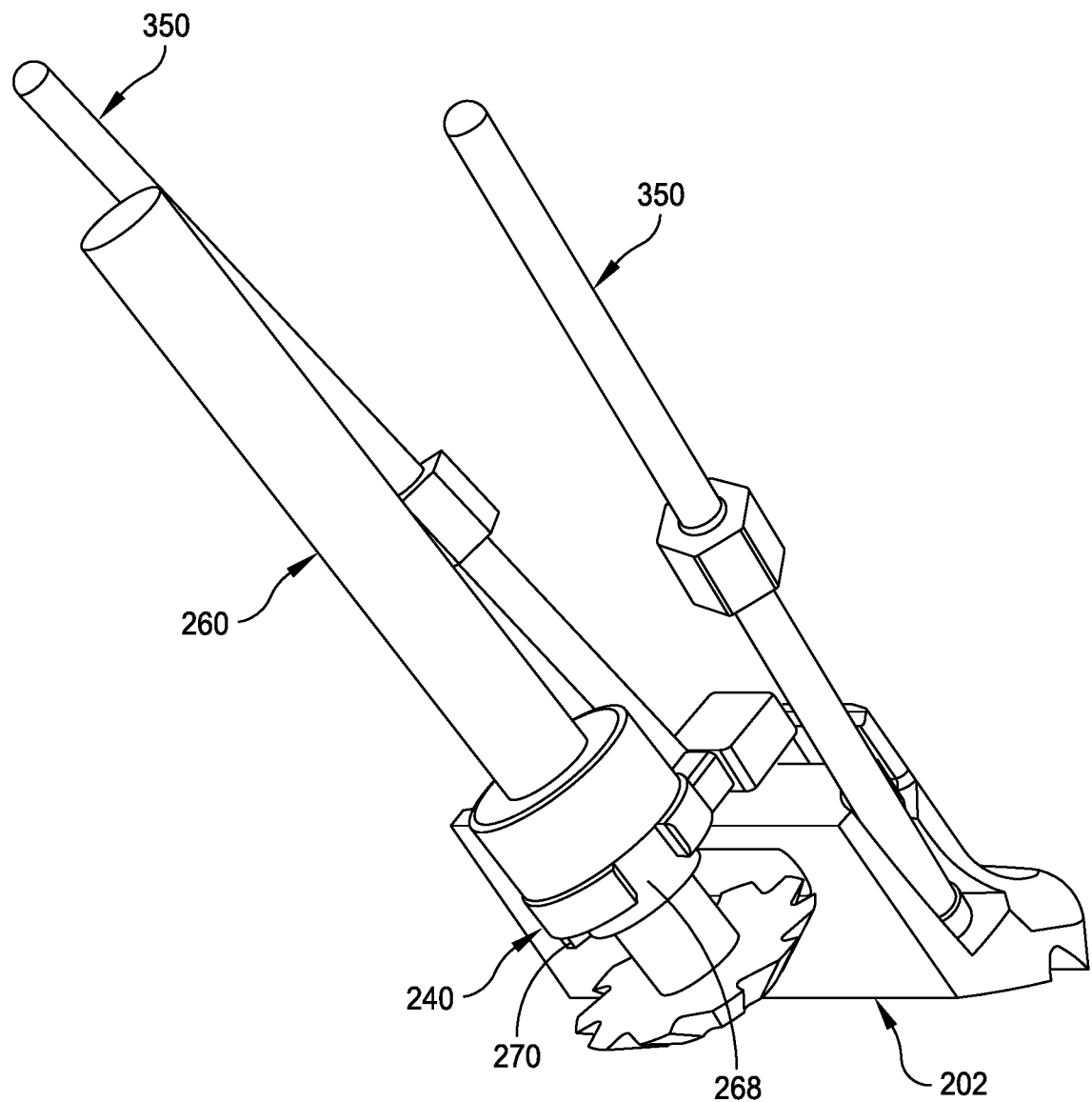
FIG. 6 is an isometric view of one example of a resection guide in accordance with some embodiments.
Figure 17:
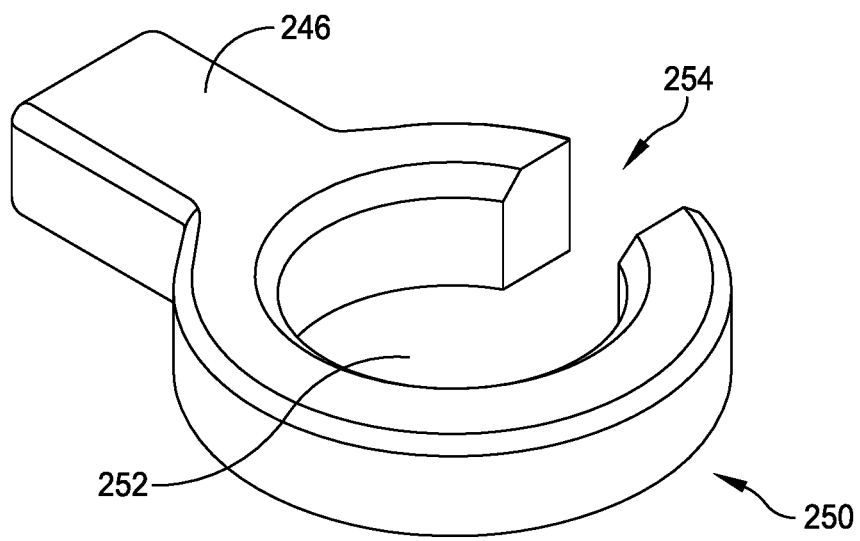
FIG. 17 is an isometric view of an arm of the arm component illustrated in FIG. 13 in accordance with some embodiments.
Figure 18:
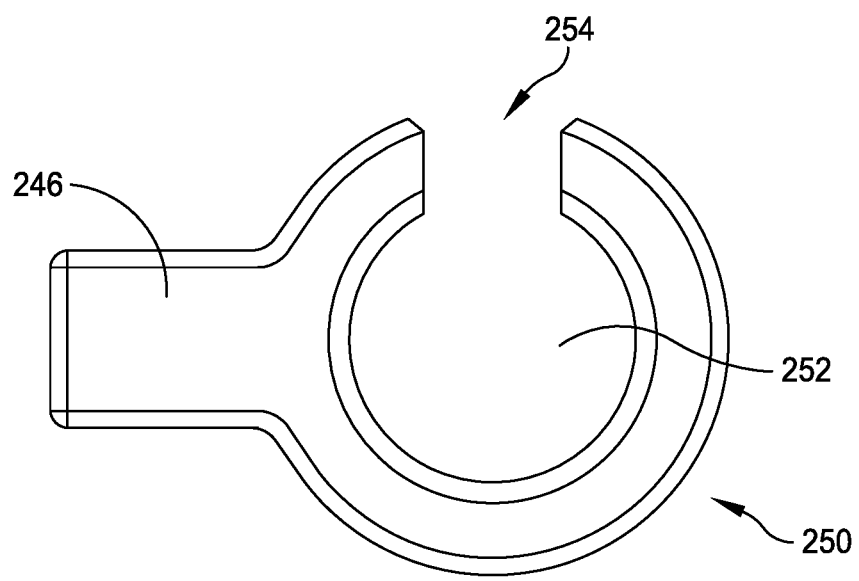
FIG. 18 is a top side view of the arm illustrated in FIG. 17 in accordance with some embodiments.
Figure 19:
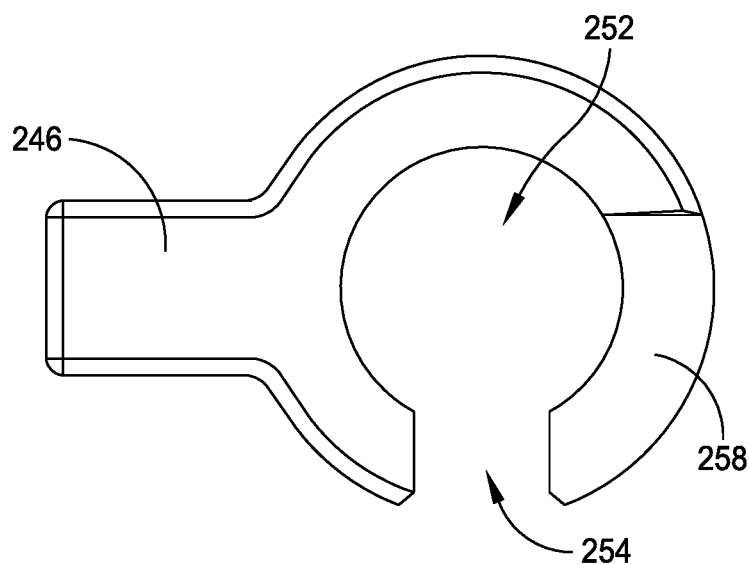
FIG. 19 is a bottom side view of the arm illustrated in FIG. 17 in accordance with some embodiments.
Figure 20:
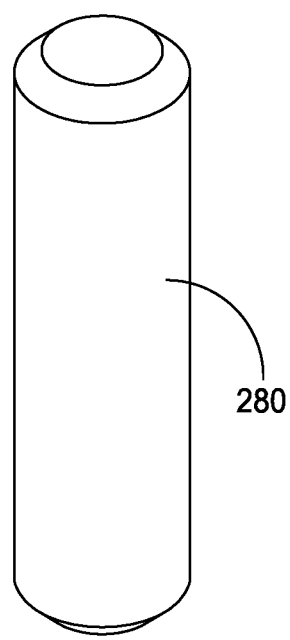
FIG. 20 is an isometric view of one example of a dowel that may be used in connection with the resection guide illustrated in FIG. 6 in accordance with some embodiments.
Figure 21:
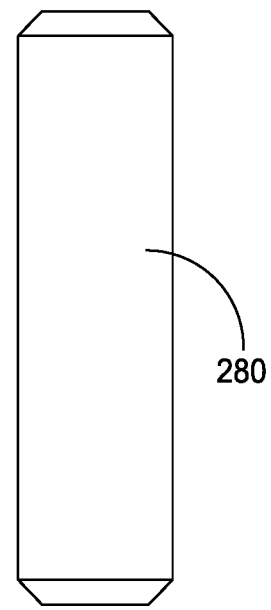
FIG. 21 is a front side view of the dowel illustrated in FIG. 20 in accordance with some embodiments.
Figure 22:
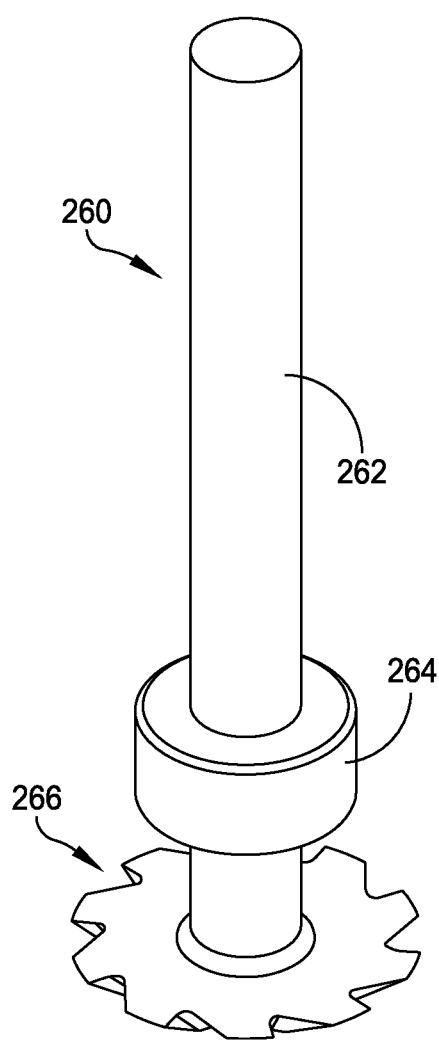
FIG. 22 is an isometric view of one example of a cutting tool that may be used in connection with the resection guide illustrated in FIG. 6 in accordance with some embodiments.
Figure 23:
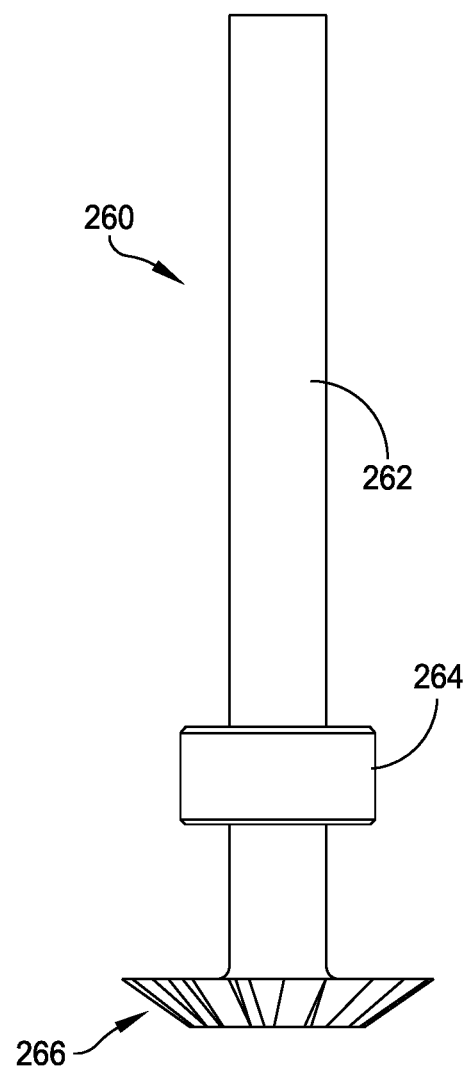
FIG. 23 illustrates a side view of the cutting tool illustrated in FIG. 22 in accordance with some embodiments.
Figure 24:
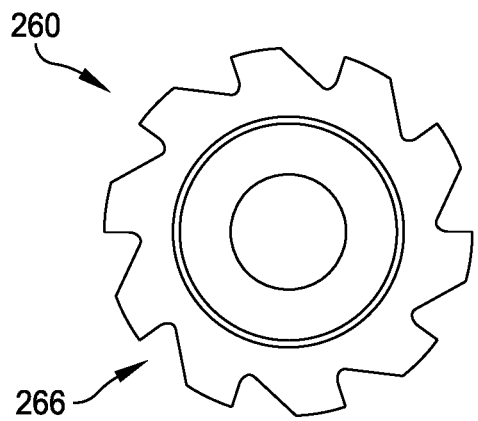
FIG. 24 is a top side view of the cutting tool illustrated in FIG. 22 in accordance with some embodiments.
Figure 25:
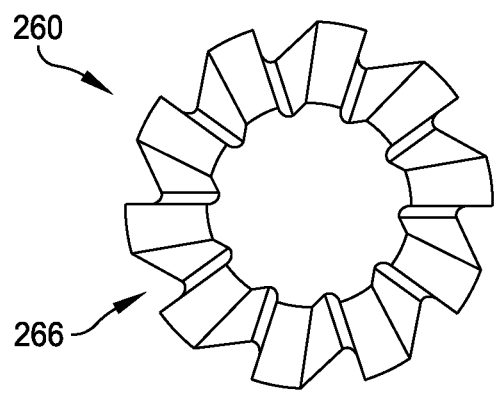
FIG. 25 is a bottom side view of the cutting tool illustrated in FIG. 22 in accordance with some embodiments.

Arm 246 of arm component 240 may include a coupling end 250 for coupling arm component 240 to a surgical tool. For example, as shown in FIGS. 17-19, coupling end may define an opening 252 sized and configured to receive, at least partially, a cutting tool therein. One of ordinary skill in the art will understand that the shape of opening 252, although illustrated as being generally circular, may be vary depending on the type of cutting tool that is to be supported. Opening 252 may communicate with a gap 254 in arm 246. In some embodiments, arm 246 may include a raised portion 256 forming a stop along a surface 258 of arm 246. The stop may be configured to engage a tab 270 that extends outwardly from a sleeve 268 as best seen in FIG. 6. For example, in some embodiments, a portion of the cutting tool 260 may be received within the sleeve 268, which is then locked into position of arm 246 by way of the tab 270 engaging the stop.

In use, the guide 200 is placed on a bone, such as a flat formed on the talus. For example, bottom surface 210 may be placed on a flat formed on the talus and the position of guide 200, or at least base component 202, on the talus may be checked using fluoroscopy. In some embodiments, a fluoroscopic image may be obtained of the sagittal plane such that slot 212 may be seen. As noted above, the angle of the leading edge 232 of slot 212 (FIG. 8) may identify the angle at which slot 230 extends through body 204 and thus the angle at which a posterior chamfer cut will be made. Once the desired position of the guide 200 on bone has been achieved, the guide 200 may be secured to the bone by inserting fixation elements into holes 220.

With guide 200 secured to the bone, a chamfer may be formed on the bone by passing a cutting instrument, such as a bone saw, through slot 230. In some embodiments, the chamfer is formed on a posterior portion of a talar dome.

Another cutting instrument, such as a reamer or the rotating cutting tool 260 illustrated in FIGS. 22-25, may be used to form another chamfer and/or flat cuts on the bone. For example, the shaft 262 of the cutting tool 260 may be inserted into opening 252 defined by arm component 240. As noted above, arm component 240 may be slideably coupled to base component 202 via the engagement of peg 244 extending from surface 248 of base 242 that is received within passageway 224 defined by base component 202. In some embodiments, the shoulder 264 of cutting tool 260 is positioned adjacent to and/or in abutment with arm 246. Bony cuts may then be made using the teeth 266 of the cutting tool 260 by moving the arm component 240 linearly along passageway 224 such that the cutting instrument moves in a medial-lateral/lateral-medial direction as will be understood by one of ordinary skill in the art. A dowel, such as dowel 280 shown in FIGS. 20-21, may be inserted into the hole 238 defined by base component 202 to limit the travel of arm component 240. In some embodiments, the chamfer formed using the guidance provided by arm component 240 is a chamfer formed on the anterior portion of a talar dome.

Once the cuts have been made using guide 200, the fixation elements may be removed from their engagement with the guide 200 and bone, and then the guide 200 may be removed from its abutment with the bone. Additional and/or finishing cuts may be made once the guide 200 is removed.

Resection Guide

Figure 26:
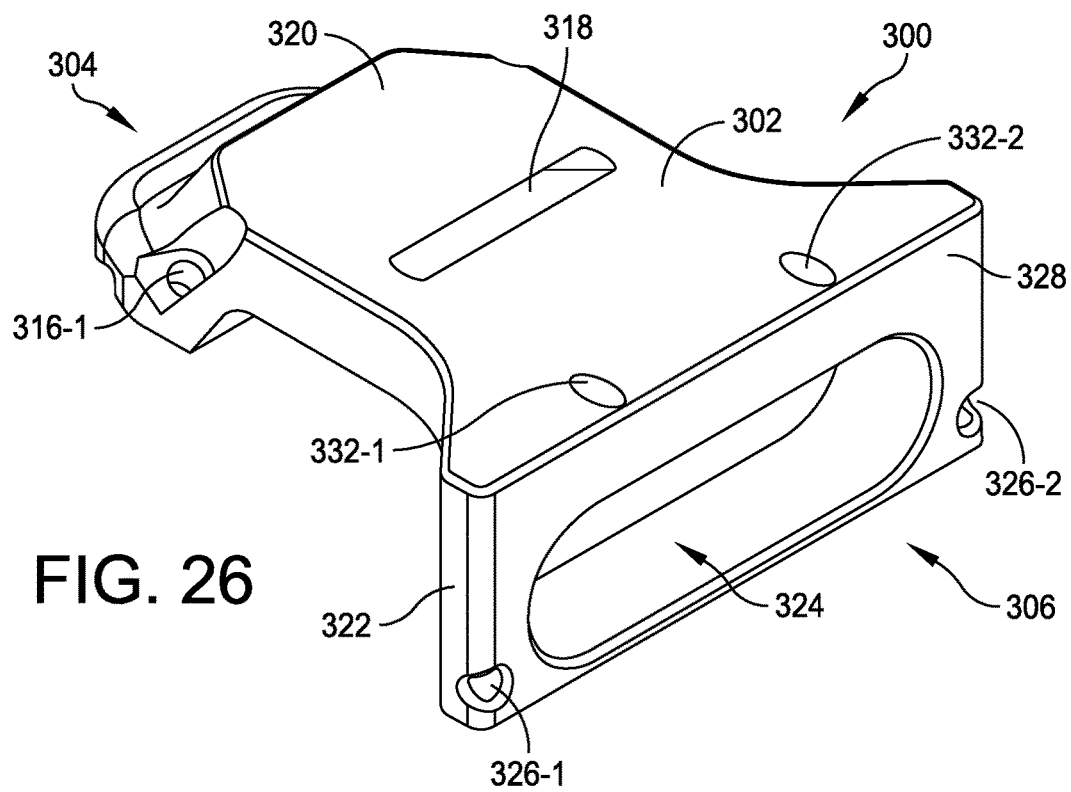
FIG. 26 is an isometric view of one example of a resection guide in accordance with some embodiments.
Figure 27:
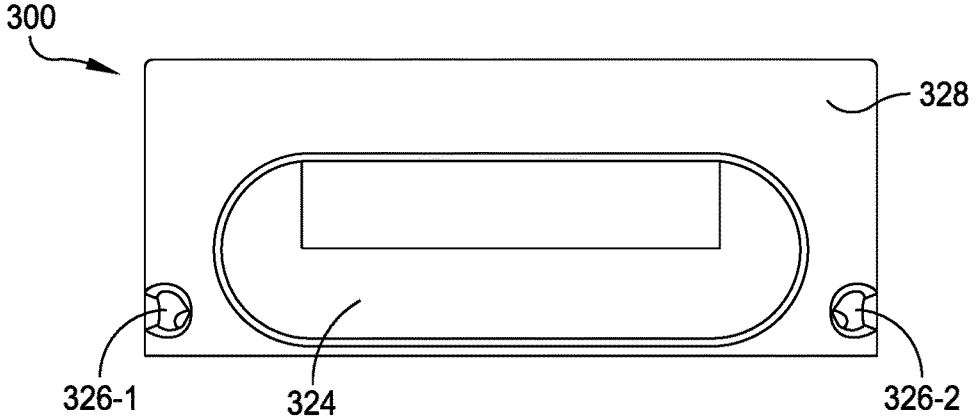
FIG. 27 is a front end view of the resection guide illustrated in FIG. 26 in accordance with some embodiments.
Figure 28:
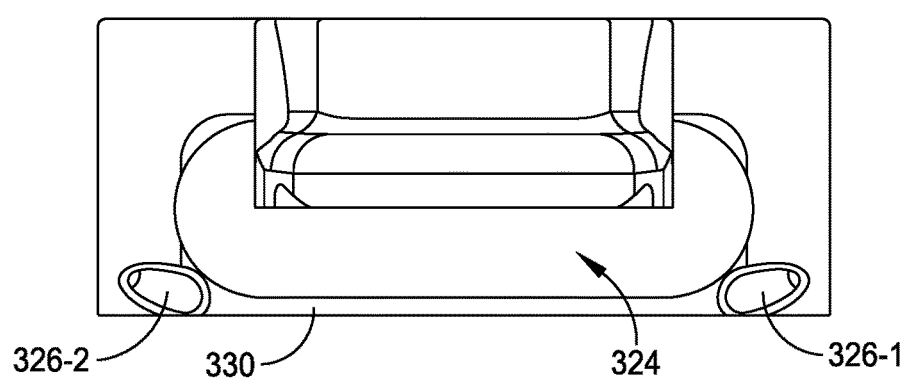
FIG. 28 is a rear end view of the resection guide illustrated in FIG. 26 in accordance with some embodiments.

FIGS. 26-31 illustrate one example of a resection guide 300 in accordance with some embodiments. Resection guide 300 may be used to perform both posterior and anterior chamfer resections. Referring first to FIG. 26, resection guide 300 has a body extending from an engagement end 304 for coupling to a bone, such as a talus, and a guide end 306. Engagement end 304 includes a flat surface 308 for being positioned on a flat formed on a bone. Engagement end 304 also defines a slot 310 extending across body 302 (i.e., from first side 312 to second side 314) and a pair of holes 316-1, 316-2 (collectively, "holes 316"). In some embodiments, holes 316 are positioned along opposite sides 312, 314 of body 302. Holes 216 are sized and configured to receive a fixation element, such as the threaded section 352 of threaded pins 350 illustrated in FIGS. 32-33, as described in greater detail below.

Figure 29:
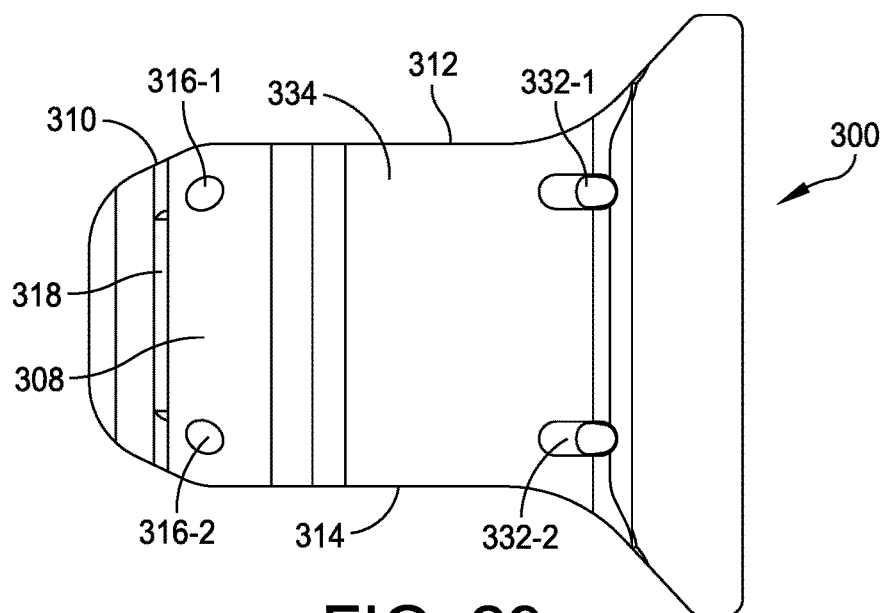
FIG. 29 is a bottom side view of the resection guide illustrated in FIG. 26 in accordance with some embodiments.
Figure 30:
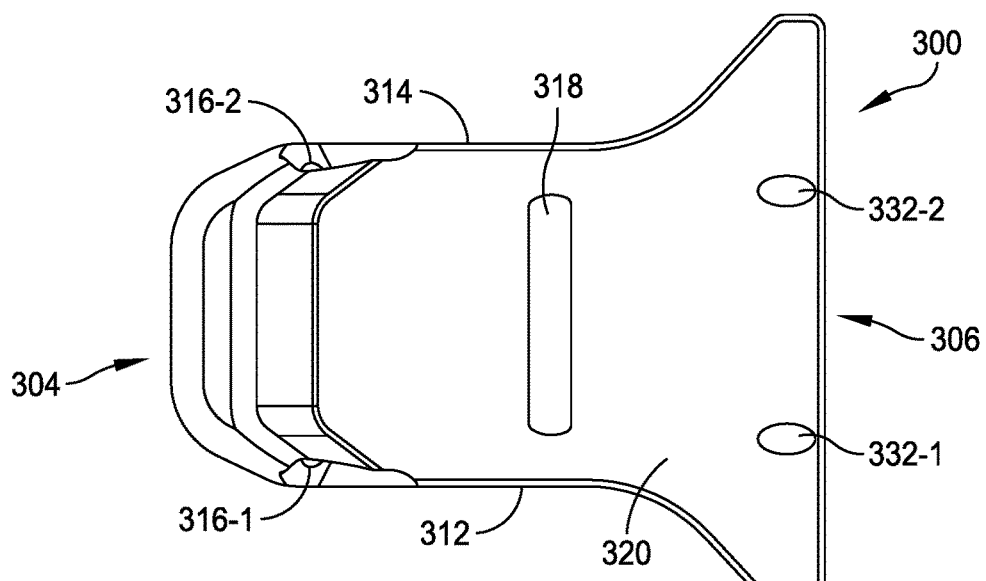
FIG. 30 is a top side view of the resection guide illustrated in FIG. 26 in accordance with some embodiments.

As best seen in FIGS. 26, 29, and 30, a slot 318 is formed through body 302 extending from the top side 326 to flat surface 308. In some embodiments, holes 316 and slot 318 are parallel with each other as they extend through body 302; however, one of ordinary skill in the art will understand that holes 316 and slot 318 may not be arranged such that they are parallel with one another. Slot 318 is sized and configured to receive a cutting tool, such as a saw, therethrough to provide a guide for making posterior chamfer cuts. As best seen in FIG. 29, slot 318 aligns and is in communication with slot 310 such that slot 310 may provide a surgeon with a visual indication of the angle and location of the posterior chamfer cut when viewing the guide 300 under sagittal plane fluoroscopy. To facilitate visualization under fluoroscopy, some or all of resection guide 300 may be formed from radiopaque material.

Figure 31:
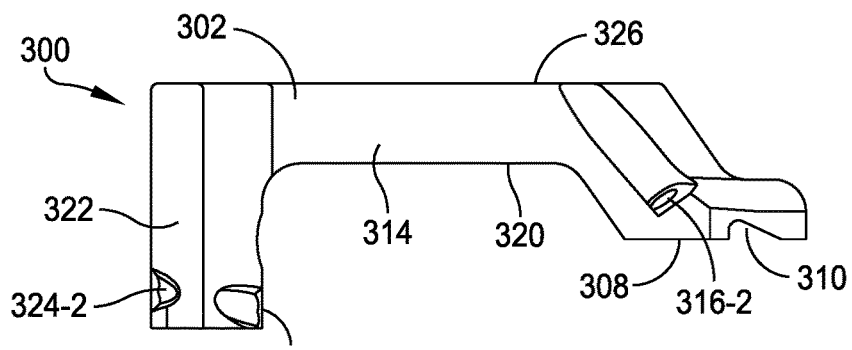
FIG. 31 is a side view of the resection guide illustrated in FIG. 26 in accordance with some embodiments.
Figure 34:
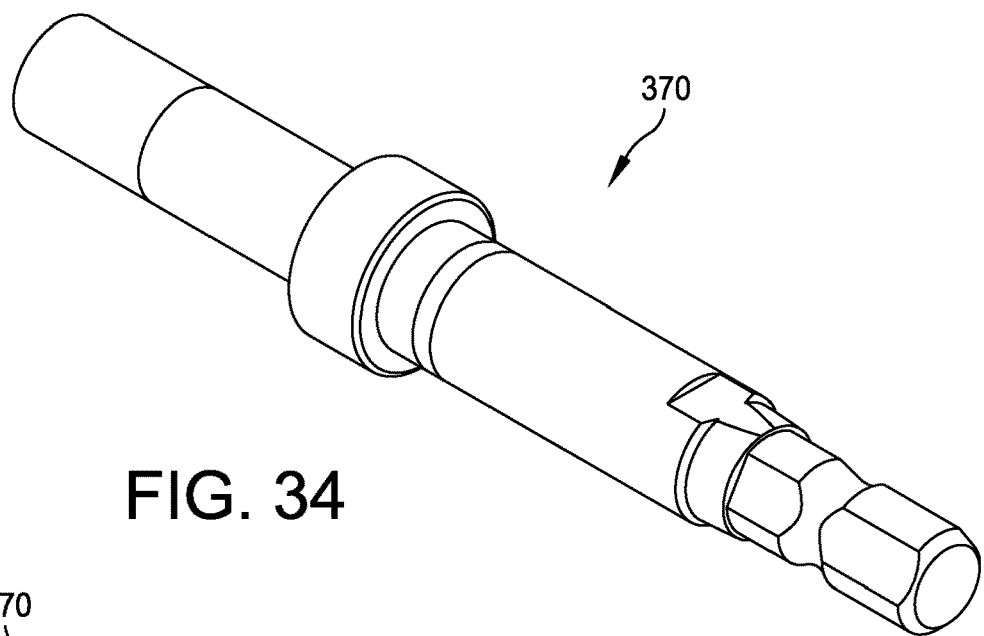
FIG. 34 is an isometric view of one example of a reaming cutting tool in accordance with some embodiments.
Figure 35:
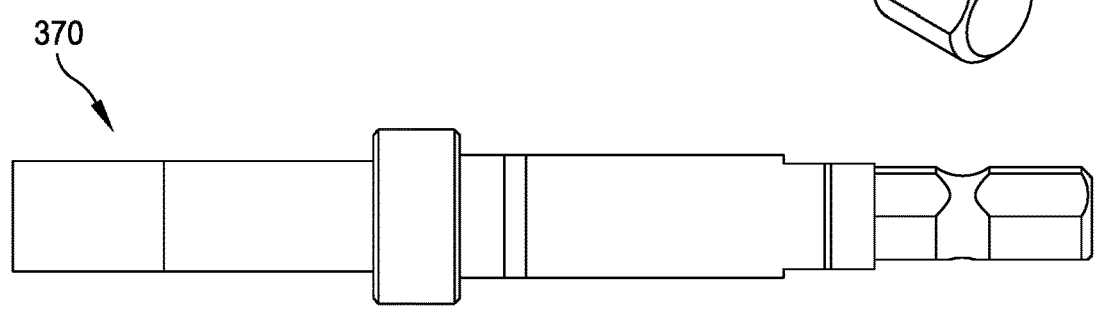
FIG. 35 a side view of the reaming cutting tool illustrated in FIG. 34 in accordance with some embodiments.
Figure 36:
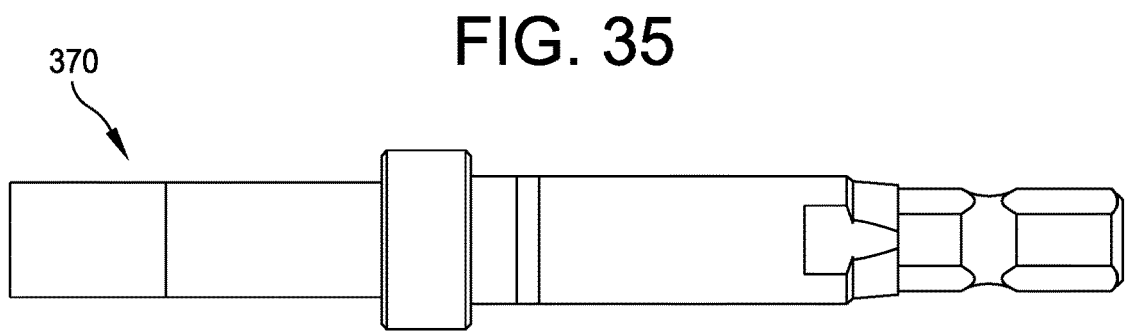
FIG. 36 is another side view of the reaming cutting tool illustrated in FIG. 34 in accordance with some embodiments.
Figure 37:
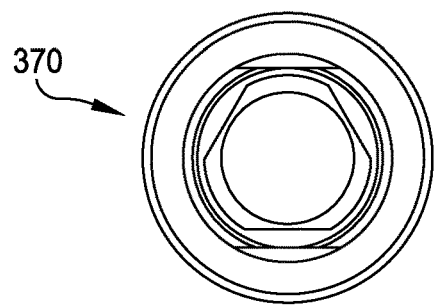
FIG. 37 is an end view of the reaming cutting tool illustrated in FIG. 34 in accordance with some embodiments.
Figure 38:
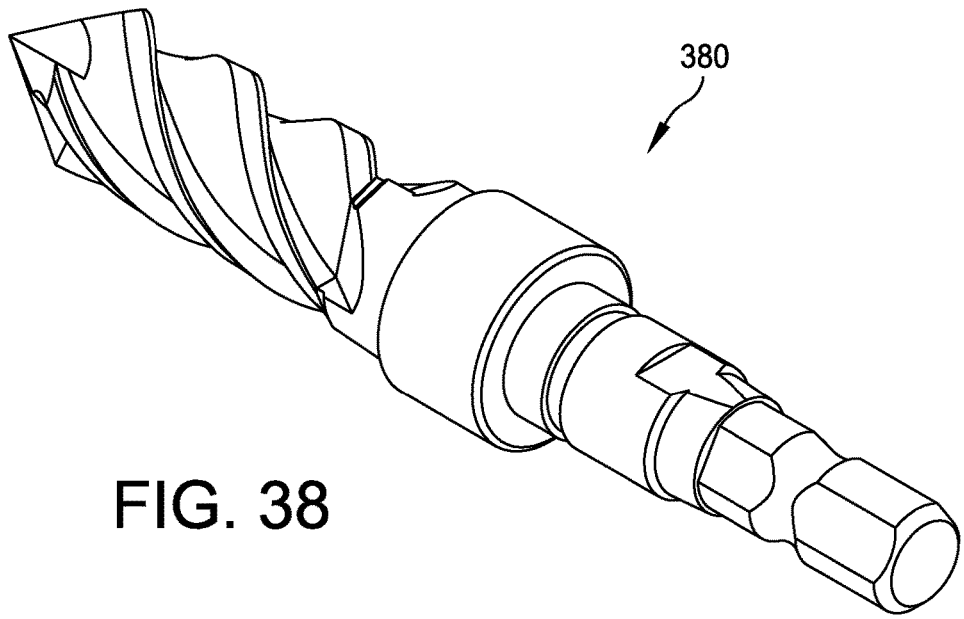
FIG. 38 is an isometric view of one example of an angled cutting tool in accordance with some embodiments.
Figure 39:
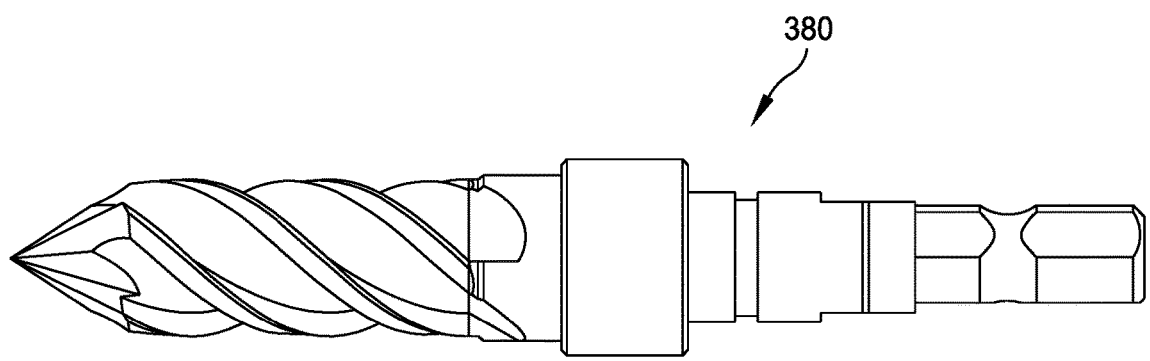
FIG. 39 is a side view of the angled cutting tool illustrated in FIG. 38 in accordance with some embodiments.
Figure 40:
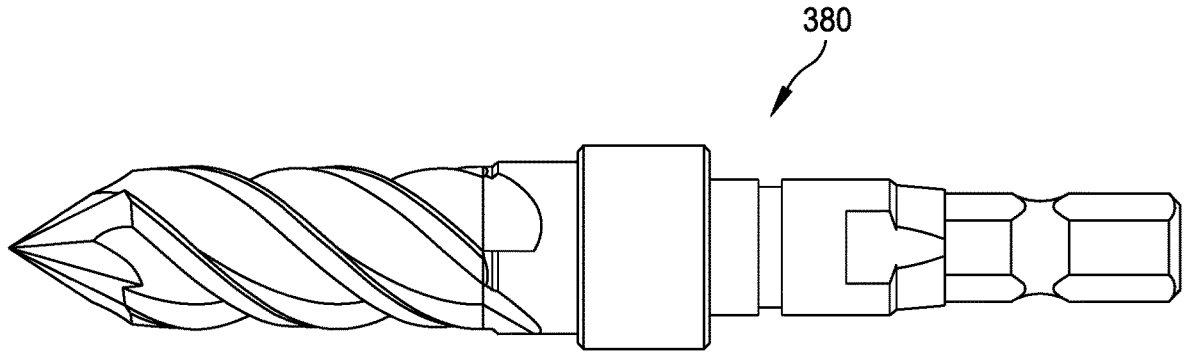
FIG. 40 is a side view of the angled cutting tool illustrated in FIG. 38 in accordance with some embodiments.

Guide end 306 includes an extension 322 extending from body 302 such that extension 322 has a thickness that is greater than a thickness of body 302 as best seen in FIG. 31. Extension 322 defines a guide channel 324 and one or more holes 326-1, 326-2 (collectively, "holes 326") each extending from front surface 328 of extension 322 to rear surface 330 of extension 320. Guide channel 324 is sized and arranged to guide a cutting tool, such as the reamer 370 shown in FIGS. 38-40, for guiding the cutting tool when making the anterior chamfer and/or flat cuts. In some embodiments, holes 326 are arranged such that they are not parallel with one another (e.g., are divergent) to firmly secure guide 300 to a bone while making the anterior chamfer and/or flat cuts. Guide 300 may define another pair of holes 332-1, 332-2 (collectively, "holes 332") that extend from top side 320 (FIG. 29) to underneath side 334 (FIG. 30). In some embodiments, holes 332 are spaced equally to the holes 116 of talar dome trial 100 shown in FIGS. 1-5.

In use, resection guide 300 may be coupled to a flat formed on a bone, such as a talus, by placing surface 308 on the formed flat. The location of guide 300 relative to the bone may be checked using fluoroscopy. For example, a surgeon or other practitioner may check the position of the guide 300 on a bone to confirm that slot 310, which identifies the location and angle of slot 318 (and thus the location and angle of a chamfer cut) is at the desired location. When the desired positioning of guide 300 has been achieved, pins, k-wires, or other fixation elements, such as threaded pins 350, may be inserted through holes 316 to secure guide 300 to the bone. For example, pins 350 may be inserted by coupling a T-handle (not shown) to the engagement shoulder 356) and then using the T-handle to tap the self-tapping threaded end 352 into the bone. In some embodiments, the threaded end 352 is threaded into bone until shoulder 354 comes into contact with resection guide 300. As shown in FIGS. 32 and 33, the engagement shoulder 356 may be disposed between unthreaded sections 358-1, 358-2 (collectively, "unthreaded sections 358" or "unthreaded section 358"). Additional securement may be provided by inserting other fixation devices through holes 326.

Figure 41:
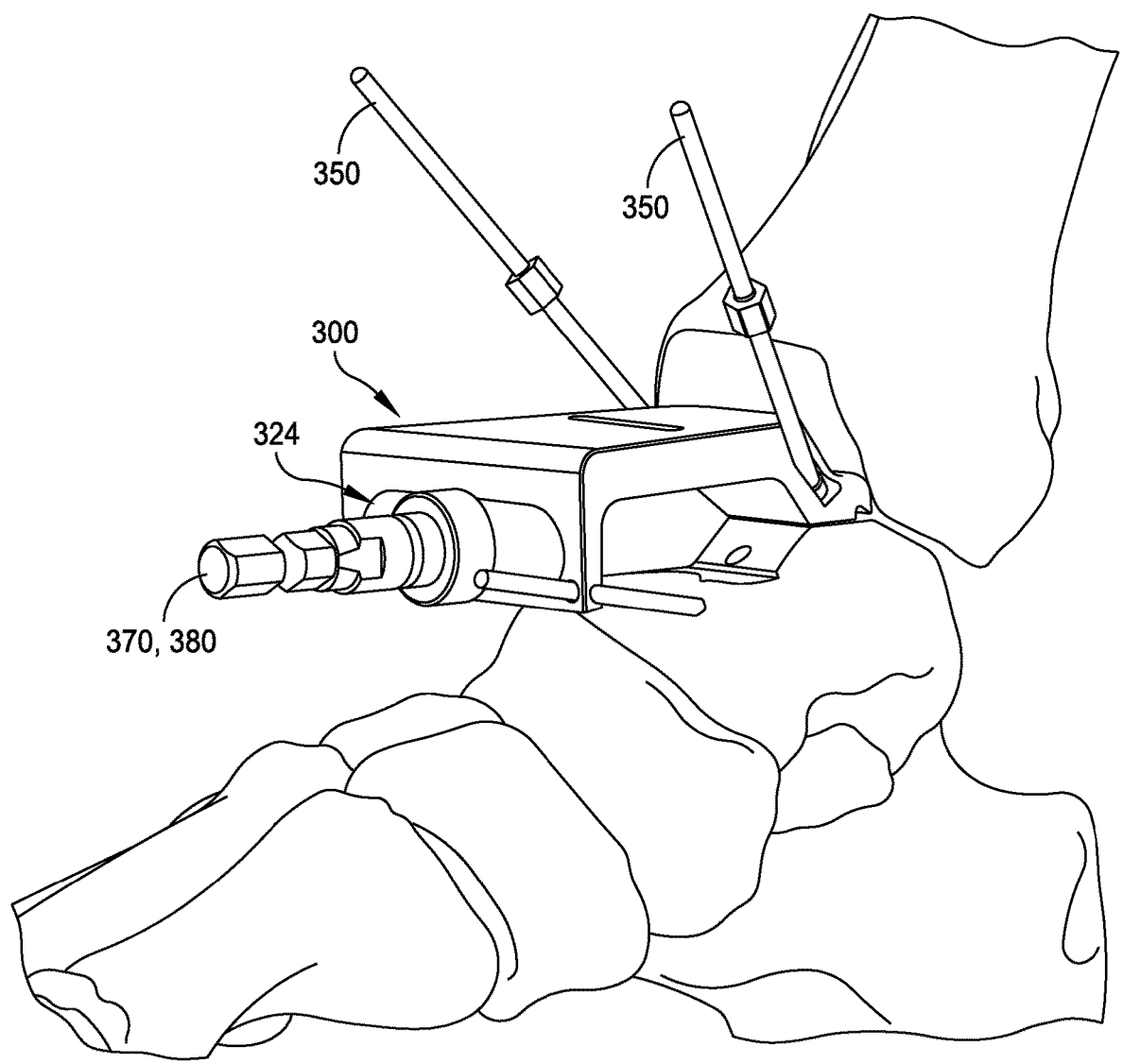
FIG. 41 illustrates one example of the resection guide illustrated in FIGS. 26-31 being secured to bone and guiding cutting tools in accordance with some embodiments.

With guide 300 secured to the bone, bony cuts may be made using the guide 300 to form posterior and/or anterior chamfers. For example, making posterior chamfer cuts may include inserting a saw into and through slot 318. The saw may be moved side-to-side within and along slot 318. An anterior chamfer and/or anterior flat may be formed by inserting another cutting tool, such as an angled reamer 380 illustrated in FIGS. 38-40, into guide channel 324. As best seen in FIG. 41, the reamers may be moved along guide channel 324 to form the anterior chamfer and/or flat cuts as will be understood by one of ordinary skill in the art.

Once the desired cuts have been made using guide 300, the fixation elements may be removed from their engagement with the bone and guide 300 such that guide 300 may also be removed from its contact with bone. In some embodiments, with guide 300 removed, additional finishing cuts may be made to the posterior and/or anterior chamfers as will be understood by one of ordinary skill in the art.

Anterior Cut Guide

FIGS. 42-47 illustrate one example of an anterior cutting guide in accordance with some embodiments. Cutting guide 400 includes an upper surface 402 and a lower surface 404. In some embodiments, upper surface 402 includes a first planar surface 402-1 and a second planar surface 402-2 that is disposed at angle relative to first planar surface 402-1. Lower surface 404 may include a first planar surface 404-1, a second planar surface 404-2, a third planar surface 404-3, and a fourth planar surface 404-4. In some embodiments, planar surfaces 404-1, 404-3 are parallel to one another and planar surfaces 404-2, 404-4 are disposed at angles with respect to surfaces 404-1, 404-3.

Figure 45:
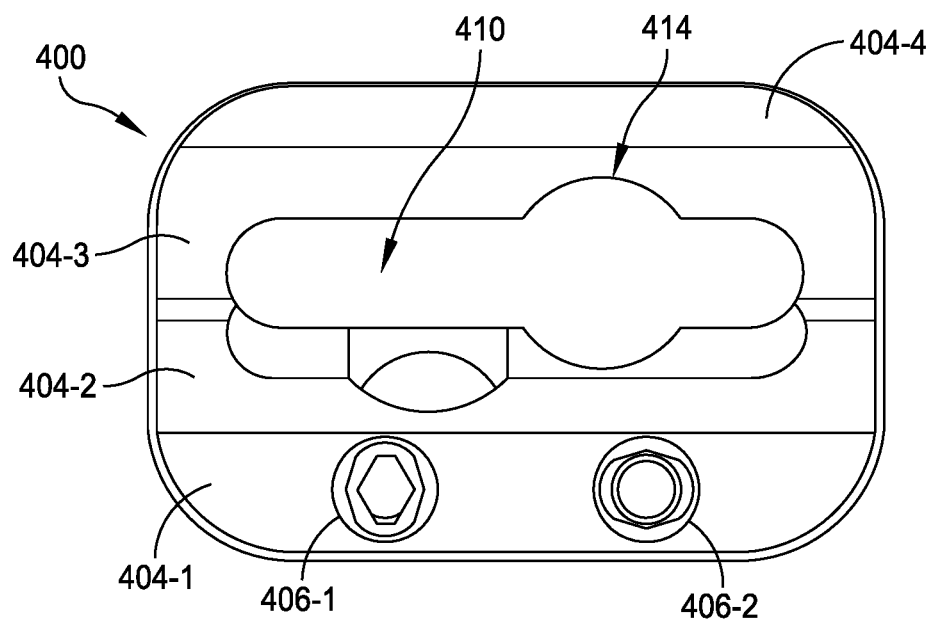
FIG. 45 is a bottom side view of the cutting guide illustrated in FIG. 42 in accordance with some embodiments.
Figure 46:
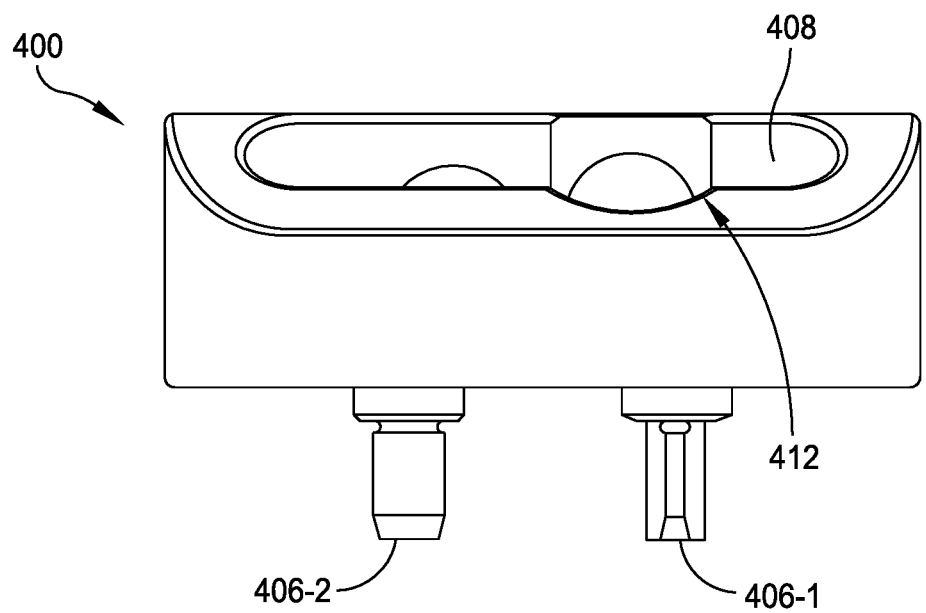
FIG. 46 is a front side view of the cutting guide illustrated in FIG. 42 in accordance with some embodiments.
Figure 47:
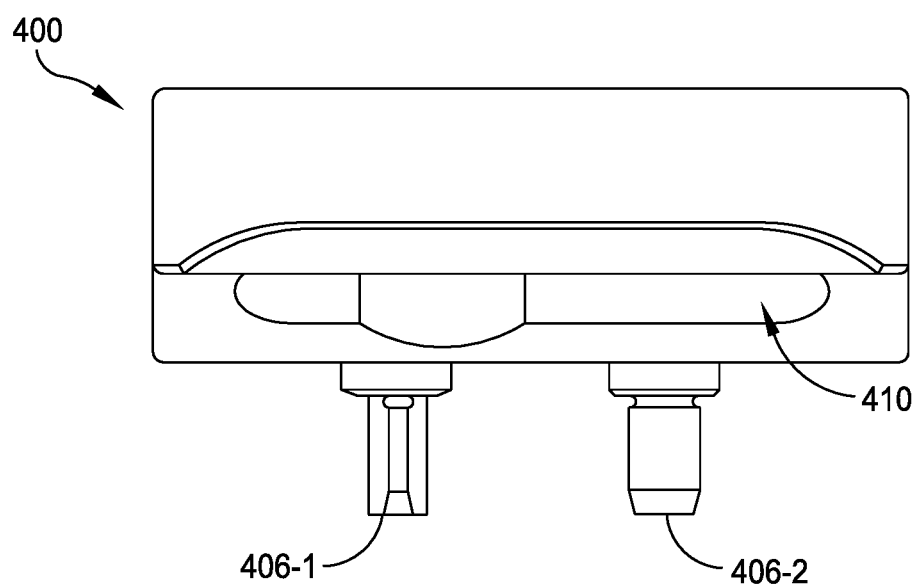
FIG. 47 is a rear side view of the cutting guide illustrated in FIG. 42 in accordance with some embodiments.
Figure 48:
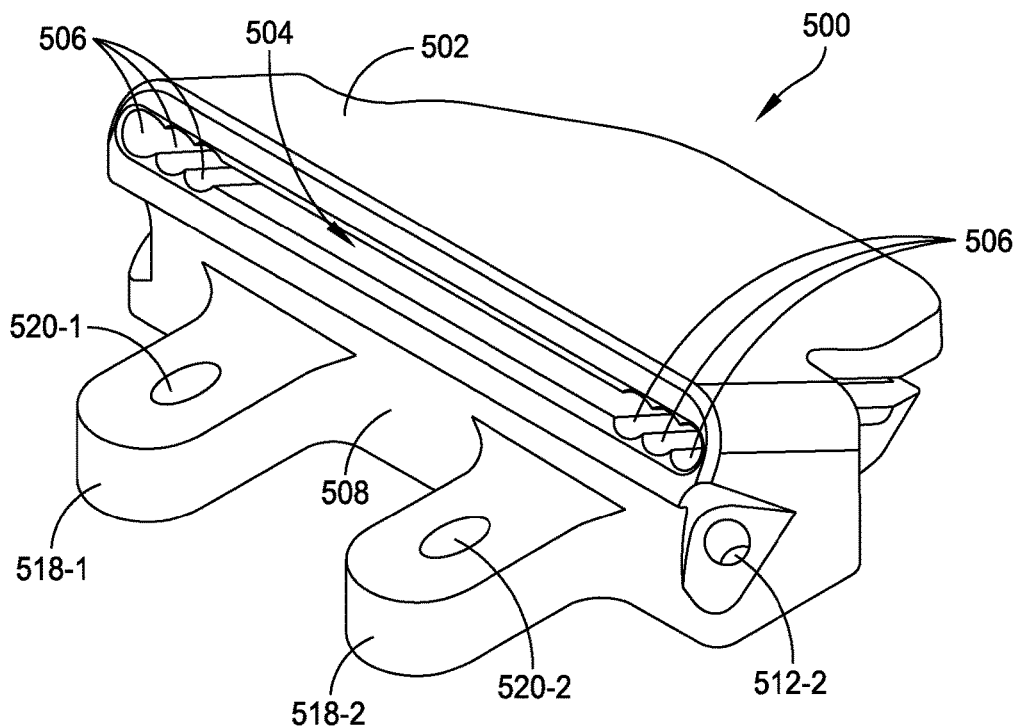
FIG. 48 is an isometric view of a cutting guide in accordance with some embodiments.
Figure 49:
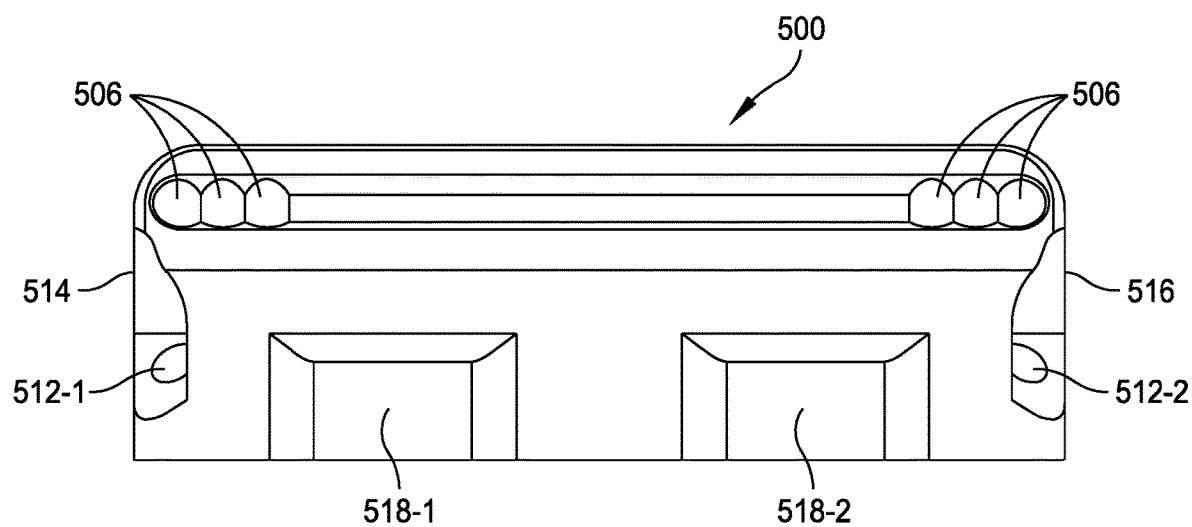
FIG. 49 is a rear view of the cutting guide illustrated in FIG. 48 in accordance with some embodiments.
Figure 50:
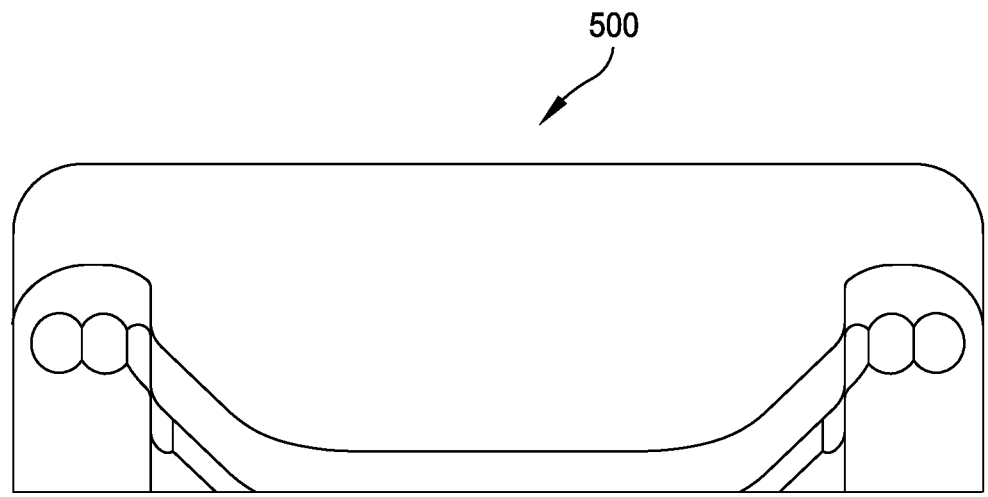
FIG. 50 is a front side view of the cutting guide illustrated in FIG. 48 in accordance with some embodiments.

As best seen in FIGS. 45, planar surface 404-1 of lower surface 404 includes one or more pegs 406-1, 406-2 (collectively, "pegs 406") extending therefrom. In some embodiments, pegs 406 are sized and arranged (e.g., spaced apart) such that cutting guide 400 may be coupled to a base component, such as the talar resection guide base 2100 disclosed in the '561 Patent. For example, pegs 406 may be received within holes 2116, 2118 defined by the resection guide base 2100 as described in greater detail below.

Guide 400 defines a pair of slots 408, 410 extending parallel to one another in a lengthwise direction across guide 400. Slot 408 extends from planar surface 402-2 of upper surface 402 to planar surfaces 404-2, 404-3 of bottom surface 404. Slot 410 extends from planar surface 402-1 of upper surface 402 to planar surfaces 404-2, 404-3 of bottom surface 404.

Figure 42:
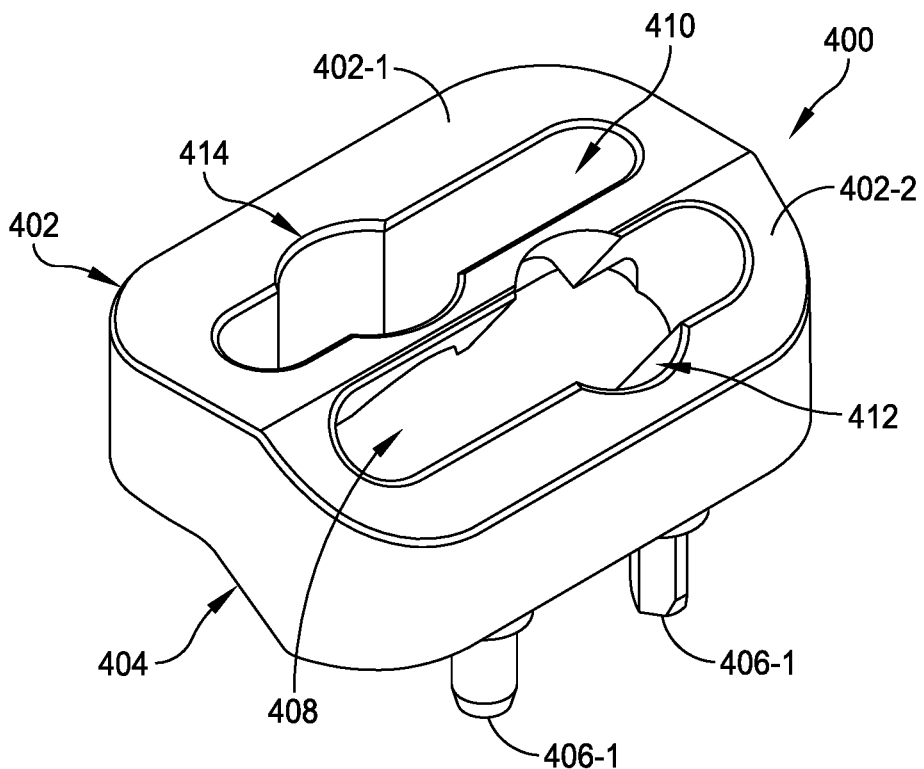
FIG. 42 is an isometric view of one example of a cutting guide in accordance with some embodiments.
Figure 43:
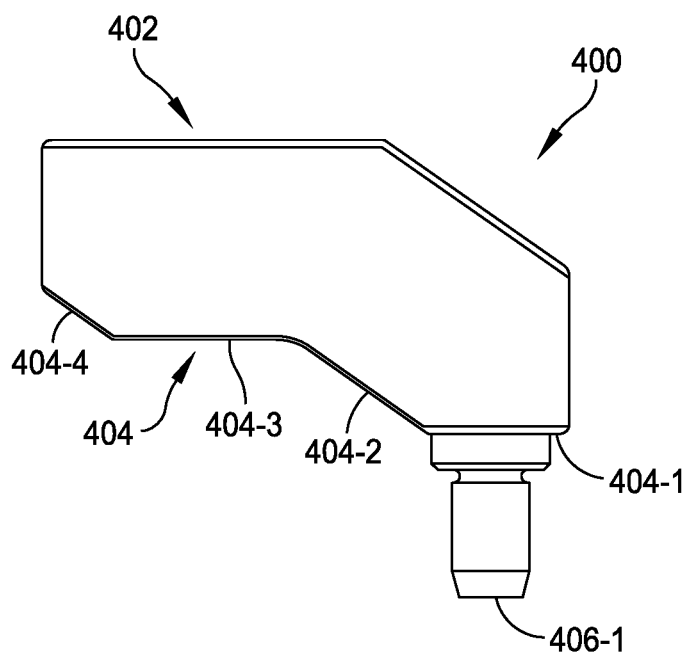
FIG. 43 is a side view of the cutting guide illustrated in FIG. 42 in accordance with some embodiments.
Figure 44:
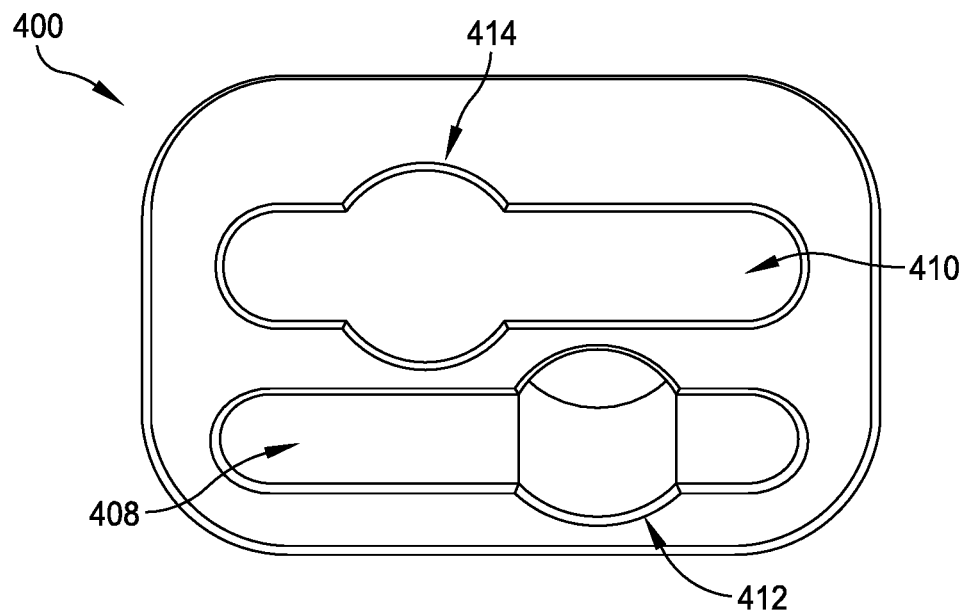
FIG. 44 is a top side view of the cutting guide illustrated in FIG. 42 in accordance with some embodiments.

In some embodiments, slot 408 includes an enlarged area 412 disposed along its length. As shown in FIGS. 42, 44, and 45, enlarged area 412 may have a circular geometry, although one of ordinary skill in the art will understand that enlarged area 412 may have other geometries or shapes. Slot 410 may also include an enlarged area 414 along its length. Like enlarged area 412, enlarged area 414 may have a circular shape, but may have other shapes as will be understood by one of ordinary skill in the art.

In use, the guide 400 may be coupled to a base component, such as the talar resection guide base 2100 disclosed in the '561 Patent. As disclosed in the '561 Patent, the talar guide base 2100 may be coupled to a bone, such as a talus, by a fixation element, such as a fixation pin or k-wire. Coupling the guide 400 to the base component may include inserting pegs 406 into holes 2116, 2118. With guide 400 coupled to the base component, slot 408 is aligned with slot 2102 defined by the base component. An initial plunge cut may be made by inserting a cutting tool, such as a reamer, into enlarged area 412 along the length of slot 408. The same or another cutting tool may then be moved along the length of slot 408 to cut the bone.

Once the desired cutting has been achieved using the guidance provided by 408, guide 400 remains coupled to the base component, slot 410 is aligned with slot 2124 defined by the base component. An initial plunge cut may be made by inserting a cutting tool, such as a reamer, into enlarged area 414 along the length of slot 410. Once the desired cutting has been achieved using the guidance provided by 408 and 410, guide 400 may be removed from its engagement with the base component. The same or another cutting tool may then be moved along the length of slot 410 to make additional bone resections as will be understood by one of ordinary skill in the art.

Posterior Referencing Chamfer Guides

Figure 51:
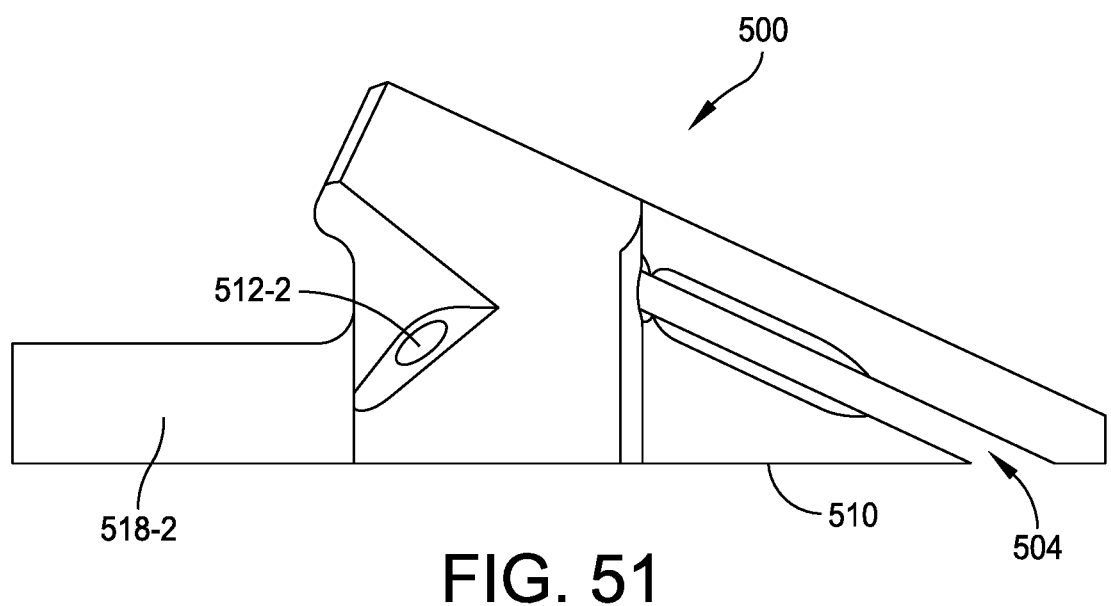
FIG. 51 is a side view of the cutting guide illustrated in FIG. 48 in accordance with some embodiments.
Figure 52:
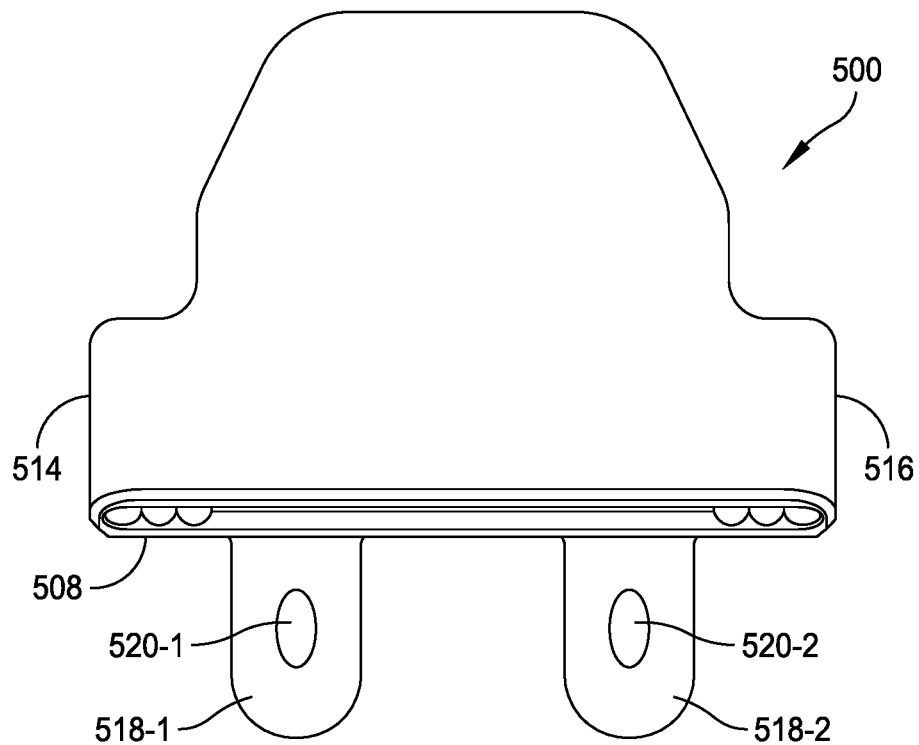
FIG. 52 is a top side view of the cutting guide illustrated in FIG. 48 in accordance with some embodiments.
Figure 53:
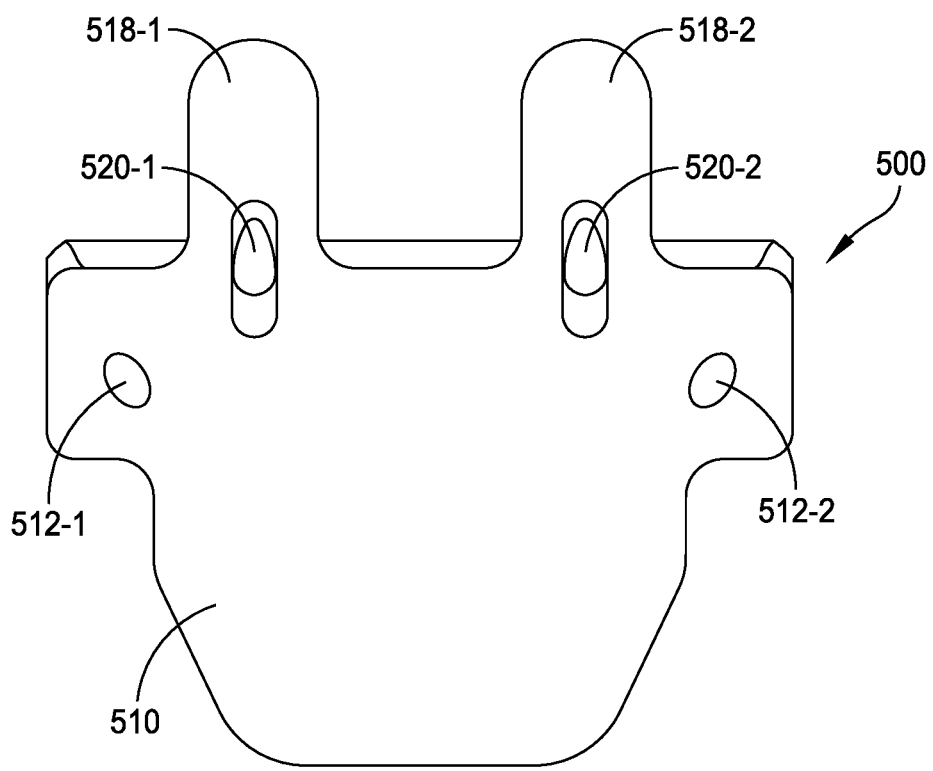
FIG. 53 is a bottom side view of the cutting guide illustrated in FIG. 48 in accordance with some embodiments.

FIGS. 48-64 illustrate examples of posterior-referencing chamfer cutting guides in accordance with some embodiments. Referring first to FIGS. 48-54, a posterior chamfer cutting guide 500 is shown having a body 502 defining a cutting slot 504. In some embodiments, slot 504 includes one or more protection holes 506 along its length. Slot 504 (and holes 506) extends at an angle from rear side 508 to the bottom side 510 as best seen in FIG. 51.

Body 502 defines a pair of holes 512-1, 512-2 (collectively, "holes"), with hole 512-1 being positioned alongside 514 and hole 512-2 being positioned alongside 516. Body 502 also includes one or more tangs 518-1, 518-2 (collectively, "tangs 518") extending away from the rear side 508. Each tang 518-1, 518-2 defines a respective hole 520-1, 520-2 (collectively, "holes 520") sized and configured to receive a fixation element, such as a k-wire or pin, therein.

Figure 54:
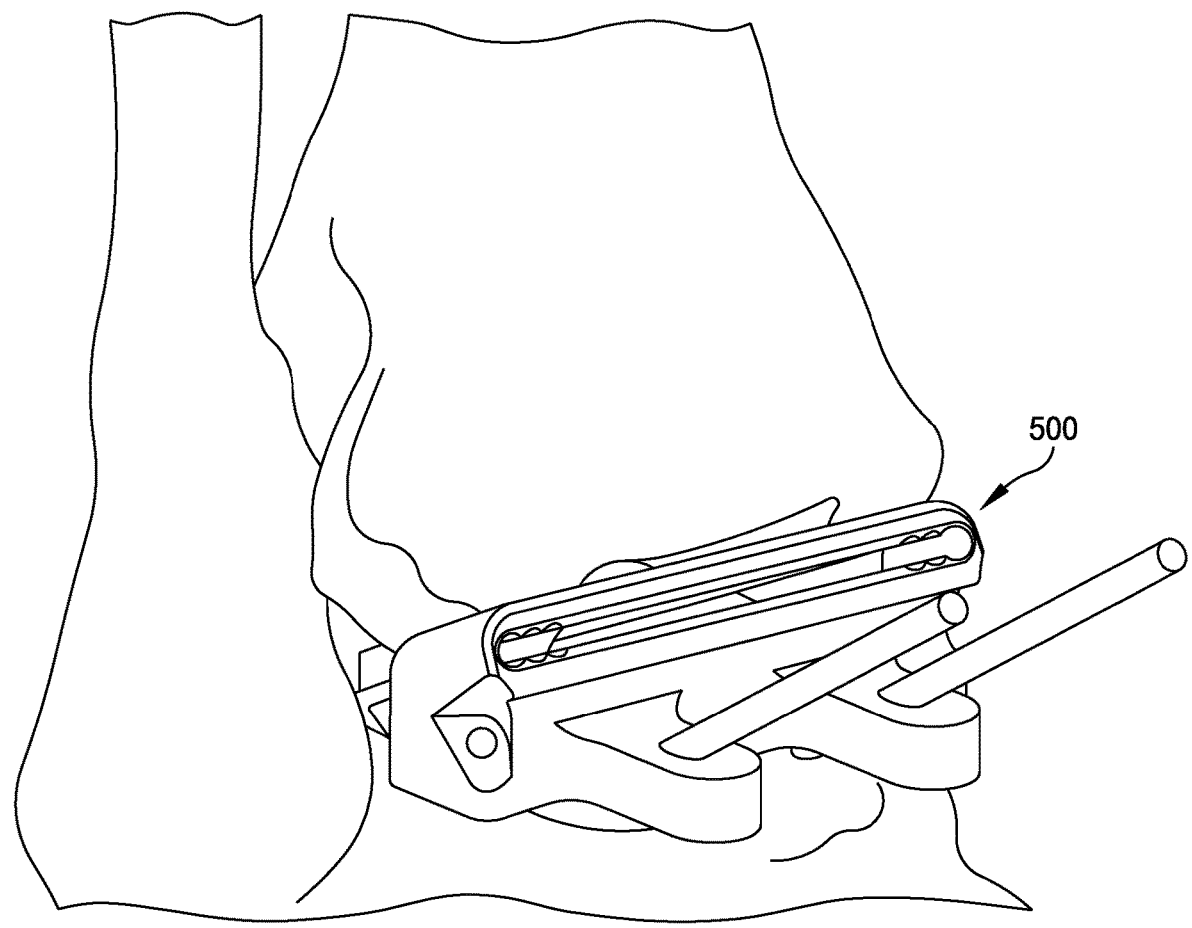
FIG. 54 illustrates one example of the cutting guide illustrated in FIG. 48 coupled to bone in accordance with some embodiments.

As shown in FIG. 54, the cutting guide 500 is placed on a bone, such as a talus, and is secured to the bone by inserting one or more fixation elements through holes 512 and/or holes 520. Additional fixation elements may be inserted through the protection holes 506 disposed along the length of slot 504. A cutting tool, such as a bone saw, is inserted through slot 504 to make a chamfer cut, such as a posterior chamfer cut. The cutting guide 500 may then be removed from its engagement with the fixation elements and another guide may be installed to make an anterior chamfer cut.

Figure 55:
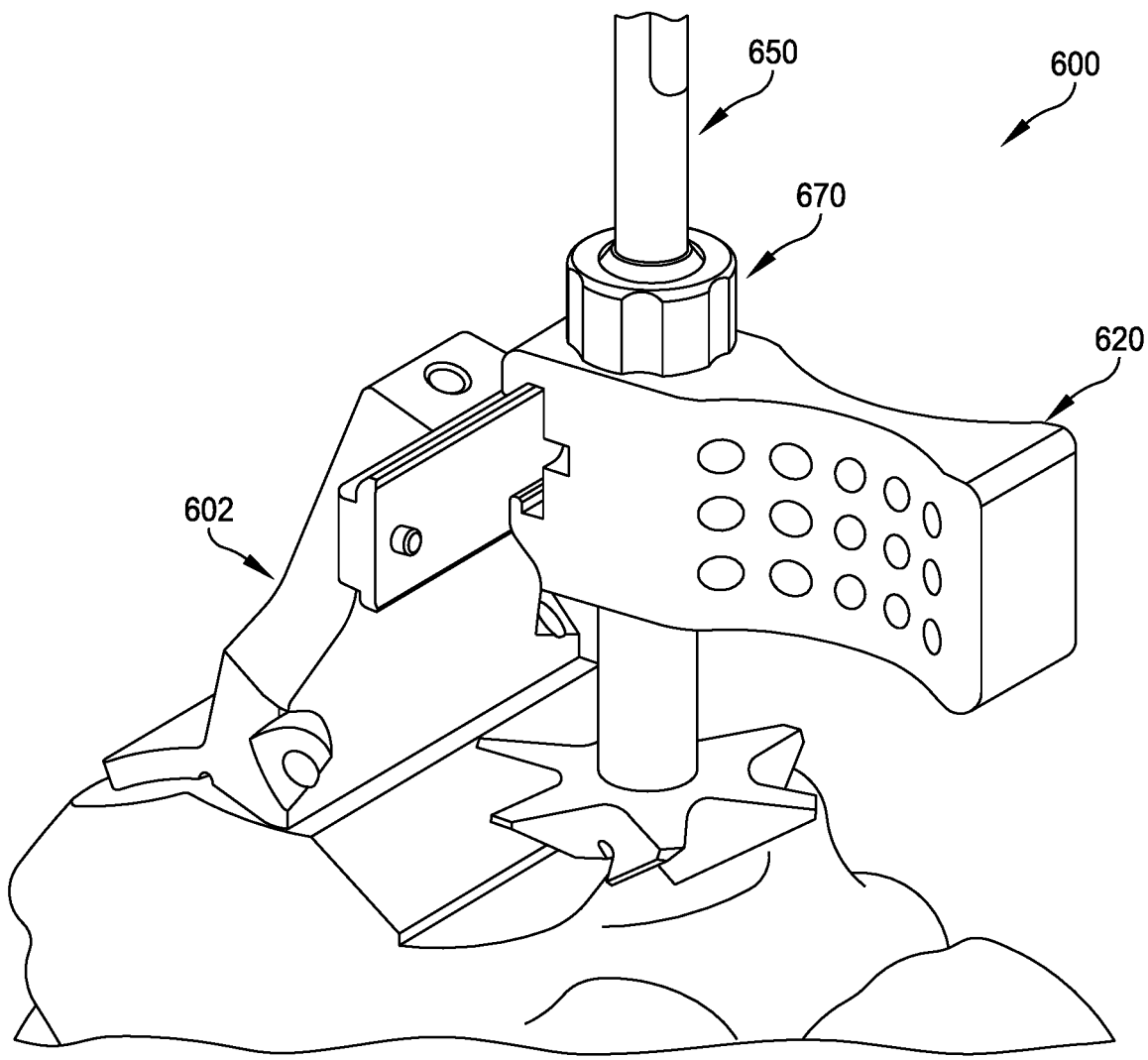
FIG. 55 illustrates one example of a cutting guide and guiding a cutting tool in accordance with some embodiments.
Figure 56:
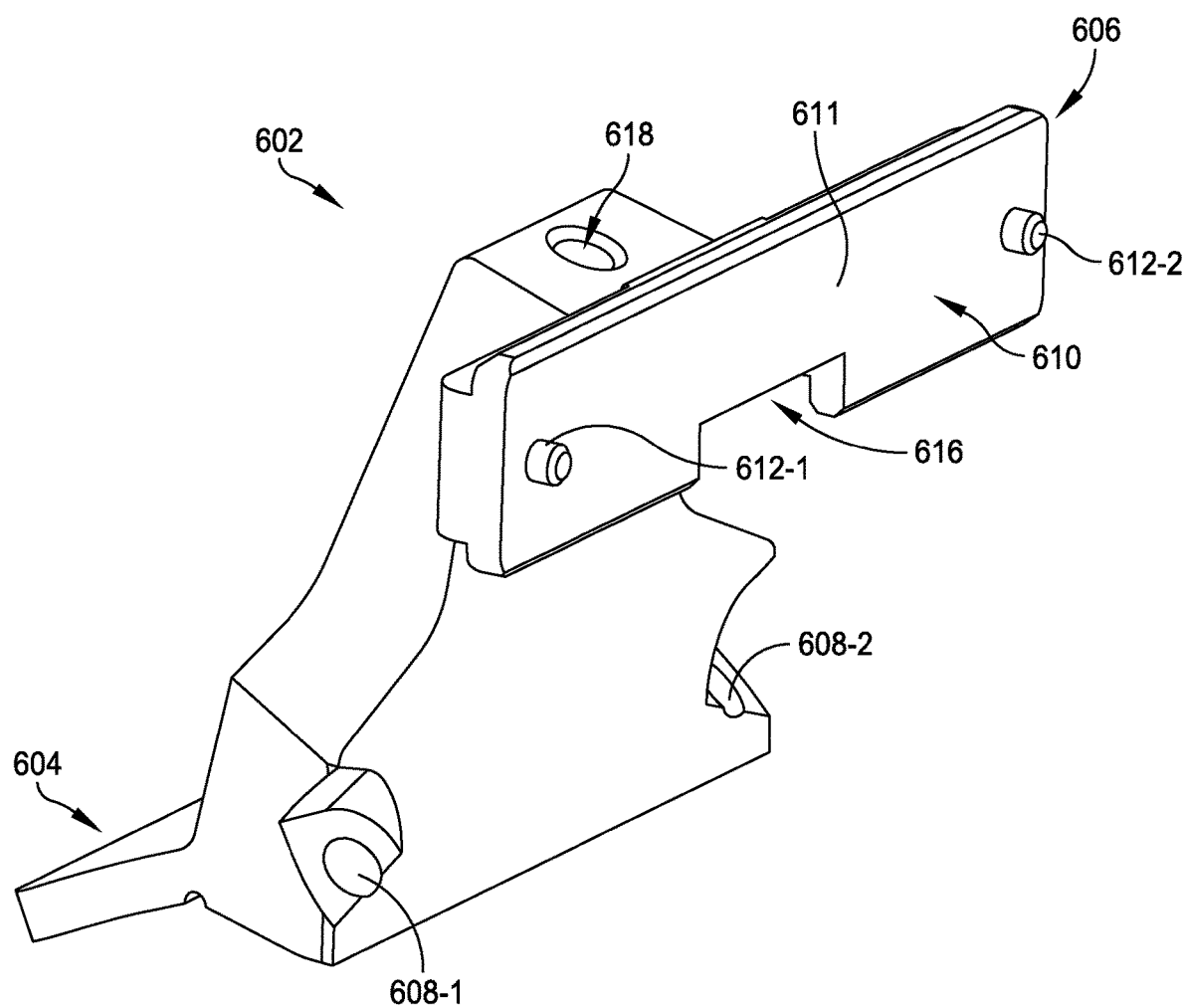
FIG. 56 is an isometric view of one example of a base component of the cutting guide illustrated in FIG. 55 in accordance with some embodiments.
Figure 57:
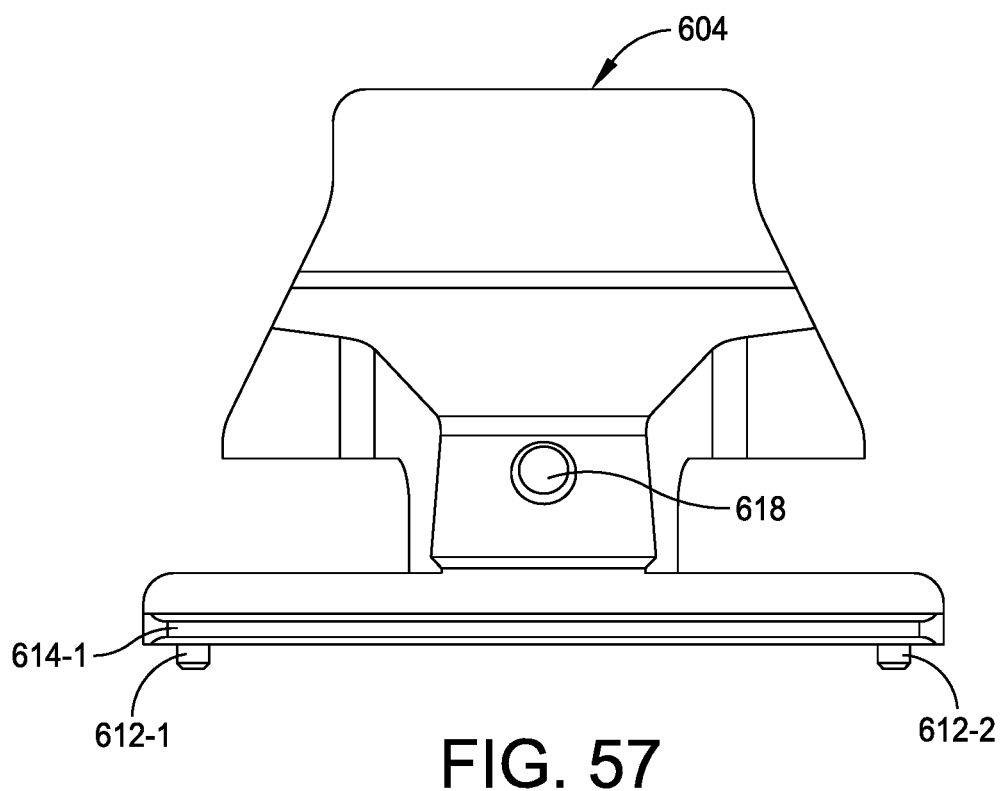
FIG. 57 is a top side plan view of the base component illustrated in FIG. 56 in accordance with some embodiments.
Figure 58:
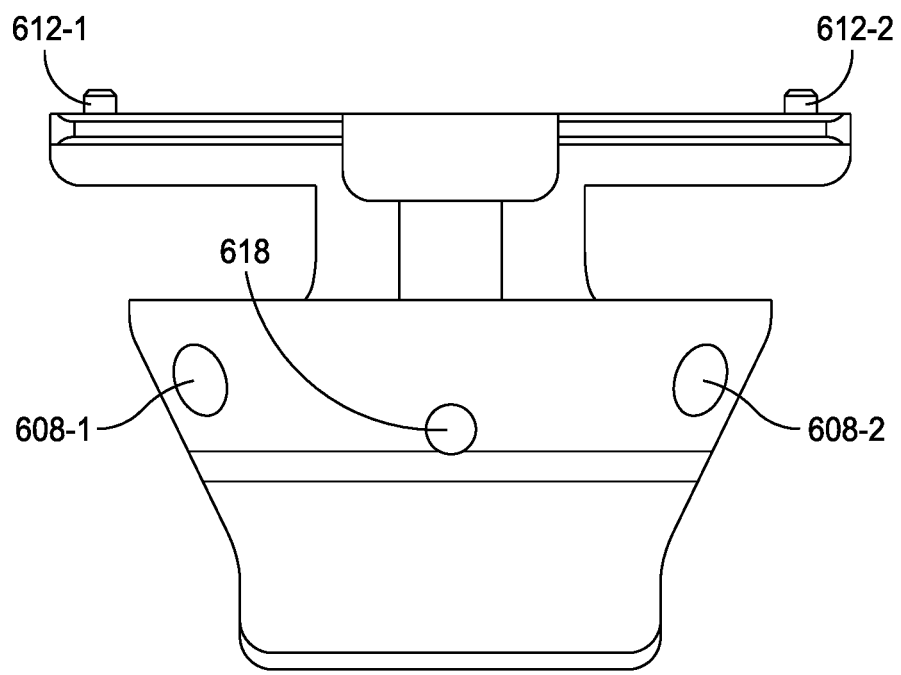
FIG. 58 is a bottom side plan view of the base component illustrated in FIG. 56 in accordance with some embodiments.
Figure 59:
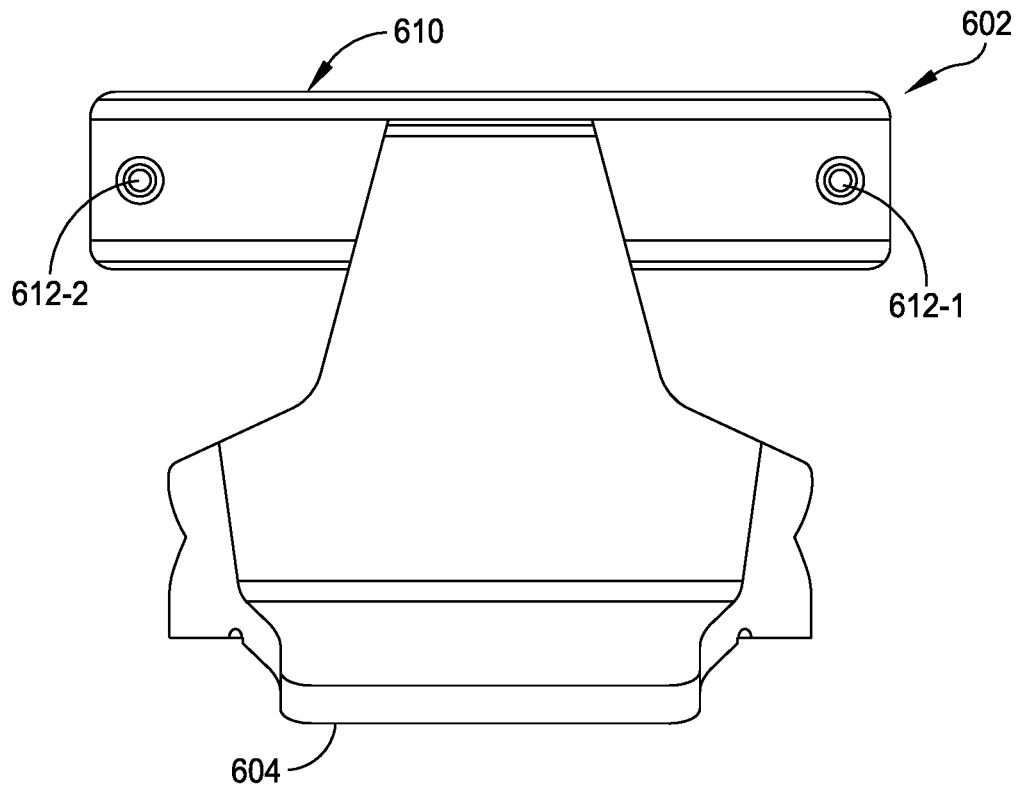
FIG. 59 is a front side view of the base component illustrated in FIG. 56 in accordance with some embodiments.
Figure 60:
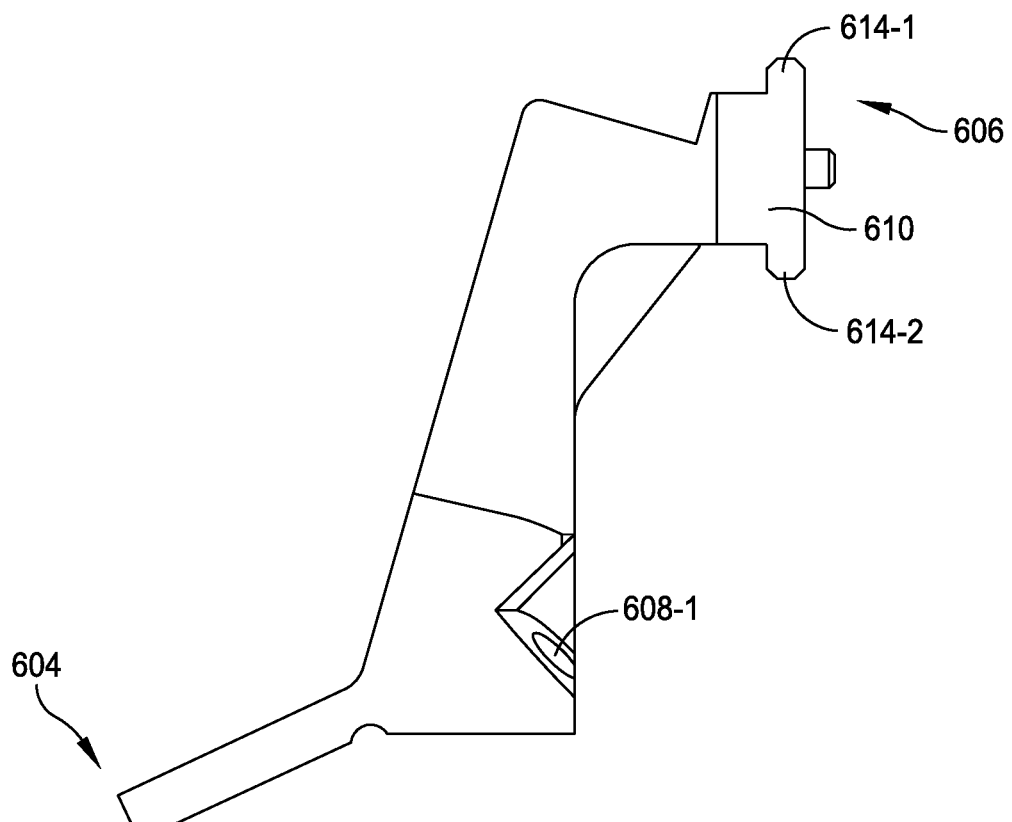
FIG. 60 is a side view of the base component illustrated in FIG. 56 in accordance with some embodiments.
Figure 61:
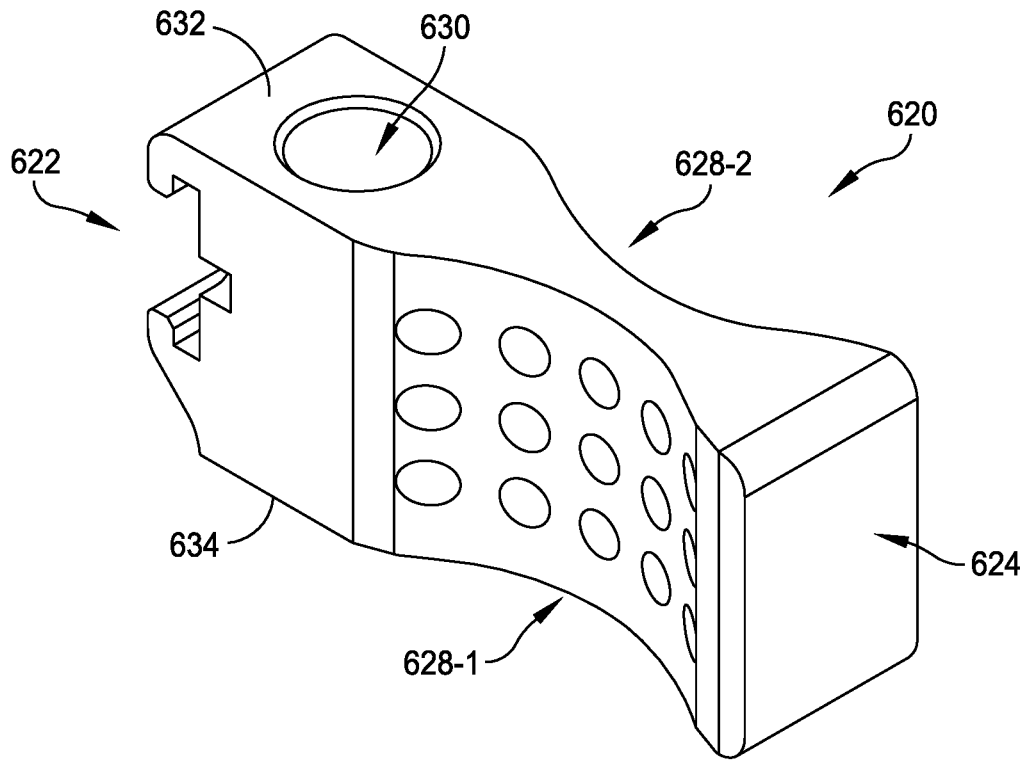
FIG. 61 is an isometric view of an arm component of the cutting guide illustrated in FIG. 55 in accordance with some embodiments.
Figure 62:
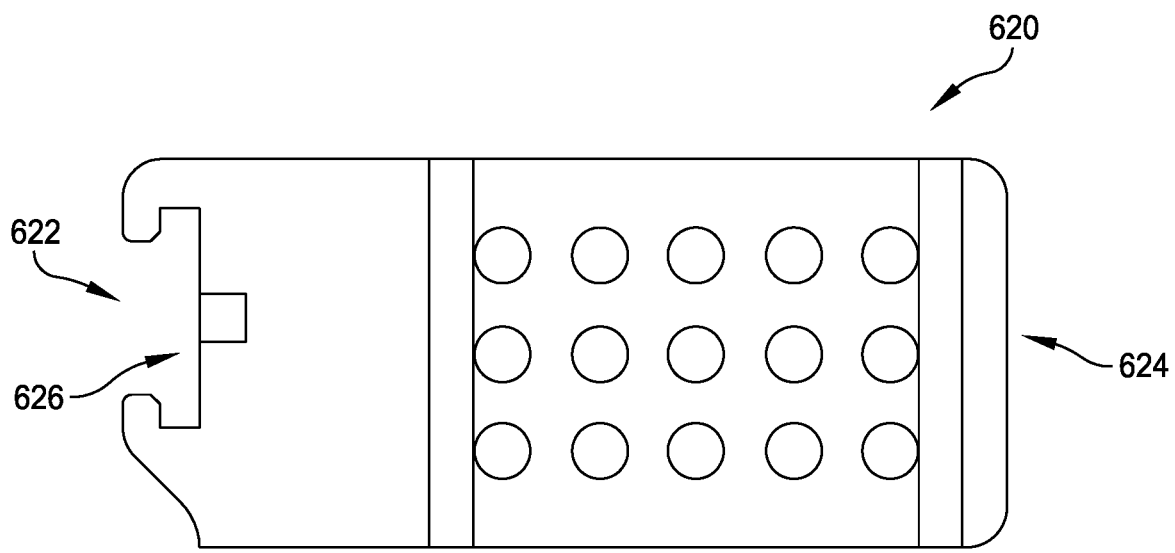
FIG. 62 is a side view of the arm component illustrated in FIG. 61 in accordance with some embodiments.
Figure 63:
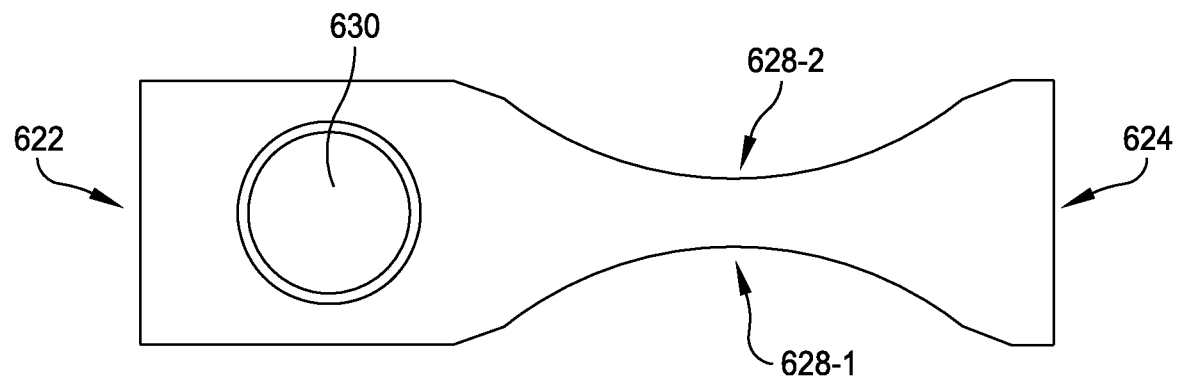
FIG. 63 is a top side plan view of the arm component illustrated in FIG. 61 in accordance with some embodiments.
Figure 64:
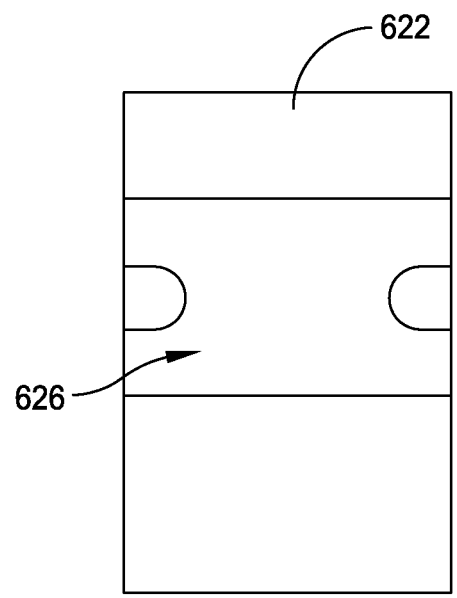
FIG. 64 is a view of the coupling end of the arm component illustrated in FIG. 61 in accordance with some embodiments.

One example of such a cutting guide is shown in FIGS. 55-64. Guide 600 includes a base component 602 that is sized and configured to support an arm component 620 such that arm component 620 may be moved relative to base component 602. Base component 602 extends from a leading end 604 to a trailing end 606. Base component 602 defines one or more holes 608-1, 608-2 (collectively, "holes 608") each being sized and configured to receive a fixation element, such as a pin or k-wire, therethrough for securing the base component 602 to a bone as illustrated in FIG. 55. Trailing end 606 includes a beam 610 extending upwardly away from leading end 604 of base component 602. In some embodiments, beam 610 includes one or more stops 612-1, 612-2 (collectively, "stops 612") extending from planar surface 611 of beam 610 and includes one or more tenons or projections 614-1, 614-2 (collectively, "projections 614") as best seen in FIG. 60. Beam 610 may also include a cutout 616 sized and configured to receive arm component 620 as described below. Base component may also define a hole 618 for additional fixation into the bone.

As best seen in FIGS. 61-64, arm component 620 extends from a coupling end 622 to another end 624. Coupling end 622 defines a mortise or recess 626 sized and configured to engage beam 610 and projections 614. For example, in some embodiments, the combination of projections 614 and recess 626 form a dovetail or tenon-mortise connection or joint that enables arm component 620 to move, such as by sliding, relative to base component 602 along beam 610 and projections 614. In some embodiments, arm component 620 includes a pair of opposed tapers 628-1, 628-2 (collectively, "tapers 628") along its length between coupling end 622 and end 624. Tapers 628 may be provided to facilitate gripping or enhanced ergonomics when arm component 620 is manipulated by a physician or other practitioner or user.

A guide hole 630 extends from a first side 632 of arm component 620 to a second side 634 of arm component 620. As best seen in FIG. 55, guide hole 630 is arranged such that a central axis defined by guide hole 630 is arranged perpendicularly with respect to a longitudinal axis defined by beam 610. Guide hole 630 is sized and configured to receive a shaft of a cutting tool, such as a reamer.

In use, guide 600 is placed on a bone as shown in FIG. 55. For example, in some embodiments, the base component 602 of guide 600 is placed on a flat formed on a superior portion of a talus. One or more fixation elements, such as k-wires or pins, are inserted through holes 608 to secure the base component to the bone. The arm component 620 may be coupled to the base component 602 by aligning the coupling end 622 of arm component 620 with cutout 616 defined by beam 610. When aligned, the dovetail/tenon-mortise connection between arm component 620 and base component 602 may be formed as will be understood by one of ordinary skill in the art.

Figure 65:
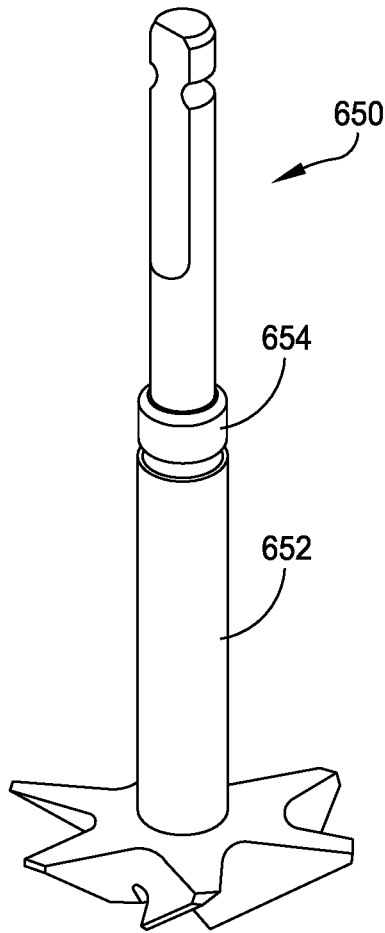
FIG. 65 is an isometric view of one example of a cutting tool in accordance with some embodiments.
Figure 66:
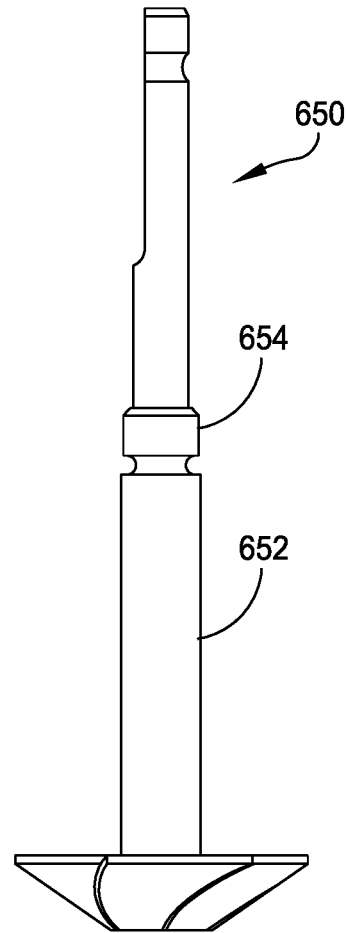
FIG. 66 is a side view of the cutting tool illustrated in FIG. 65 in accordance with some embodiments.
Figure 67:
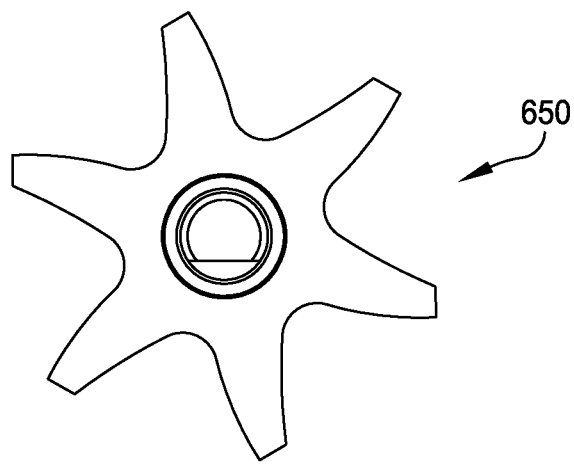
FIG. 67 is a top side view of the cutting tool illustrated in FIG. 65 in accordance with some embodiments.
Figure 71:
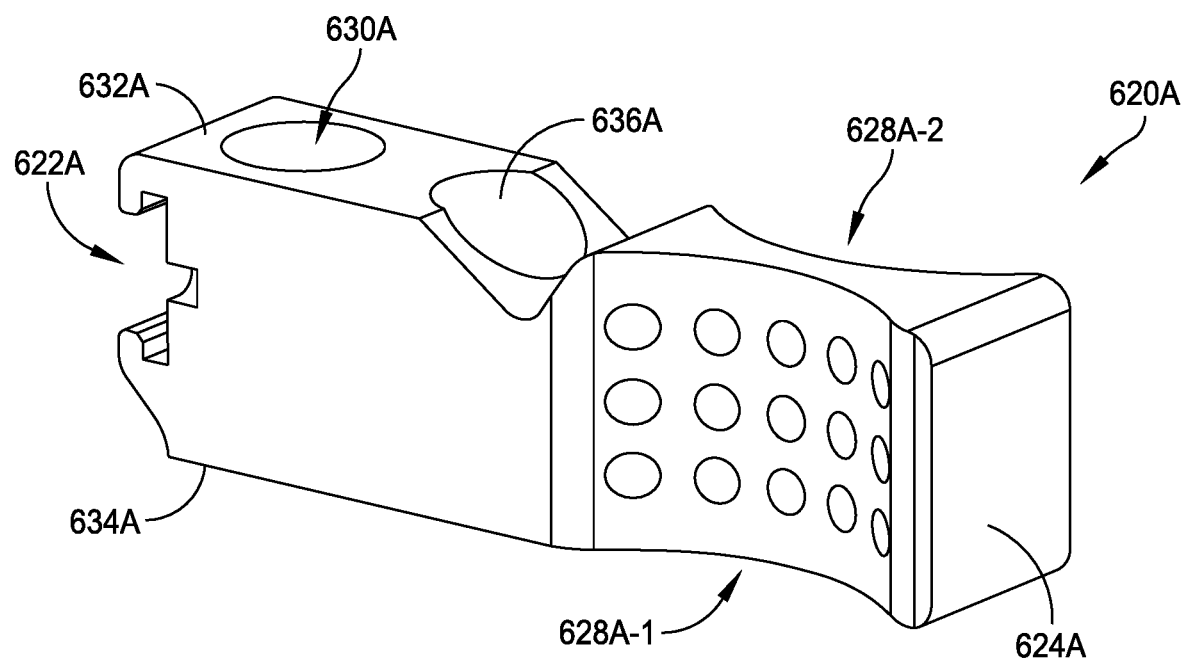
FIG. 71 is an isometric view of another example of an arm component of the cutting guide illustrated in FIG. 55 in accordance with some embodiments.
Figure 72:
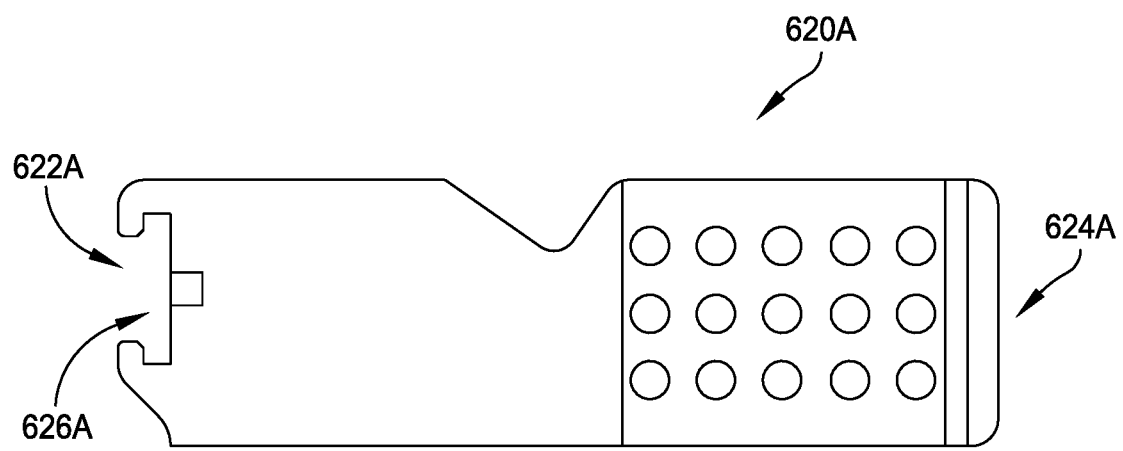
FIG. 72 is a side view of the arm component illustrated in FIG. 71 in accordance with some embodiments.
Figure 73:
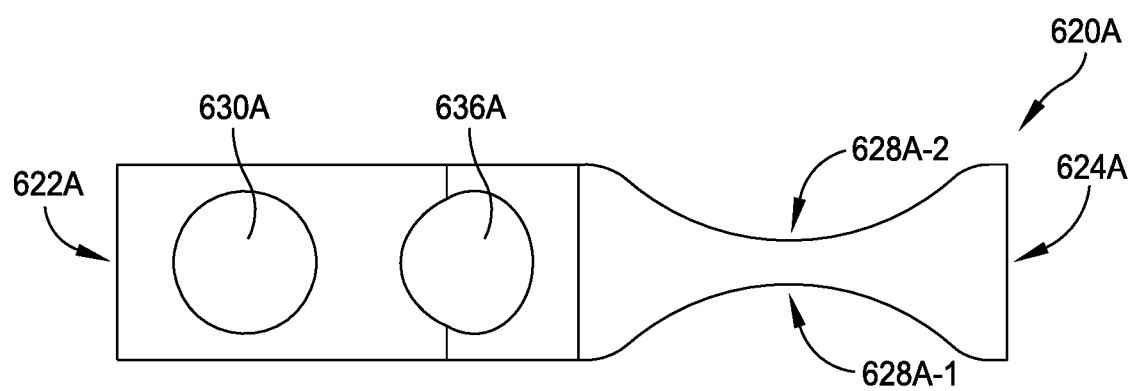
FIG. 73 is a top side view of the arm component illustrated in FIG. 71 in accordance with some embodiments.
Figure 74:
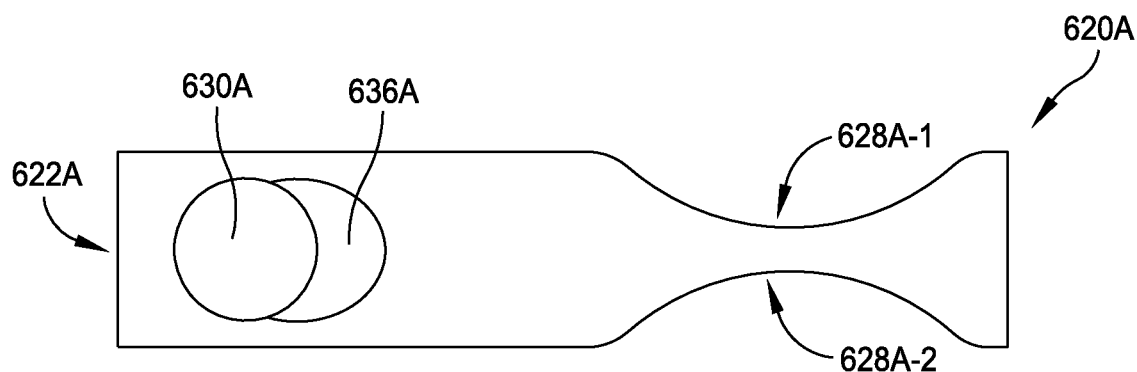
FIG. 74 is a bottom side view of the arm component illustrated in FIG. 71 in accordance with some embodiments.
Figure 75:
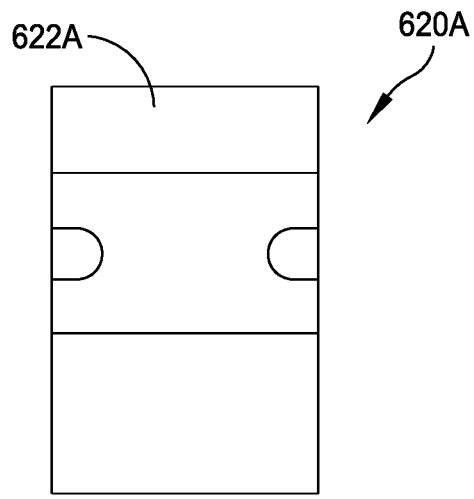
FIG. 75 is an end view of the arm component illustrated in FIG. 71 in accordance with some embodiments.
Figures 76, 77:
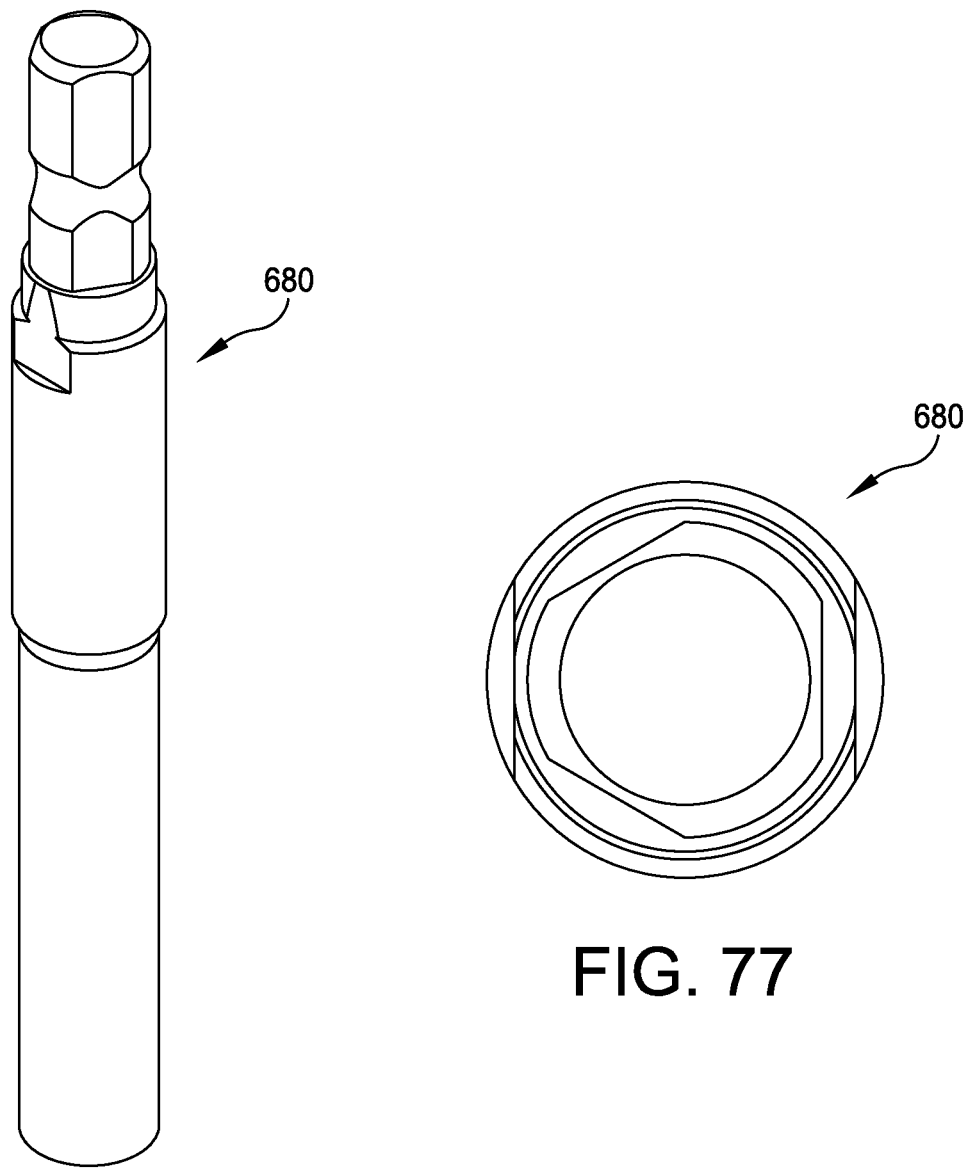
FIG. 76 is an isometric view of one example of a cutting tool in accordance with some embodiments.
FIG. 77 is a top side view of the cutting tool illustrated in FIG. 76 in accordance with some embodiments.
Figure 78:
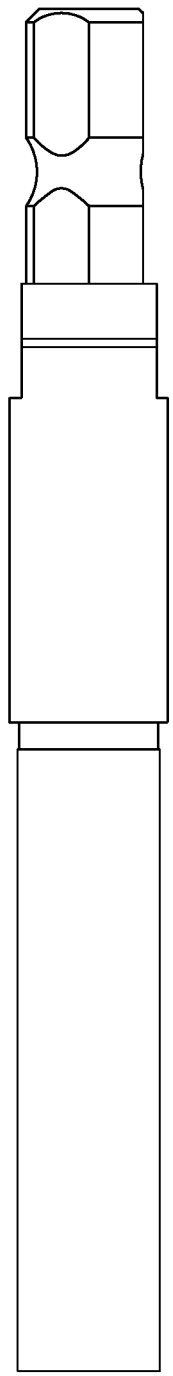
FIG. 78 is a side view of the cutting tool illustrated in FIG. 76 in accordance with some embodiments.
Figure 79:
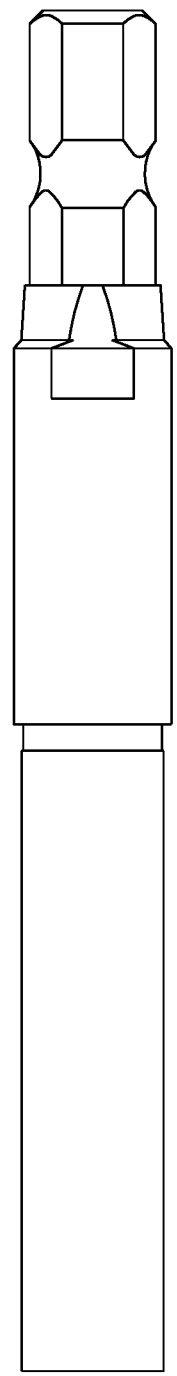
FIG. 79 is another side view of the cutting tool illustrated in FIG. 76 in accordance with some embodiments.

With the guide 600 secured to bone, bony cuts may be made to form a chamfer or chamfers. For example, a cutting instrument, such as the angled cutting instrument 650 illustrated in FIGS. 65-67, is coupled to the guide 600 by inserting a shaft 652 of the cutting instrument 650 into the guide hole 630 defined by arm component 620. The cutting instrument may be secured to the arm component via a nut, such as nut 670 illustrated in FIGS. 68-70, by threading the nut 670 onto threaded section 654 of shaft 652 of cutting instruction 650. The cutting tool is guided through making bony cuts as the surgeon or practitioner may grasp the arm component 620 via the tapers 628 and move the arm component 620 relative to the base component 602 by sliding arm component 620 along beam 610 from stop 612-1 to stop 612-2.

In some embodiments, the arm component 620 of guide 600 may be swapped out for another arm component, such arm component 620A shown in FIGS. 71-75, to perform the anterior chamfer and flat cuts on the talus instead of arm component 620. As shown FIGS. 71-75, arm component 620A extends from a coupling end 622A to another end 624A. Coupling end 622A defines a mortise or recess 626A sized and configured to engage beam 610 and projections 614. For example, in some embodiments, the combination of projections 614 and recess 626A form a dovetail or tenon-mortise connection or joint that enables arm component 620A to move, such as by sliding, relative to base component 602 along beam 610 and projections 614. In some embodiments, arm component 620A includes a pair of opposed tapers 628A-1, 628A-2 (collectively, "tapers 628A") along its length between coupling end 622A and end 624A. Tapers 628A may be provided to facilitate gripping or enhanced ergonomics when arm component 620A is manipulated by a physician or other practitioner or user.

A guide hole 630A extends from a first side 632A of arm component 620A to a second side 634A of arm component 620A. Guide hole 630A is arranged such that a central axis defined by guide hole 630A is arranged perpendicularly with respect to a longitudinal axis defined by beam 610. A second guide hole 636A is defined by arm component 620A. Guide hole 636A is disposed at an angle relative to guide hole 630A. As described in greater detail below, the angle at which guide hole 636A is oriented relative to guide hole 630A facilitates making the anterior flat cut. Both guide holes 630A and 636A are sized and configured to receive a shaft of a cutting tool, such as reamer 680 illustrated in FIGS. 76-79.

Arm component 620 may be removed by uncoupling the cutting tool, e.g., cutting tool 650, from its engagement with arm component 620, which may include unscrewing nut 670. With cutting tool 650 uncoupled from arm component 620, arm component 620 may be uncoupled from base component 602 by aligning arm component 620 with the cutout 616 of beam 610 and rotating arm component 620 such that it disengages beam 610. In some embodiments, arm component 620A may be coupled to base component 602 instead of arm component 620 by aligning coupling end 622A with cutout 616 of beam 610 and engaging the coupling end 622A with projections 614 and beam 610.

Figure 80:
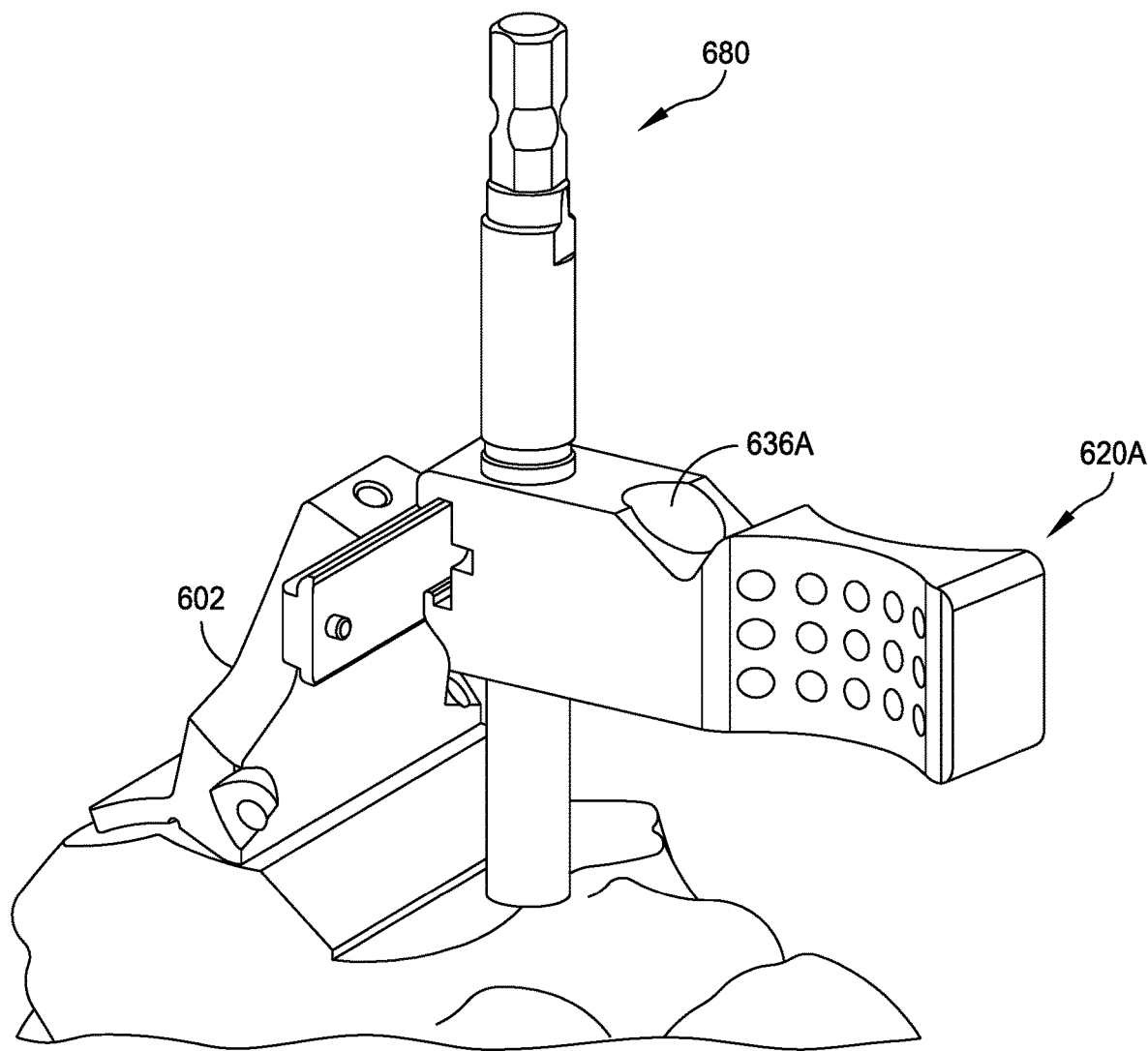
FIG. 80 illustrates one example of a cutting guide being used to perform a cut in accordance with some embodiments.
Figure 81:
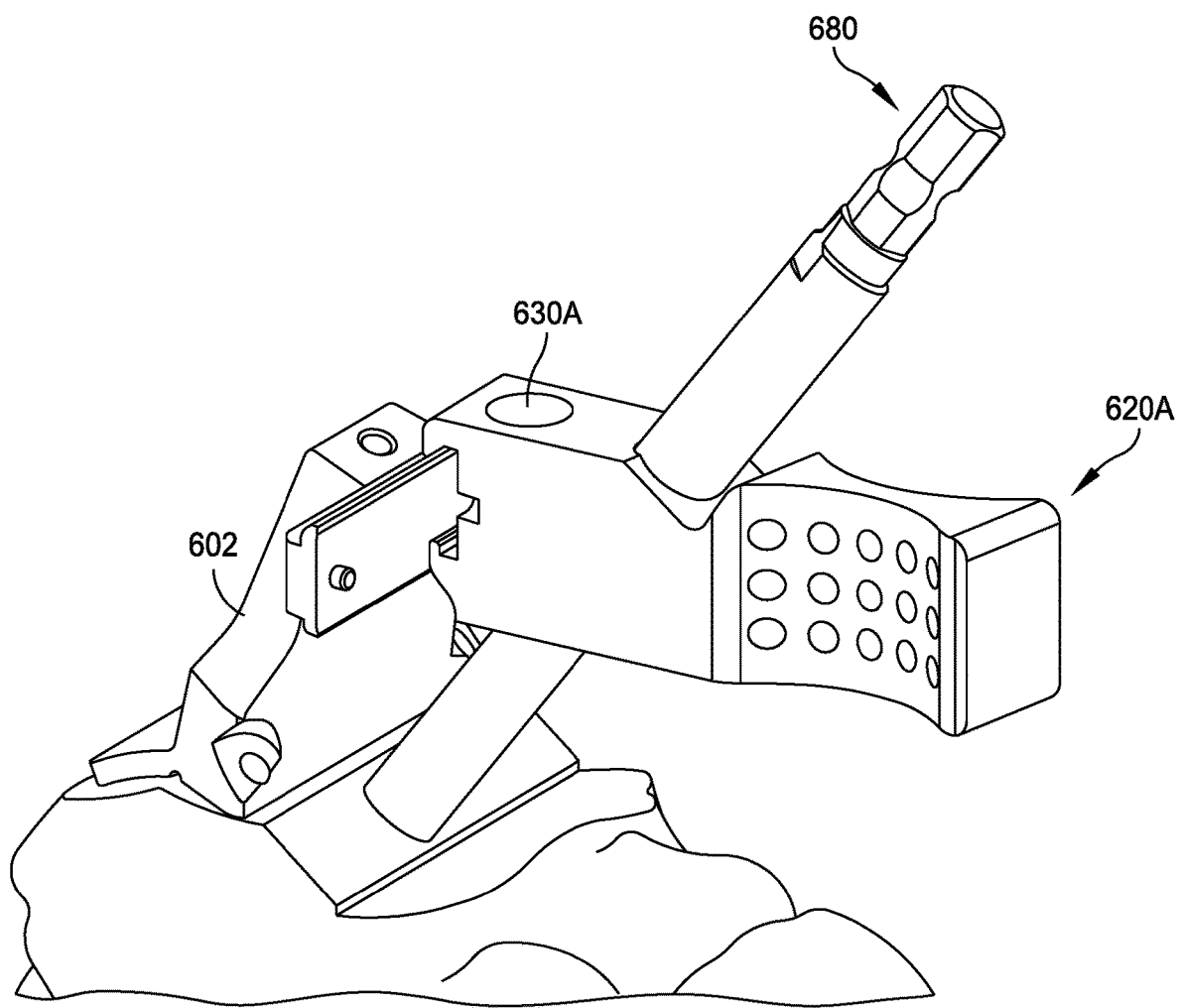
FIG. 81 illustrates one example of a cutting guide being used to perform another cut in accordance with some embodiments.

A cutting tool, such as reamer 680, may then be inserted into hole 630A such that a first cut may be performed. The reamer 680 may be guided in making the first cut by sliding arm 620A along beam 610 from stop 612-1 to stop 612-2 as illustrated in FIG. 80. The reamer 680 may then be removed from hole 630A and inserted into hole 636A to make a second cut as illustrated in FIG. 81.

Once the cuts have been made using guide 600, the fixation elements may be removed from their engagement with the guide 600 and bone, and then the guide 600 may be removed from its contact with the bone.

Anterior Referencing Chamfer Guides

FIGS. 82-107 illustrate a series of guides that may be used with anterior referencing to make both anterior chamfer cuts and posterior chamfer cuts. Referring first to FIGS. 82-87, guide base 702 includes a planar bottom surface 704 for mating to a flat formed on a bone and defines one or more holes 708-1, 708-2 (collectively, "holes 708"). Upper portion 706 of base 702 includes a beam 710, which may be similar to beam 610 described above in that beam 710 may include stops 712-1, 712-2 (collectively, "stops 712"), projections 714-1, 714-2 (collectively, "projections 714"), and a cutout 716.

Figure 82:
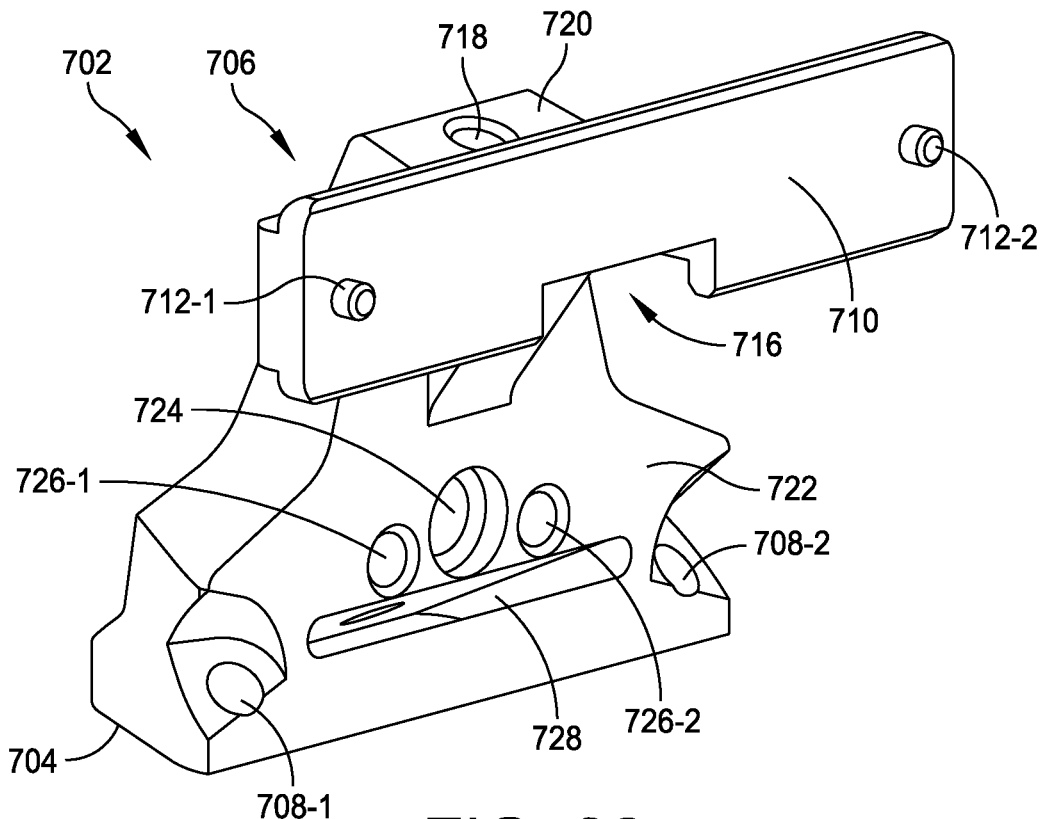
FIG. 82 is an isometric view of another example of a cutting guide base in accordance with some embodiments.
Figure 83:
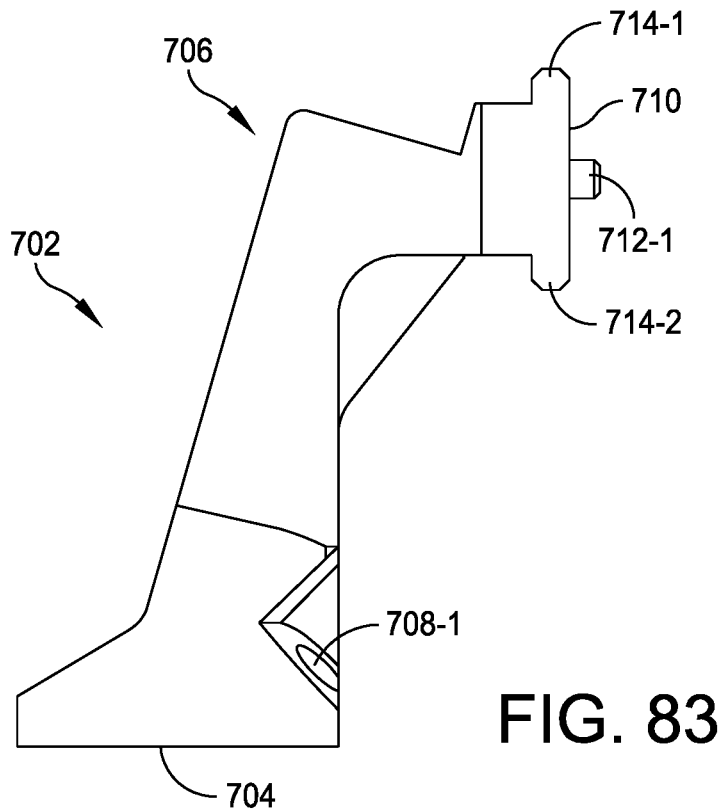
FIG. 83 is a side view of the cutting guide base illustrated in FIG. 82 in accordance with some embodiments.
Figure 87:
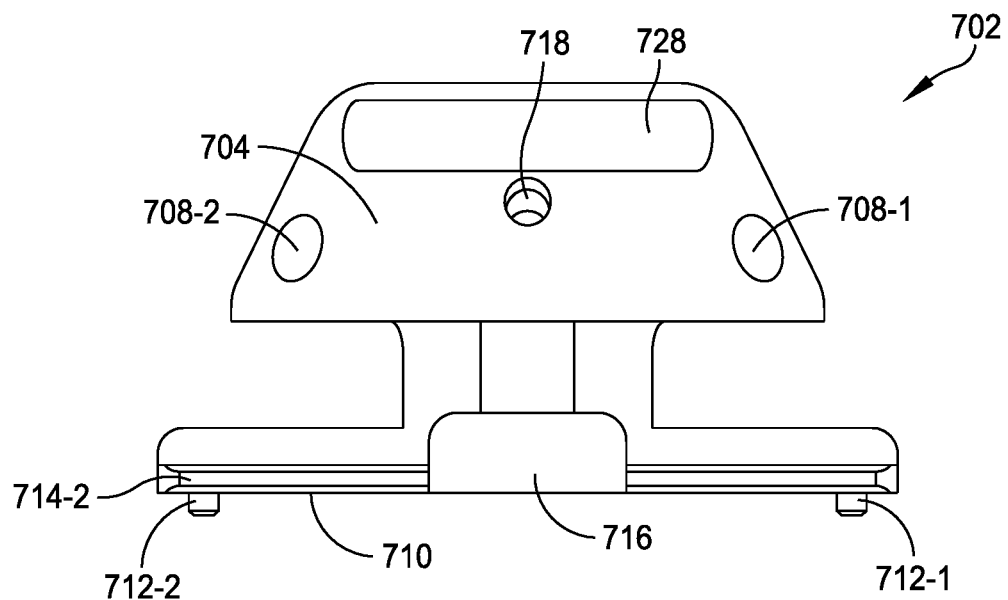
FIG. 87 is a bottom side view of the cutting guide base illustrated in FIG. 82 in accordance with some embodiments.
Figure 88:
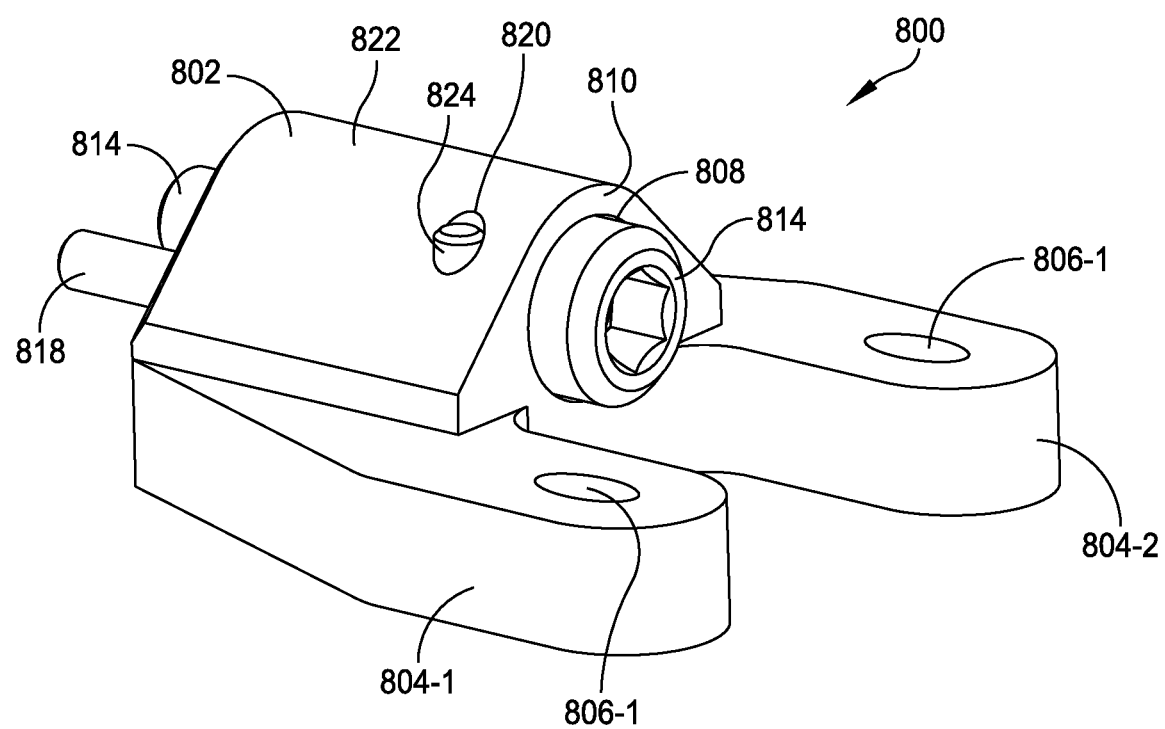
FIG. 88 is an isometric view of one example of a locator guide in accordance with some embodiments.
Figure 89:
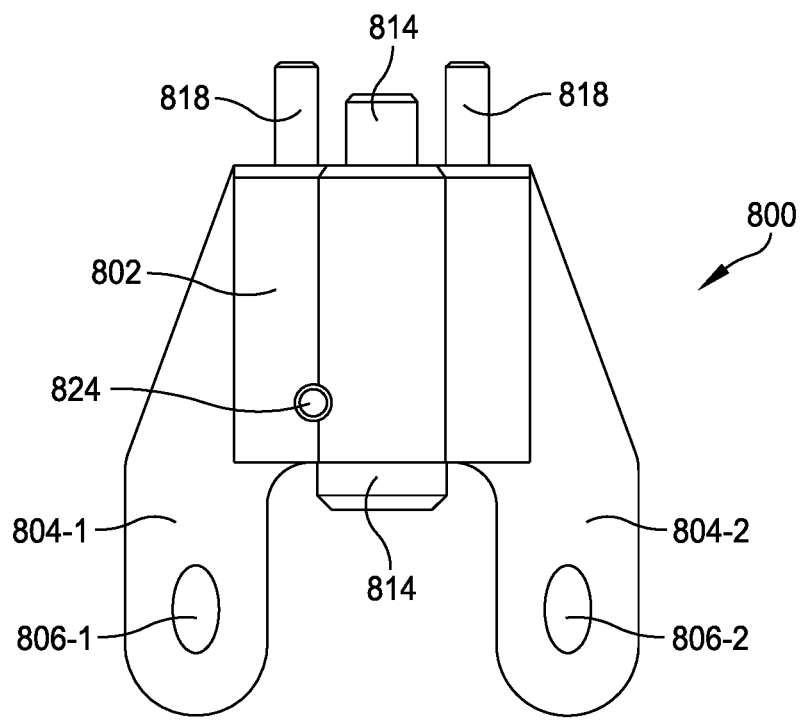
FIG. 89 is a top side view of the locator guide illustrated in FIG. 88 in accordance with some embodiments.
Figure 90:
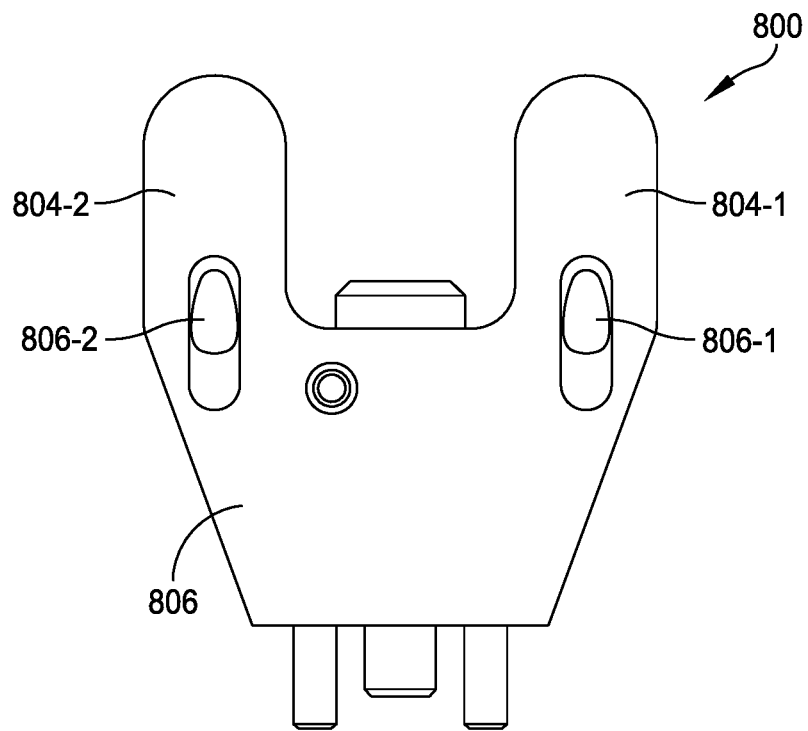
FIG. 90 is a bottom side view of the locator guide illustrated in FIG. 88 in accordance with some embodiments.
Figure 91:
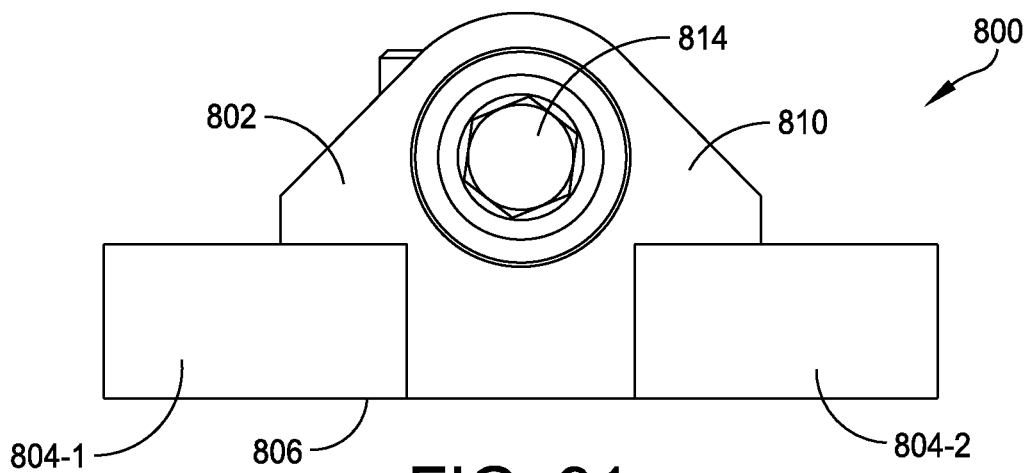
FIG. 91 is a front side view of the locator guide illustrated in FIG. 88 in accordance with some embodiments.

Base 702 defines a hole 718 extending from upper surface 720 to lower surface 704. Surface 722 of base 702 defines a central hole 724 and two adjacent holes 726-1, 726-2 (collectively, "holes 726"). Holes 726 are sized and configured to receive dowels as will be described in greater detail below. A slot 728 is defined by base 702 and extends at an angle from surface 722 to bottom surface 704 as best seen in FIGS. 82 and 87.

FIGS. 88-93 illustrate one example of a locator guide 800 that may be used to position guide base 702. Locator guide 800 includes a body 802 including a pair of spaced apart legs 804-1, 804-2 (collectively, "legs 804"). Each leg 804-1, 804-2 defines a respective hole 806-1, 806-2 (collectively, "holes 806") each sized and configured to receive a fixation element, such as a k-wire or pin, for securing the locator guide 800 to bone.

Figure 92:
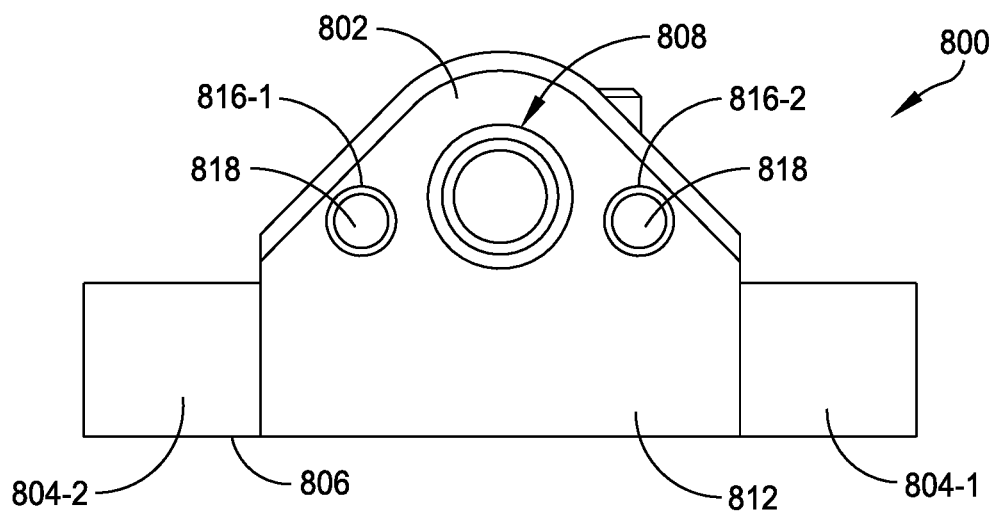
FIG. 92 is a rear side view of the locator guide illustrated in FIG. 88 in accordance with some embodiments.
Figure 93:
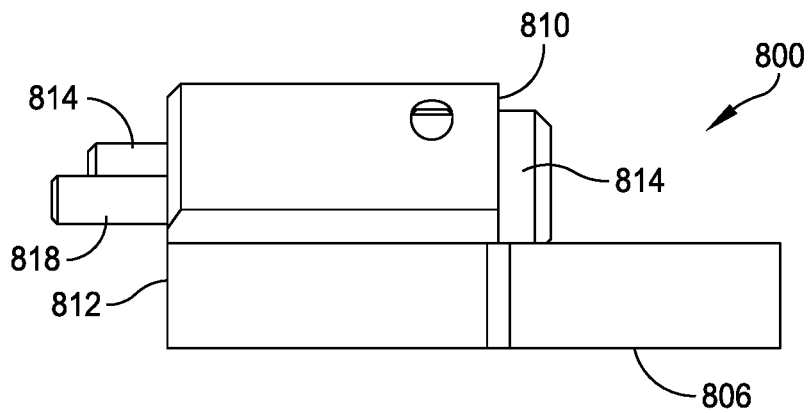
FIG. 93 is a side view of the locator guide illustrated in FIG. 88 in accordance with some embodiments.

Bottom surface 806 of body 802 may be planar to facilitate positioning locator guide 800 on a flat formed on a bone, such as a talus. Body 802 defines a through hole 808 extending from surface 810 disposed between legs 804 to rear surface 812. Hole 808 is sized and configured to receive an adjustment bolt 814 therein in a threaded engagement as will be understood by one of ordinary skill in the art. As best seen in FIG. 92, rear surface 812 also defines a pair of blind holes 816-1, 816-2 (collectively, "holes 816" or "blind holes 816") that extend inwardly from surface 812 and are sized and configured to receive a respective dowel pin 818 therein. In some embodiments, body 802 may define a hole 820 extending from top surface 822 to bottom surface 806. Hole 820 is sized and configured to receive a dowel pin 824 therein.

Figure 84:
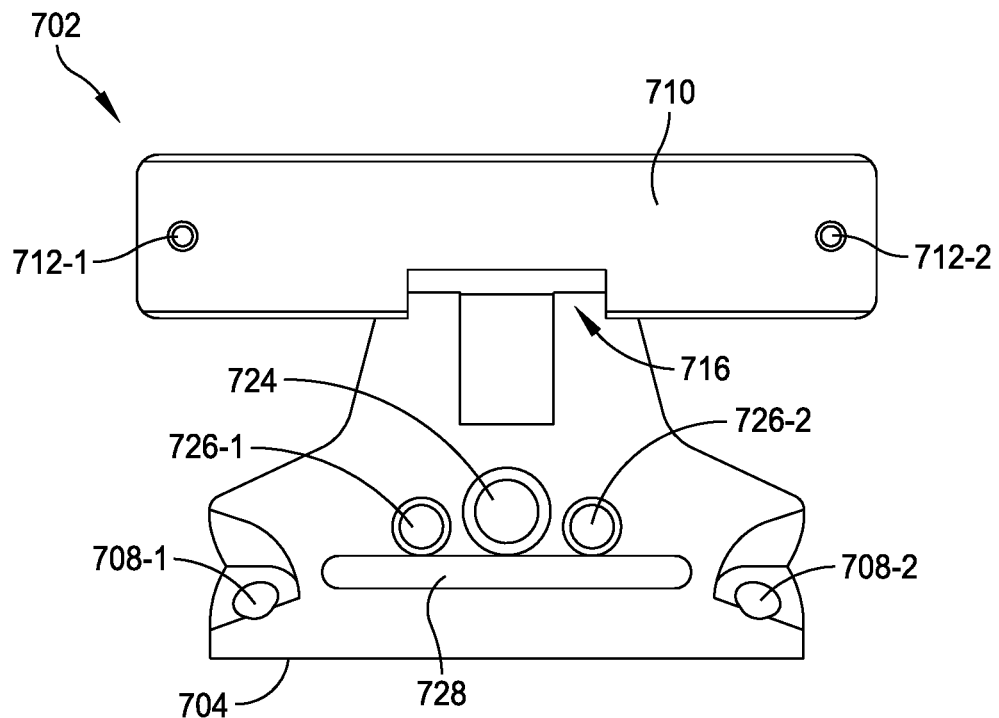
FIG. 84 is a front side view of the cutting guide base illustrated in FIG. 82 in accordance with some embodiments.
Figure 85:
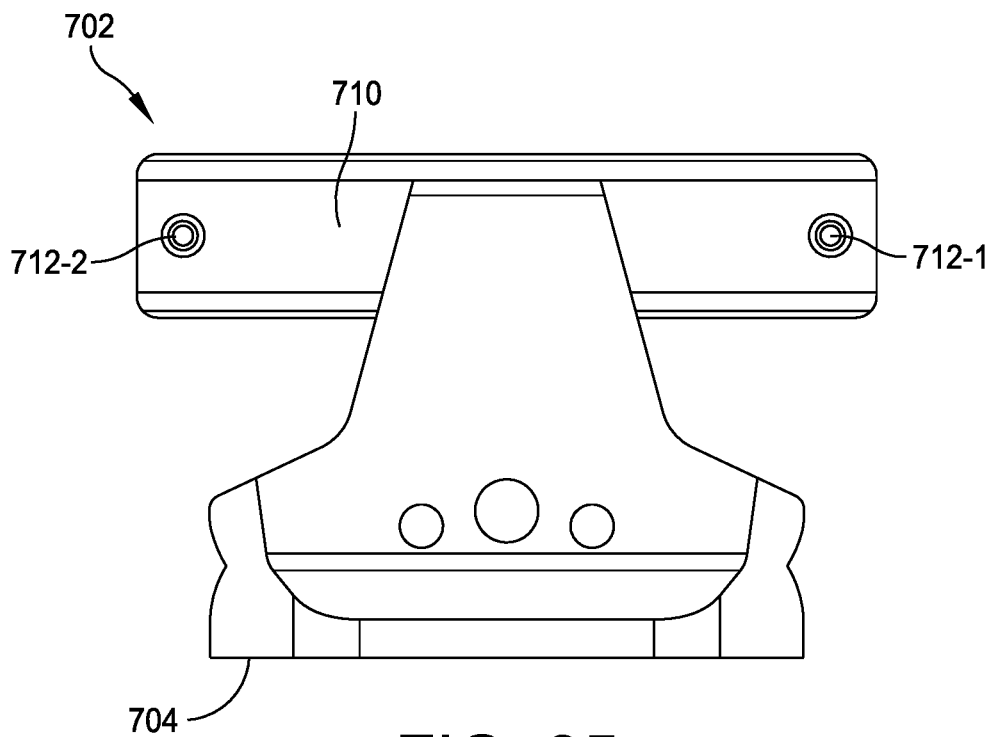
FIG. 85 is a rear side view of the cutting guide base illustrated in FIG. 82 in accordance with some embodiments.
Figure 86:
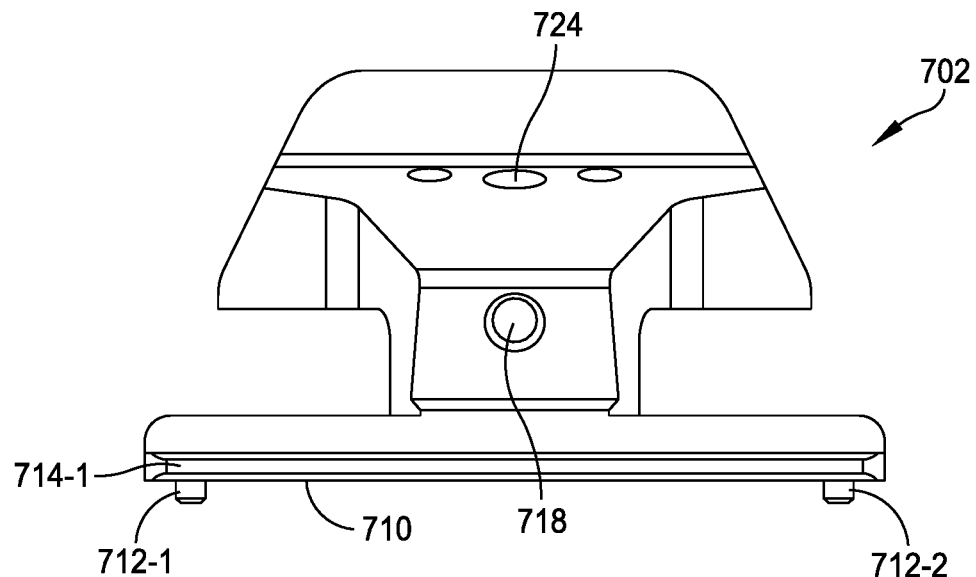
FIG. 86 is a top side view of the cutting guide base illustrated in FIG. 82 in accordance with some embodiments.

Locator guide 800 may be used to position guide base 702, which is shown in FIG. 84. More particularly, dowels 818 extending from guide 800 may be inserted into holes 726 defined by guide base 702. With dowels 818 positioned within holes 726, hole 808 is aligned with hole 724 and bolt 814 is used to assemble locator guide 800 to guide base 702. Fixation elements may be inserted into holes 806 defined by legs 804 of locator guide 800.

With guide base 702 properly positioned, fixation elements may be inserted into the holes 708 defined by guide base 702 to secure guide base to the bone. The locator guide 800 may then be removed from its engagement with guide base 702 and the bone as will be understood by one of ordinary skill in the art. An arm component, such as arm component 620 or arm component 620A, may then be coupled to guide base 702 in the same manner to facilitate making anterior chamfer cuts as described above with respect to cutting guide 600.

Figure 94:
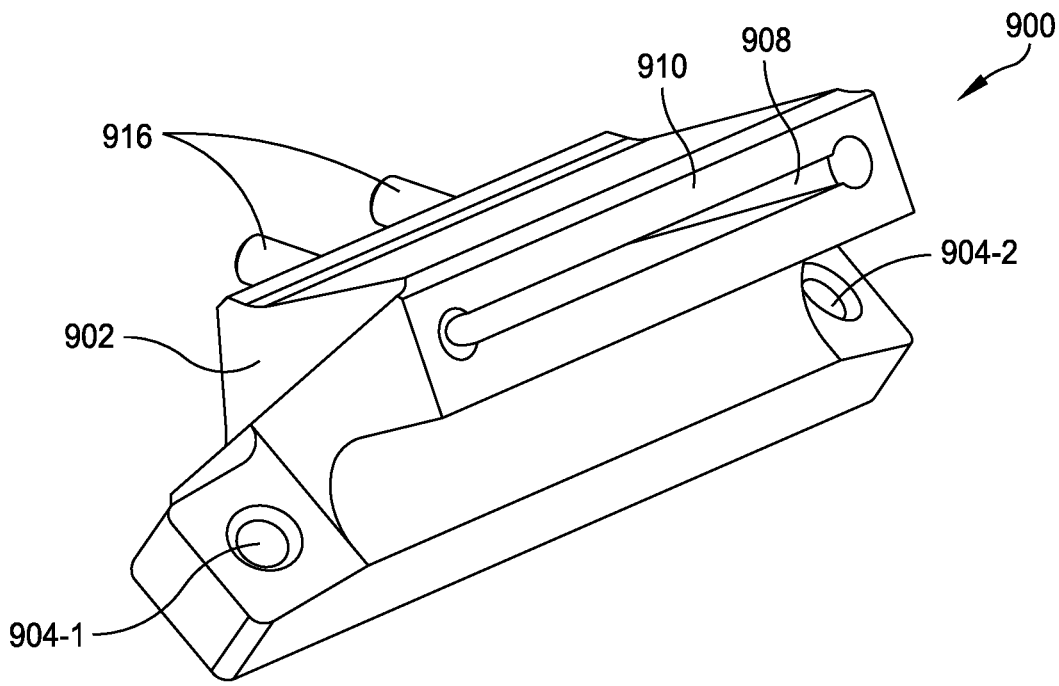
FIG. 94 is an isometric view of a cutting guide in accordance with some embodiments.
Figure 95:
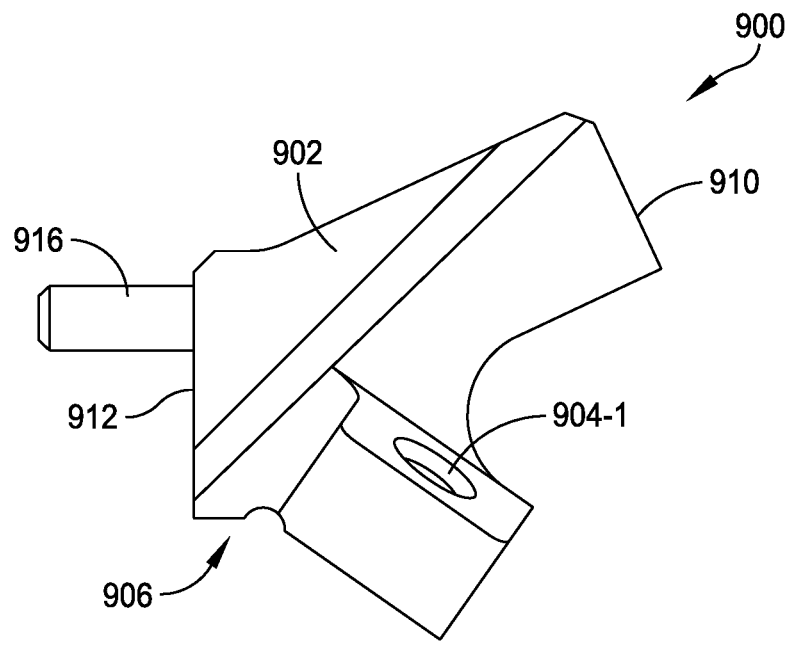
FIG. 95 is a side view of the cutting guide illustrated in FIG. 94 in accordance with some embodiments.

Guide base 702 may also be used in making posterior chamfer cuts. For example, FIGS. 94-99 illustrate one example of a posterior cutting guide 900 that may be used with guide base 702 to form a posterior chamfer cut. Referring first to FIG. 94, cutting guide 900 includes a body 902 defining one or more holes 904-1, 904-2 (collectively, "holes 904") for receiving fixation elements, such as k-wires or pins, to secure the cutting guide 900 to bone. As best seen in FIG. 95, the bottom surface 906 of cutting guide 900 may be angled to mate to a previously formed anterior chamfer.

Figure 96:
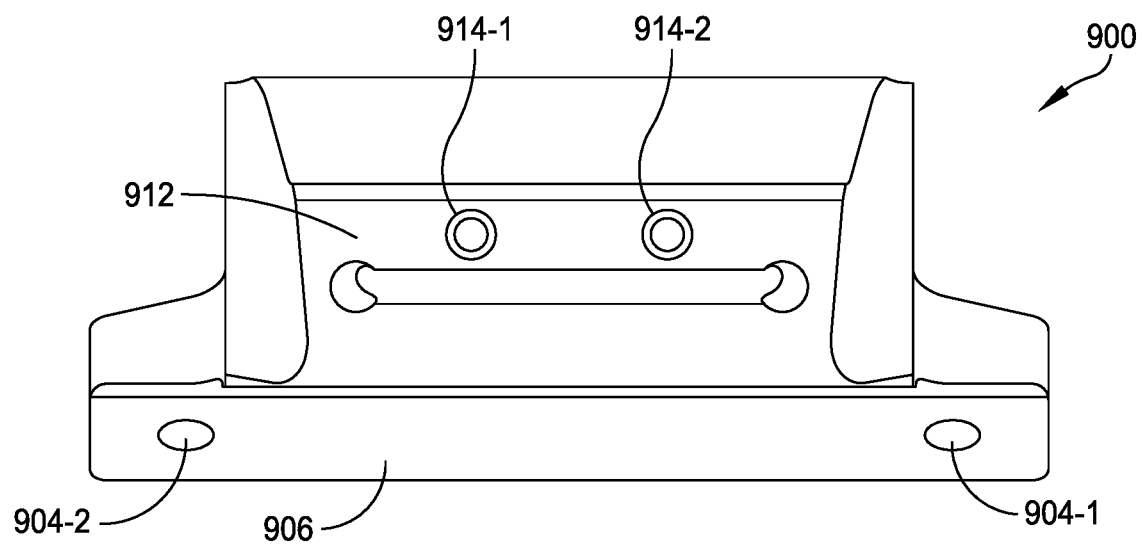
FIG. 96 is a front side view of the cutting guide illustrated in FIG. 94 in accordance with some embodiments.
Figure 97:
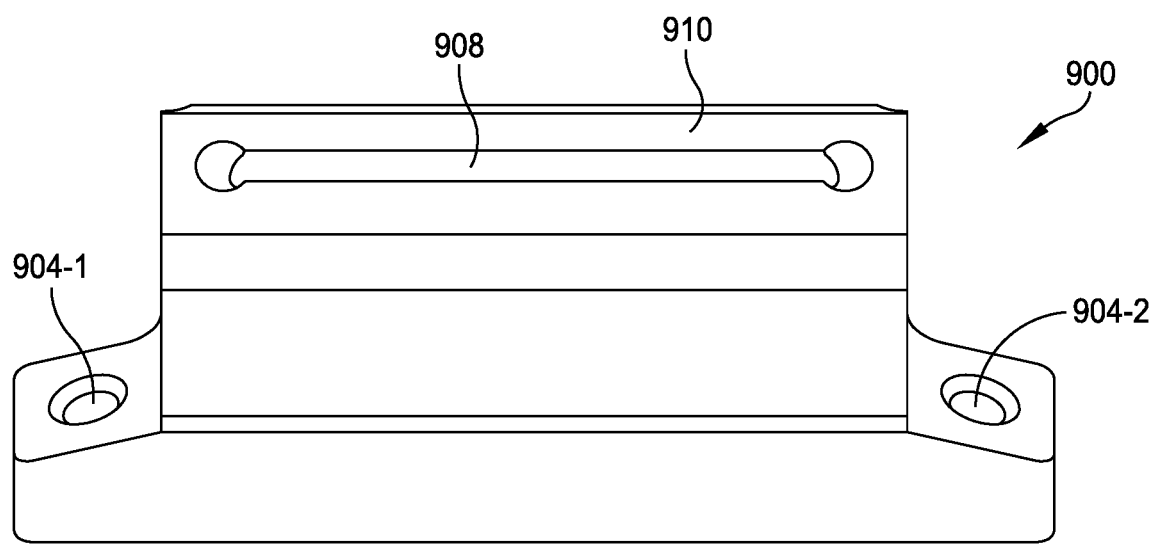
FIG. 97 is a rear side view of the cutting guide illustrated in FIG. 94 in accordance with some embodiments.
Figure 98:
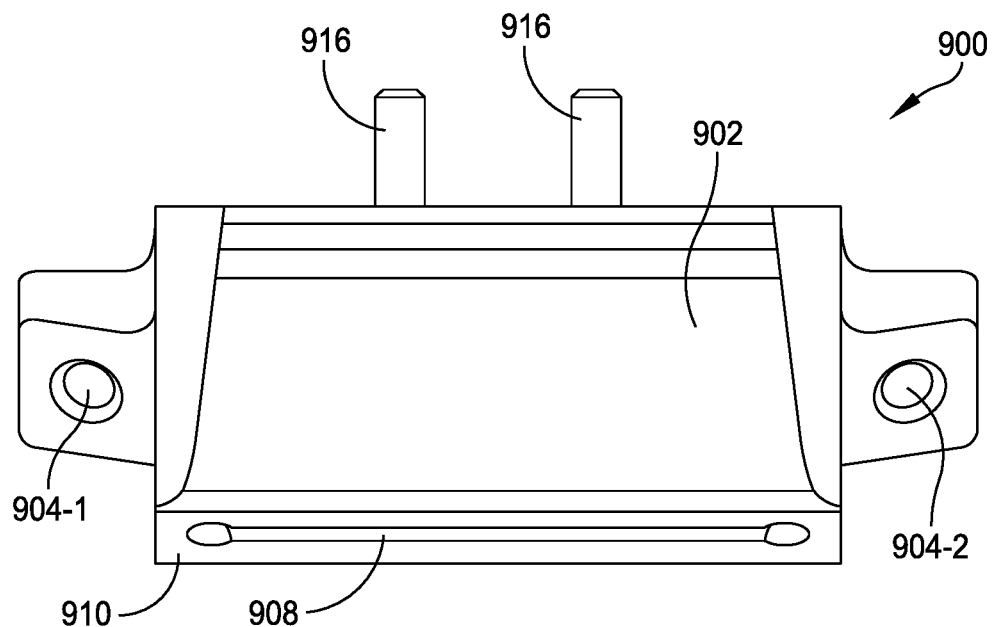
FIG. 98 is a top side view of the cutting guide illustrated in FIG. 94 in accordance with some embodiments.
Figure 99:
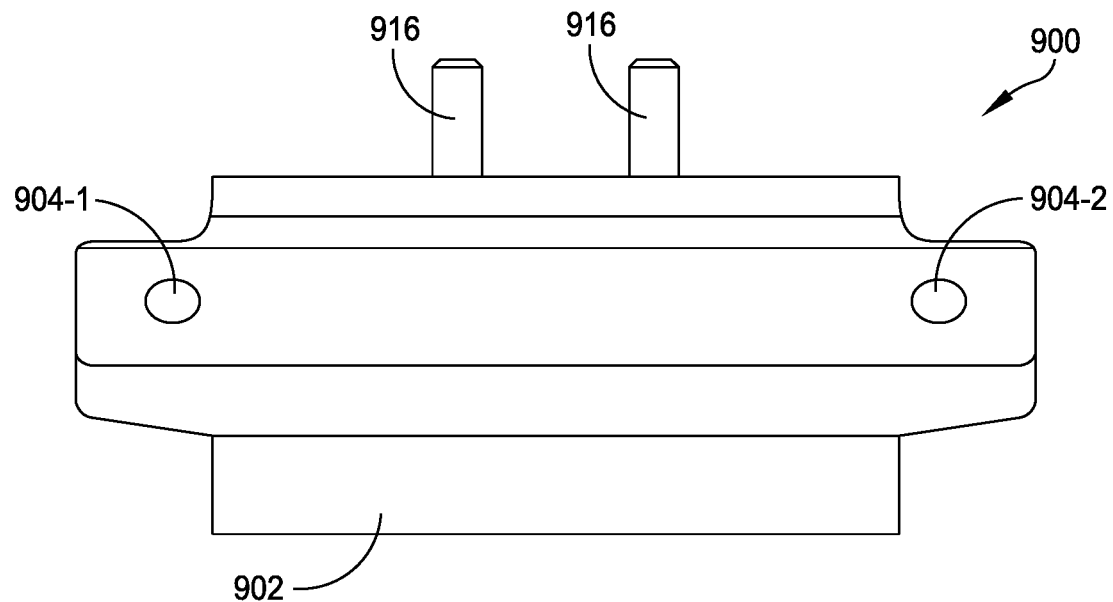
FIG. 99 is a bottom side view of the cutting guide illustrated in FIG. 94 in accordance with some embodiments.

Body 902 also defines a slot 908 extending from surface 910 to side 912. Side 912 also defines one or more holes 914-1, 914-2 (collectively, "holes 914") as shown in FIG. 96. Holes 914 may be blind holes extending inwardly from side 912 and being sized and configured to receive a dowel pin 916 as illustrated in FIGS. 94 and 95. Holes 914 are positioned on body 902 such that they align with holes 726 defined by guide base 702. Similarly, slot 908 extends through body 902 such that it aligns to slot 728 when dowels 916 are received within both 914 and holes 726.

Figure 100:
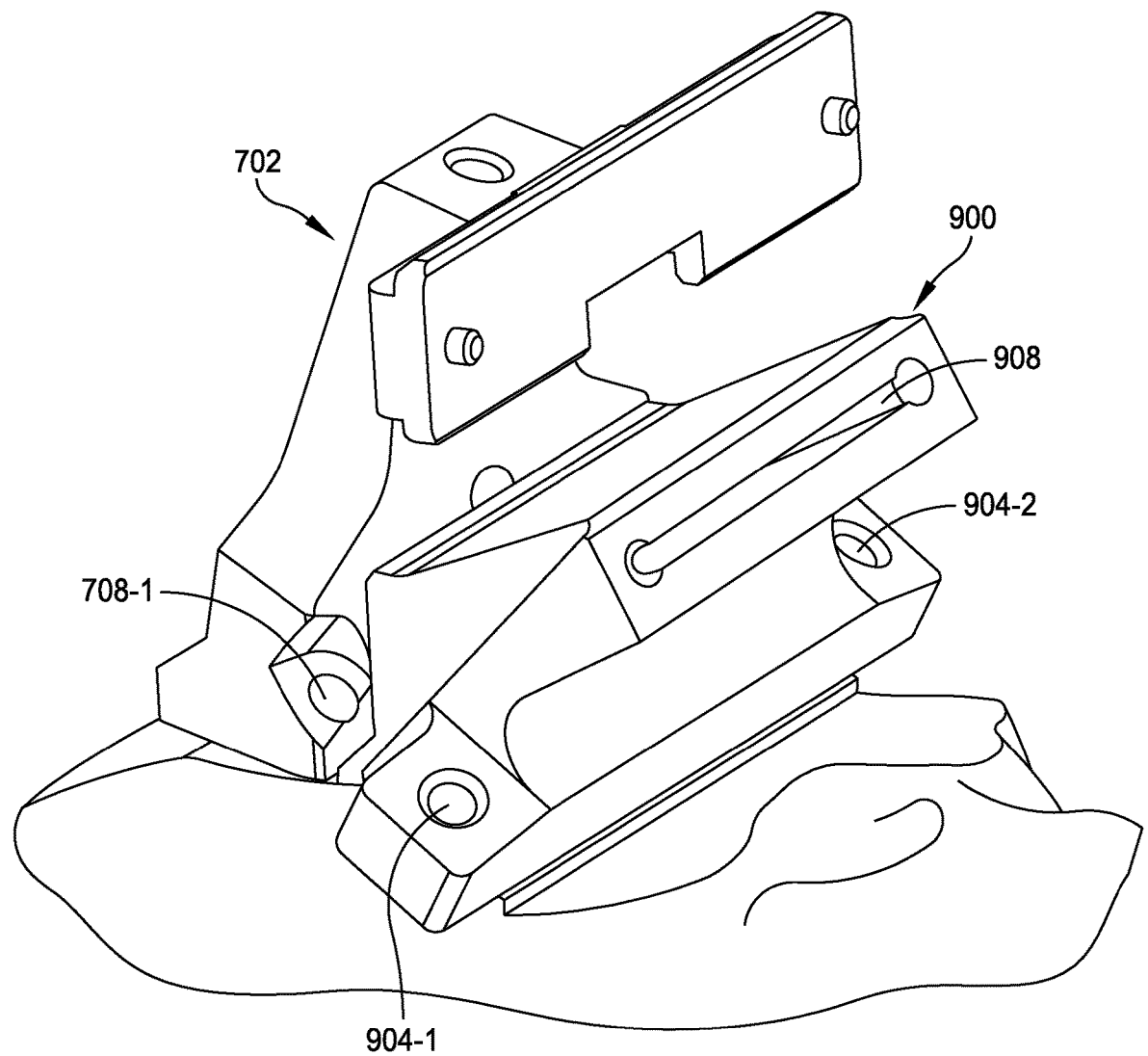
FIG. 100 illustrates one example of a posterior cutting guide being coupled to bone and to a cutting guide base in accordance with some embodiments.
Figure 101:
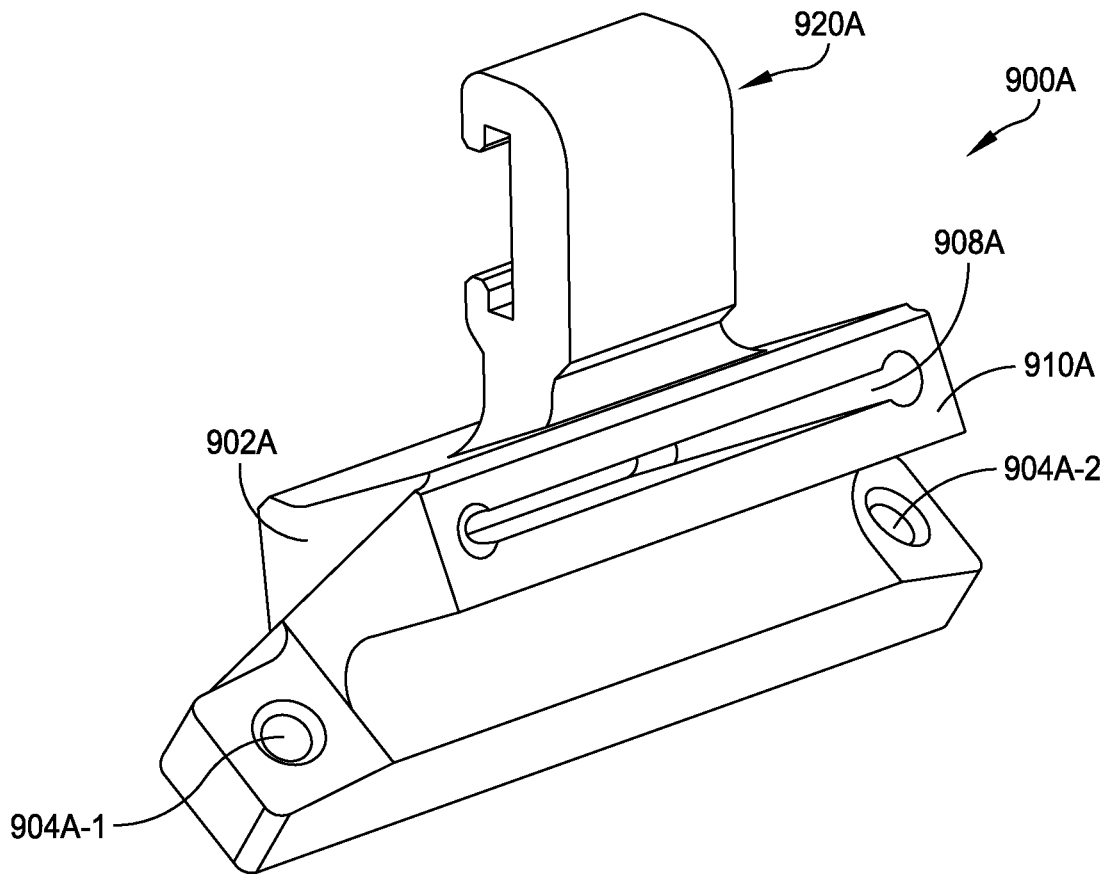
FIG. 101 is an isometric view of another example of a cutting guide in accordance with some embodiments.
Figure 102:
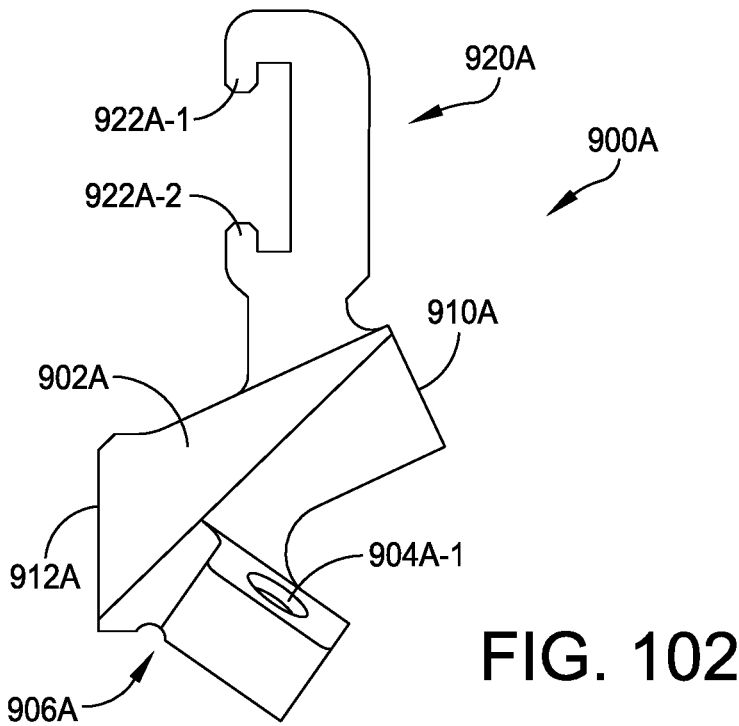
FIG. 102 is a side view of the cutting guide illustrated in FIG. 101 in accordance with some embodiments.
Figure 103:
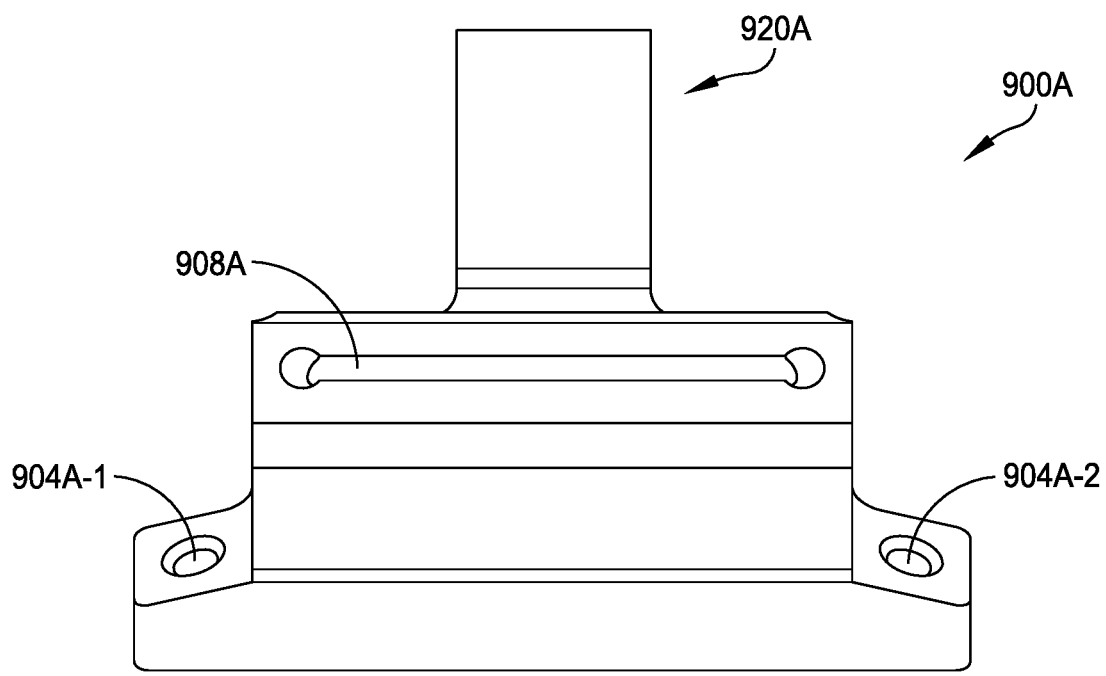
FIG. 103 is a front side view of the cutting guide illustrated in FIG. 101 in accordance with some embodiments.
Figure 104:
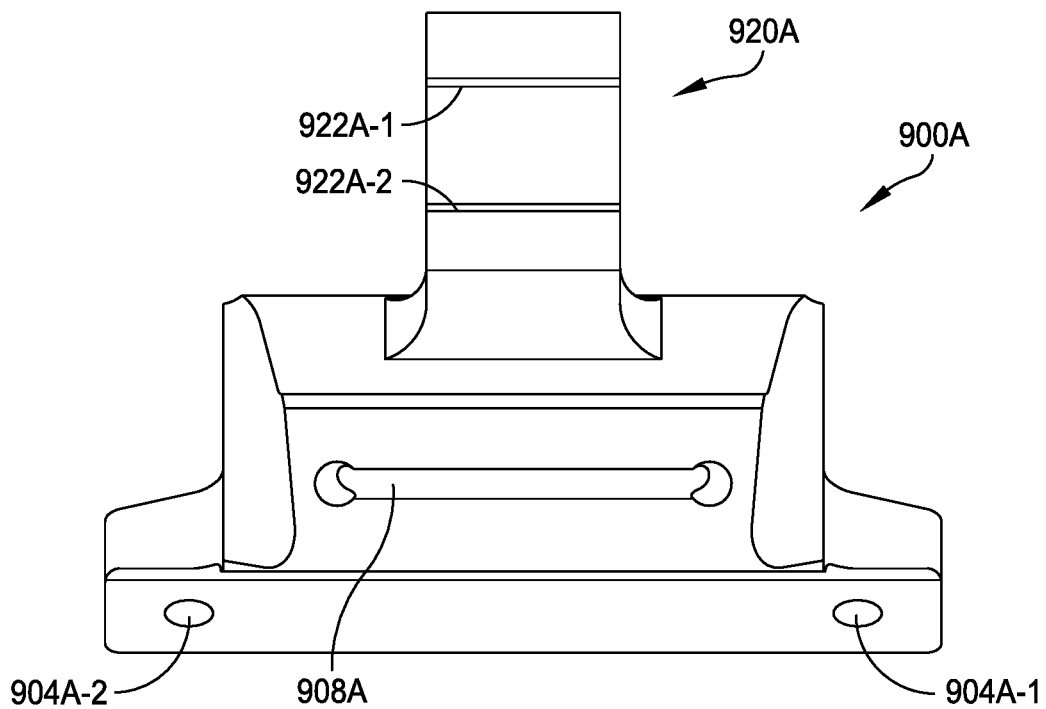
FIG. 104 is a rear side view of the cutting guide illustrated in FIG. 101 in accordance with some embodiments.
Figure 105:
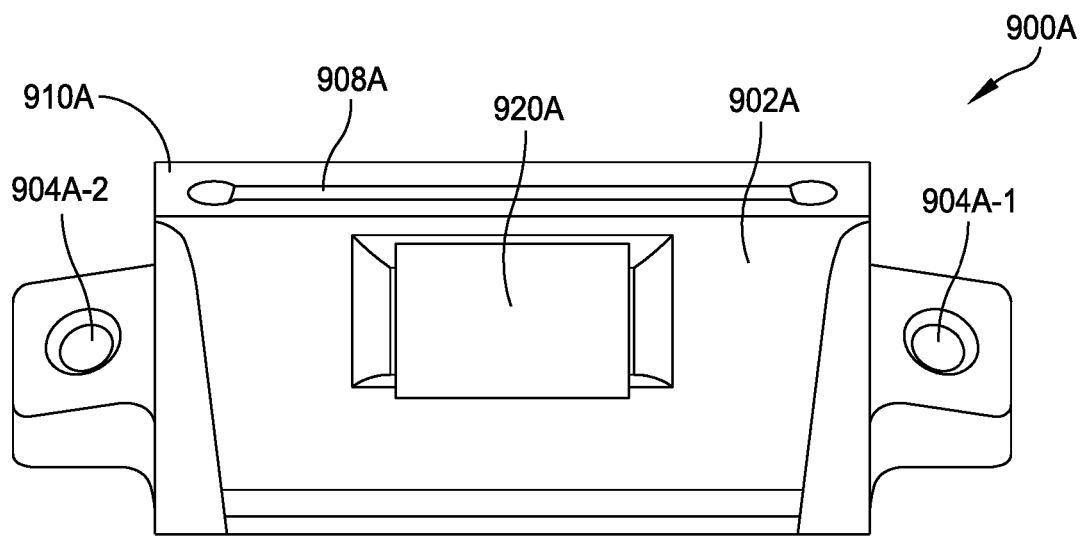
FIG. 105 is a top side view of the cutting guide illustrated in FIG. 101 in accordance with some embodiments.
Figure 106:
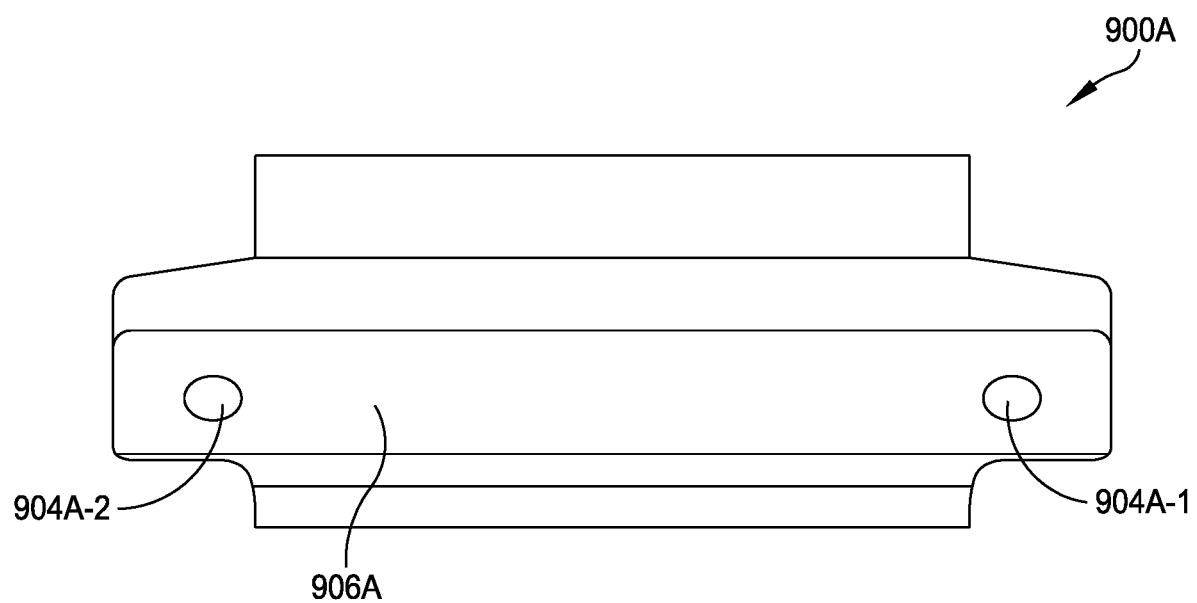
FIG. 106 is a bottom side view of the cutting guide illustrated in FIG. 101 in accordance with some embodiments.

FIG. 100 illustrates one example of guide base 702 being coupled to bone and cutting guide 900 being coupled to bone and to guide base 702. A posterior chamfer cut may be made by inserting a cutting tool, such as a bone saw or chisel, into and through slot 908 defined by cutting guide 900 and into and through slot 728 defined by guide base 702.

Another example of a posterior chamfer cutting guide is illustrated in FIGS. 101-106. Cutting guide 900A includes a body 902A defining at least one hole 904A-1, 904A-2 (collectively, "holes 904") sized and configured to receive a fixation element for securing the cutting guide 900A to bone. Like cutting guide 900, cutting guide 900A includes a bottom surface 906A that is angled to mate to a previously formed anterior chamfer. Body 902A also defines a slot 908A that extends from surface 910A to surface 912A.

Figure 107:
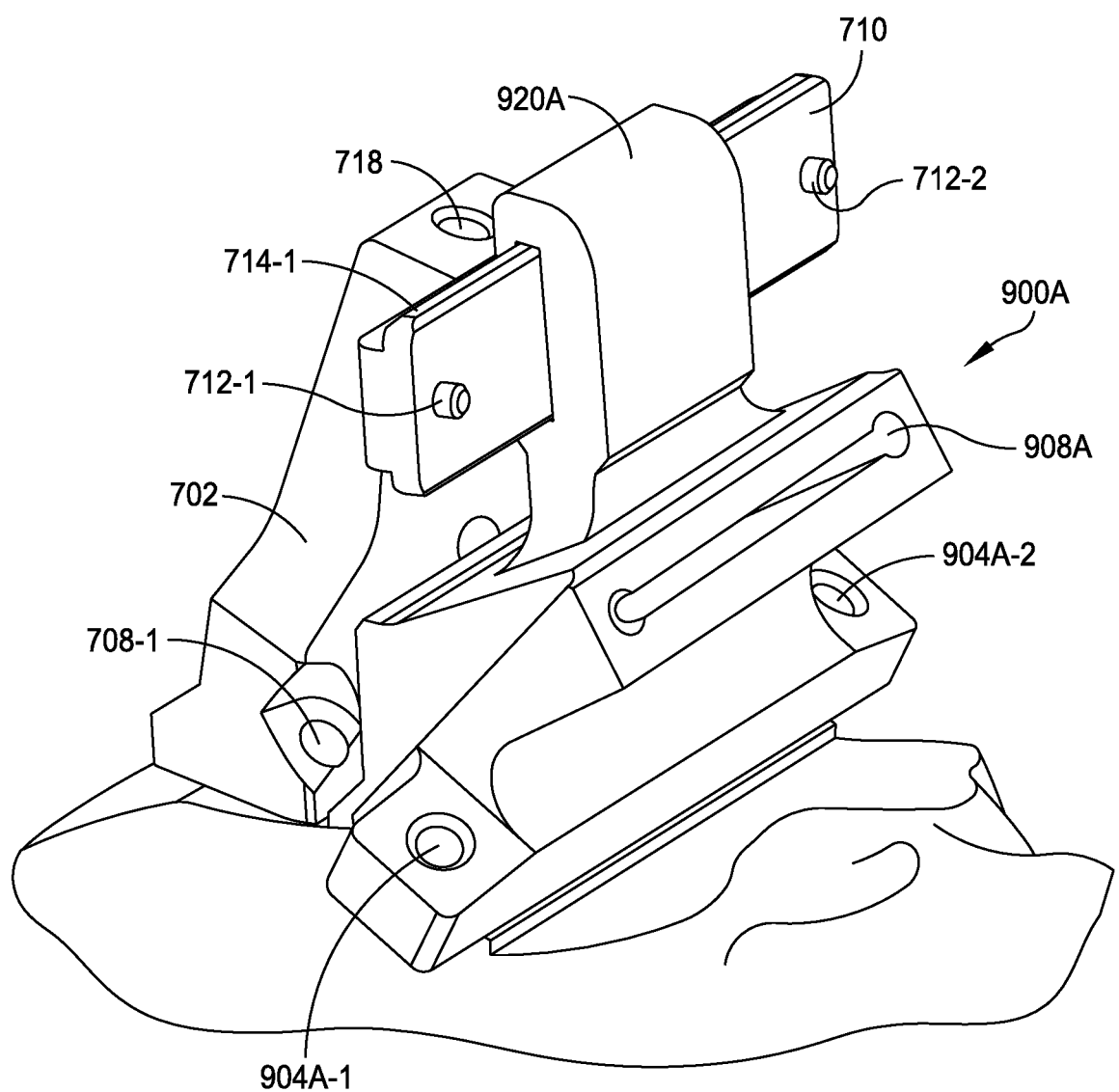
FIG. 107 illustrates one example of a posterior cutting guide being coupled to bone and to a cutting guide base in accordance with some embodiments.

Guide 900A differs from guide 900 in that guide 900A has a different coupling mechanism than guide 900. More particularly, guide 900A includes an extension arm 920A having projections 922A-1, 922A-2 (collectively, "projections 922A") that are configured to engage projections 714 of guide base 702 to couple guide 900A to guide base 700 as shown in FIG. 107. When guide 900A is coupled to guide base 702, slot 908A of guide 900A is aligned with slot 728 of guide base 702 such that a cutting tool, such as a bone saw or chisel, may be inserted into and through slots 908A and 728 to form a posterior chamfer on the bone.

Additional Guides (FIGS. 108-133)

FIGS. 108-113 provide various views of a cutting guide in accordance with some embodiments. Cutting guide 1000 may be placed on a flat formed on a bone, such as a talus, in some embodiments. More particularly, cutting guide 1000 includes a body 1002 having a bottom surface or side 1004 that may be placed on a flat formed on a bone. Body 1002 also includes a pair of legs 1006-1, 1006-2 (collectively, "legs 1006") each defining a first hole 1008-1, 1008-2 (collectively, "holes 1008") and a second hole 1010-1, 1010-2 (collectively, "holes 1010"). In some embodiments, holes 1008 and 1010 are formed at an angle relative to one another. For example, holes 1008 may define an axis that is perpendicular to a plane defined by surface 1004 and holes 1010 may extend through legs 1006 at an oblique angle relative to the plane defined by surface 1004.

Figure 108:
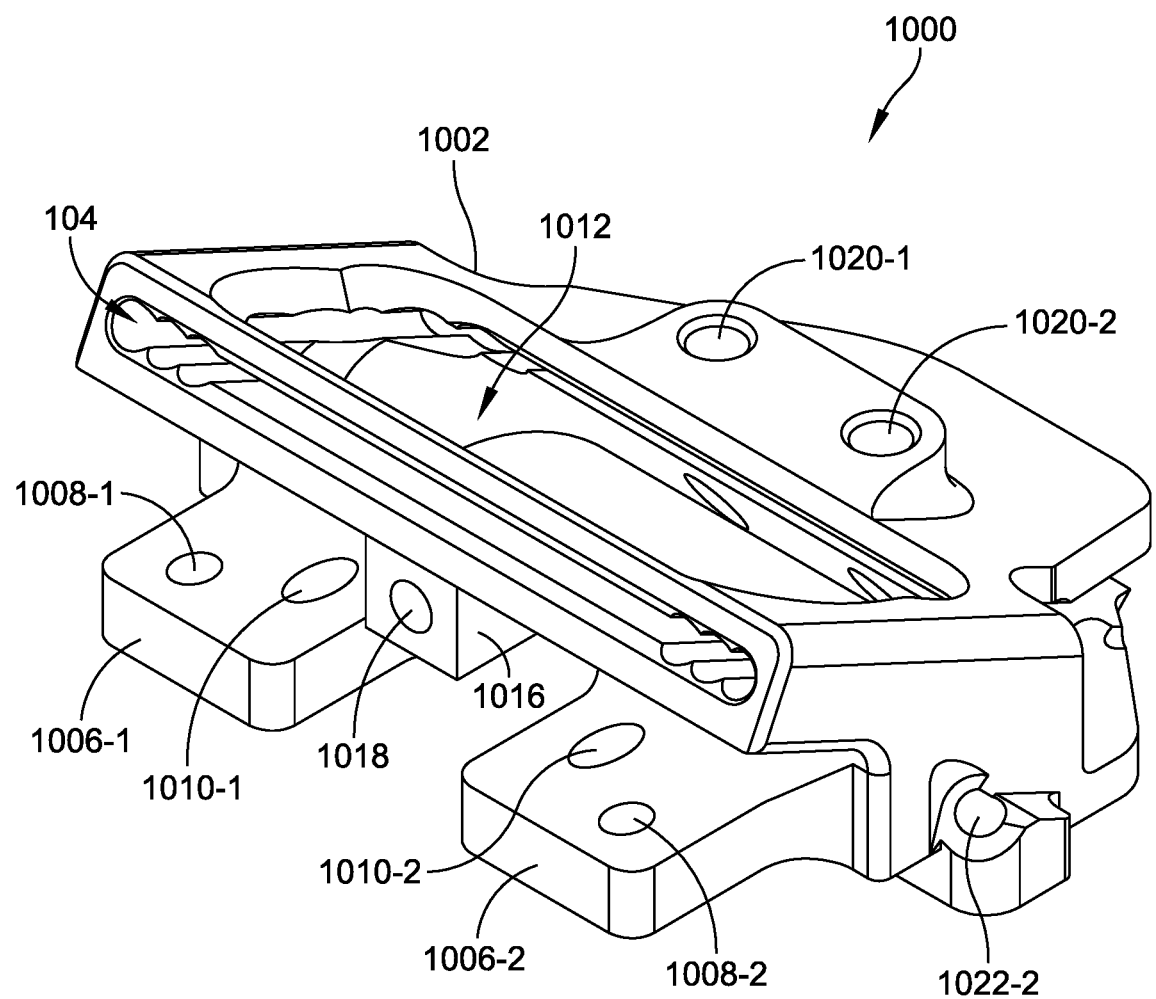
FIG. 108 is an isometric view another example of a cutting guide in accordance with some embodiments.
Figure 109:
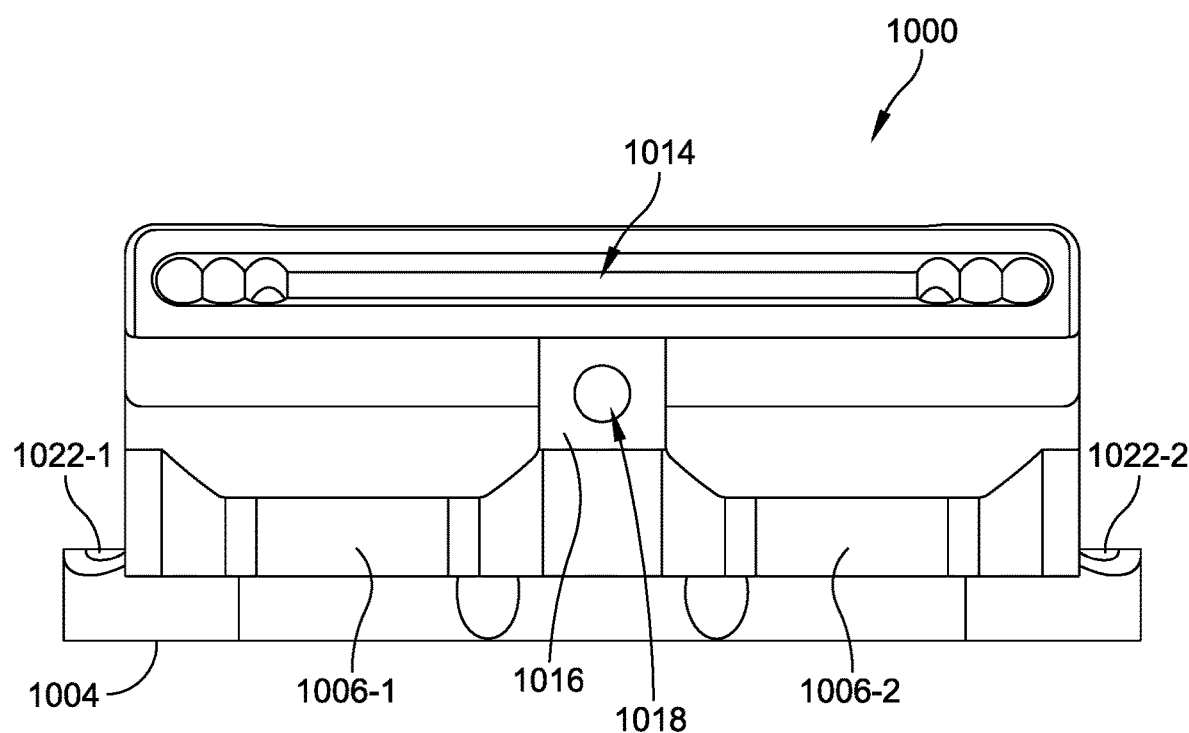
FIG. 109 is a rear side view of the cutting guide illustrated in FIG. 108 in accordance with some embodiments.
Figure 110:
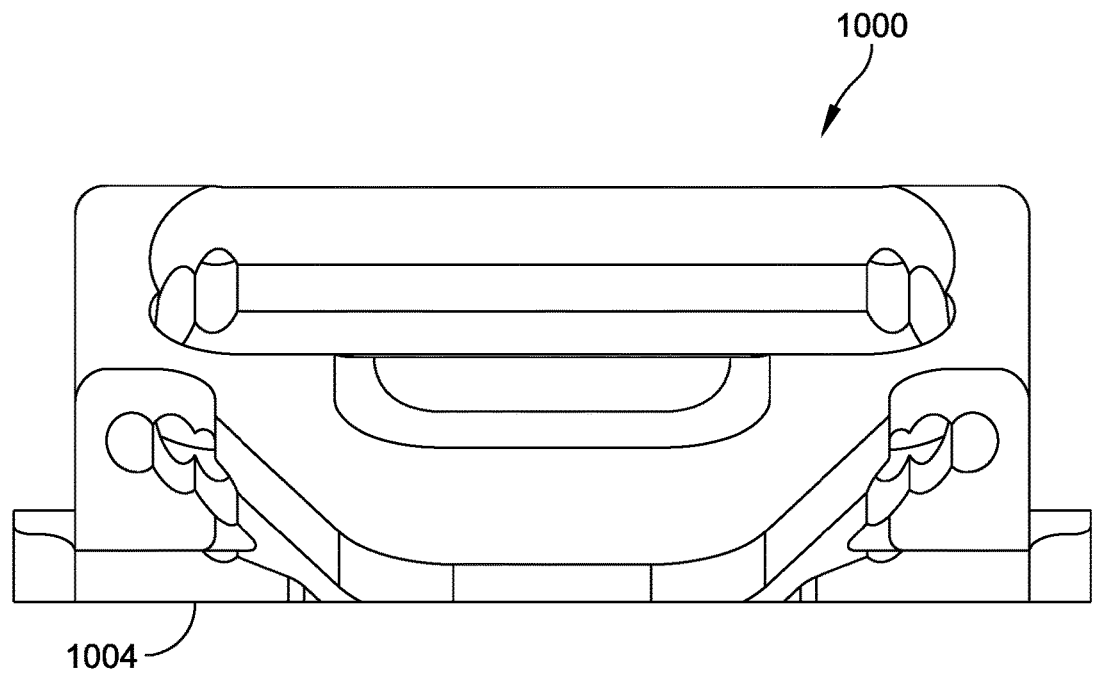
FIG. 110 is a front side view of the cutting guide illustrated in FIG. 108 in accordance with some embodiments.
Figure 111:
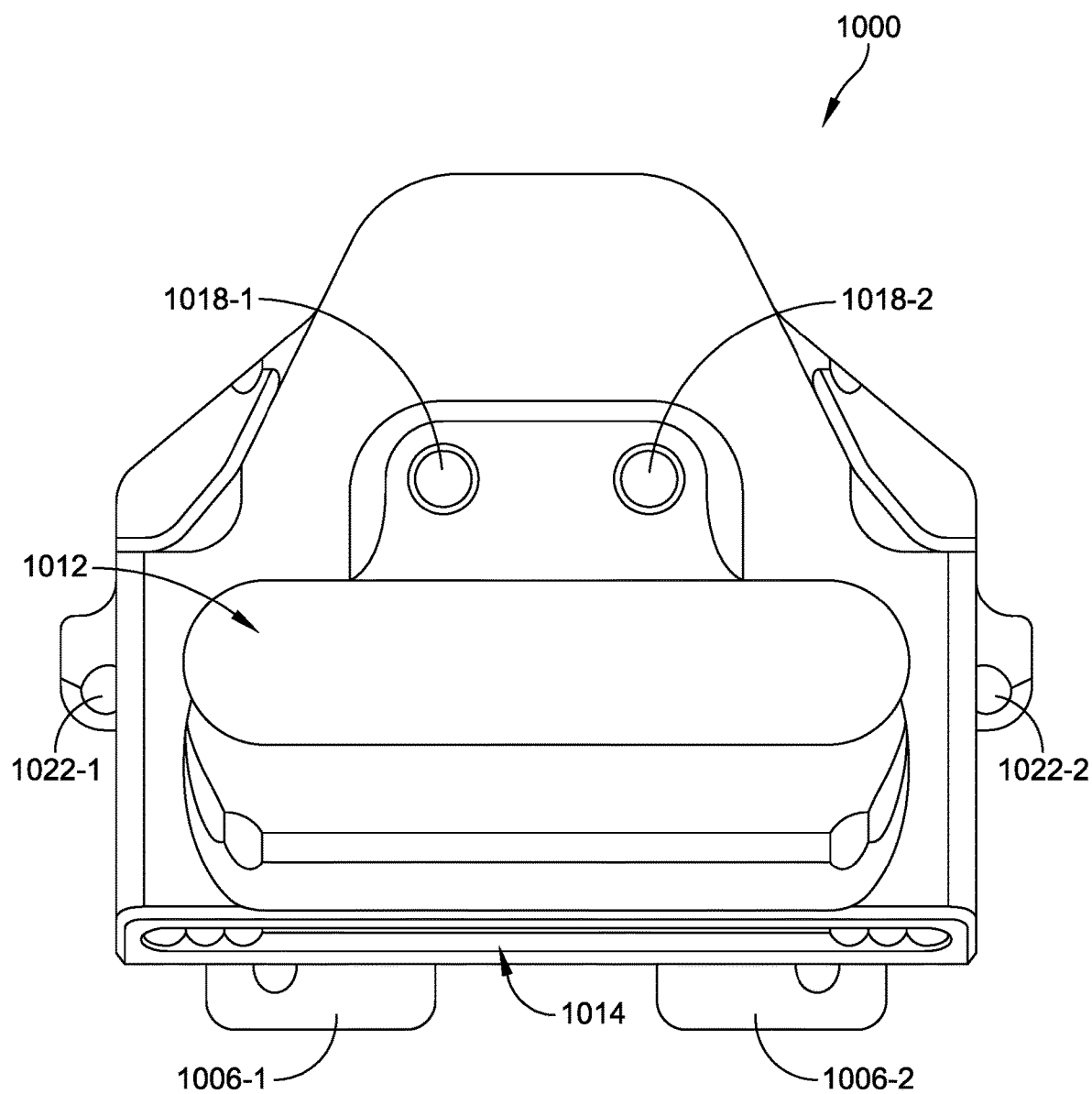
FIG. 111 is a top side view of the cutting guide illustrated in FIG. 108 in accordance with some embodiments.
Figure 112:
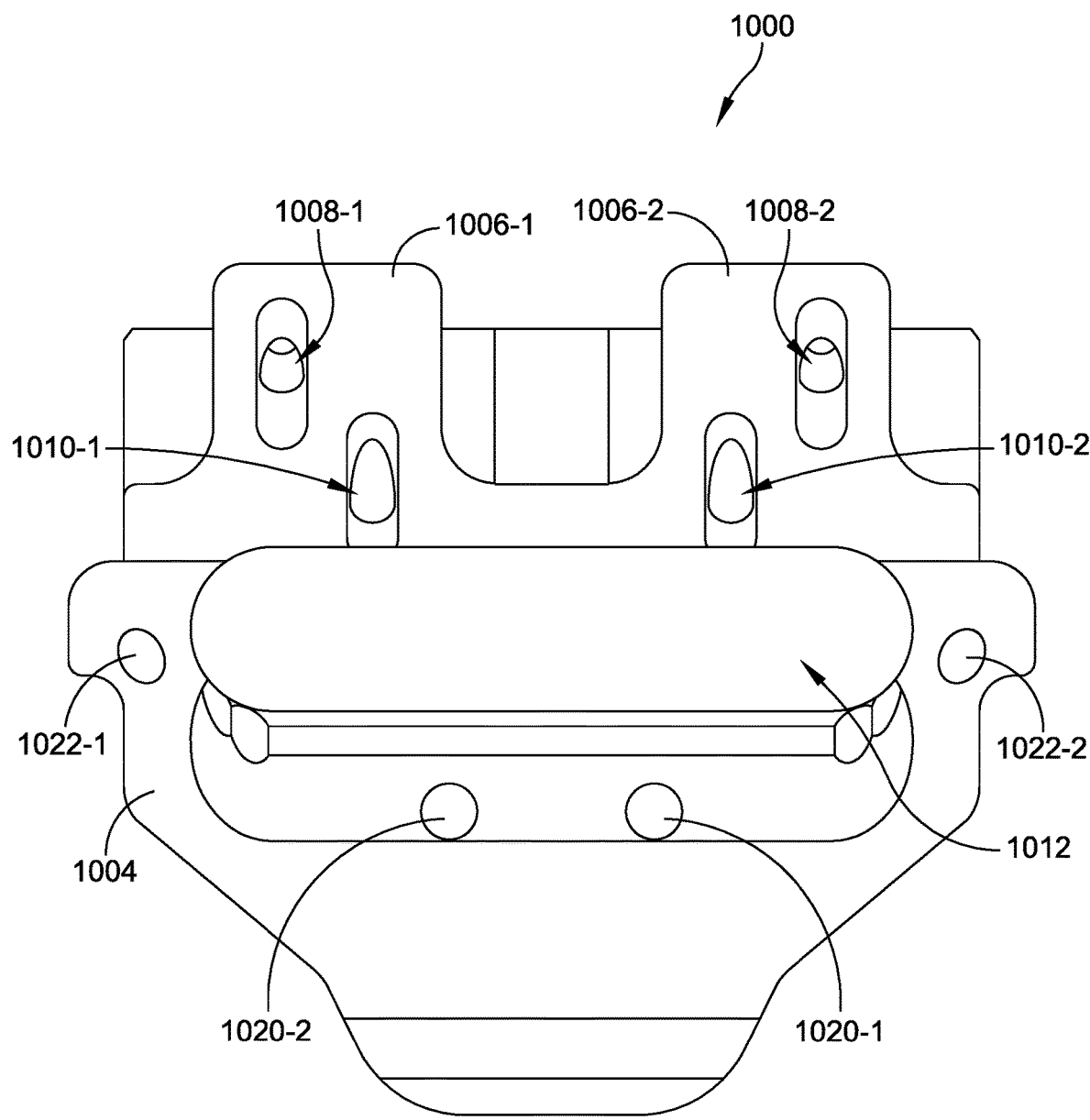
FIG. 112 is a bottom side view of the cutting guide illustrated in FIG. 108 in accordance with some embodiments.
Figure 113:
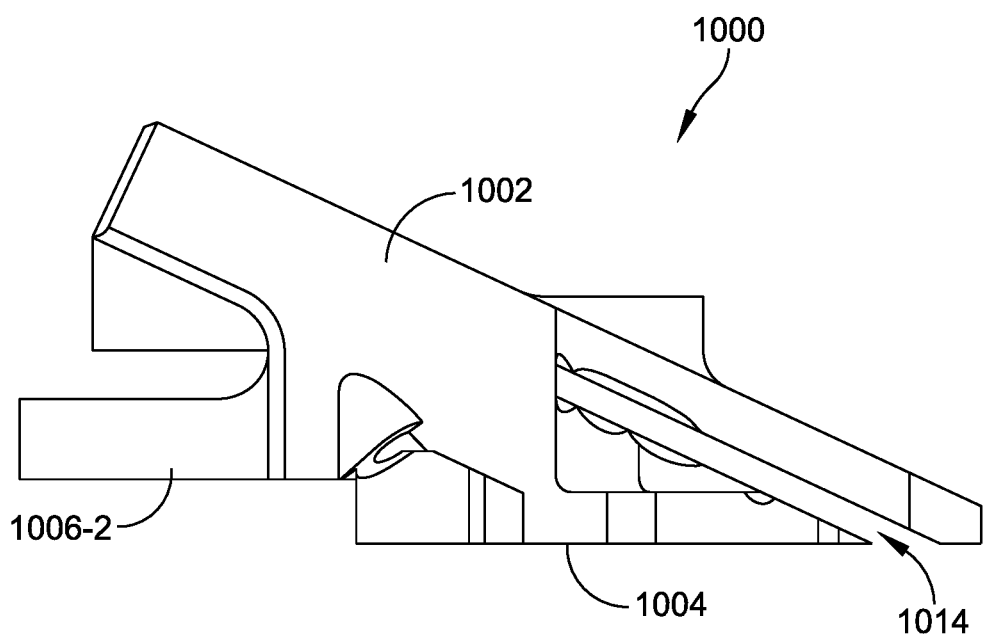
FIG. 113 is a side view of the cutting guide illustrated in FIG. 108 in accordance with some embodiments.
Figure 114:
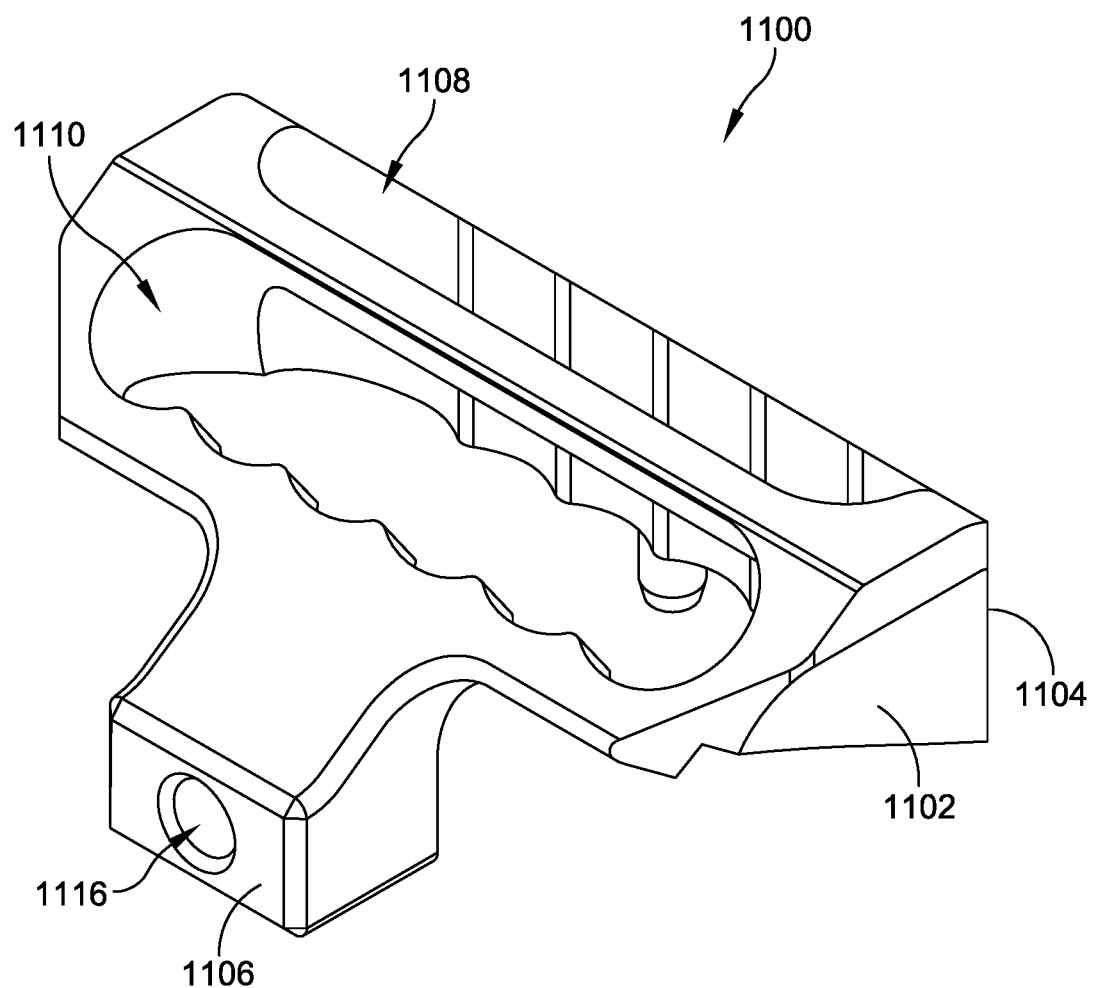
FIG. 114 is an isometric view of another example of a cutting guide that may be coupled to the cutting guide illustrated in FIGS. 108-113 in accordance with some embodiments.

Body 1002 also defines an enlarged opening 1012 and a slot 1014. Both opening 1012 and slot 1014 may extend through the entirety of body 1002. Opening 1012 is sized and configured to receive a cutting tool, such as a burr, end mill, or other rotating cutting tool, therethrough. Slot 1014 also is dimensioned to receive a cutting tool, such as a saw blade, therein. Body 1002 includes a mating portion 1016 that defines a hole 1018 as best seen in FIGS. 108 and 109. A pair of mounting holes 1020-1, 1020-2 (collectively, "mounting holes 1020") are defined adjacent to opening 1014 as best seen in FIG. 111. Lateral holes 1022-1, 1022-2

(collectively, "holes 1022" or "lateral holes 1022") may also be provided for receiving a fixation element, such as a pin or k-wire, therein to secure the cutting guide to a bone.

Figure 119:
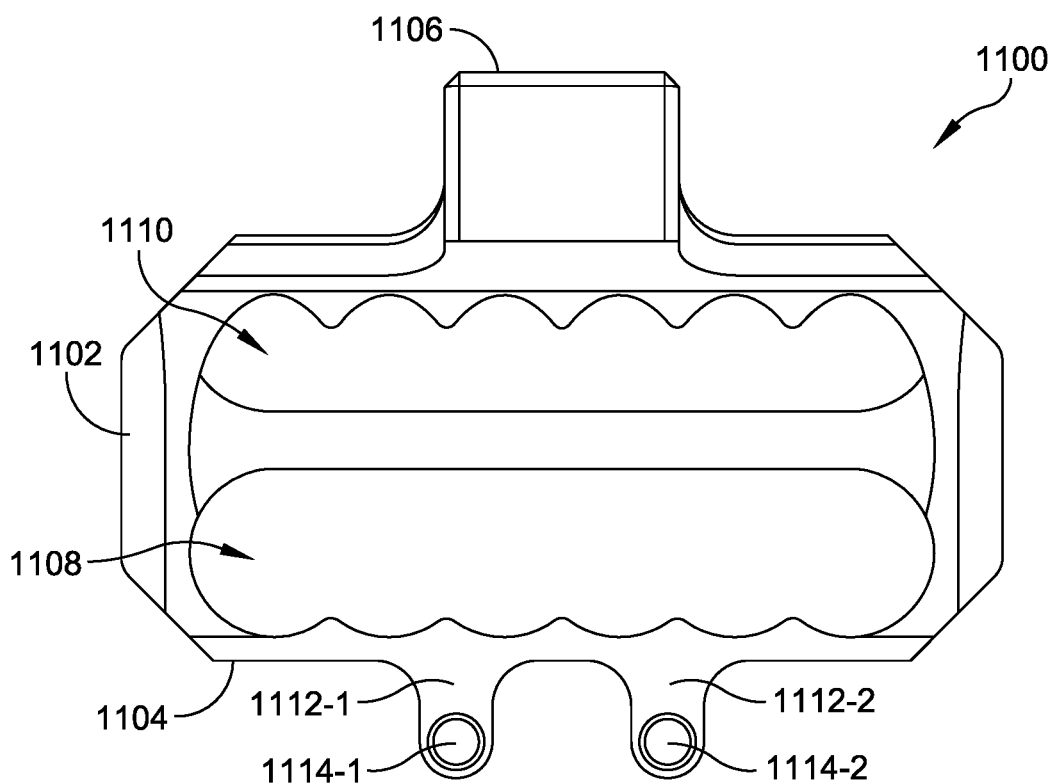
FIG. 119 is a bottom side view of the cutting guide illustrated in FIG. 114 in accordance with some embodiments.
Figure 120:
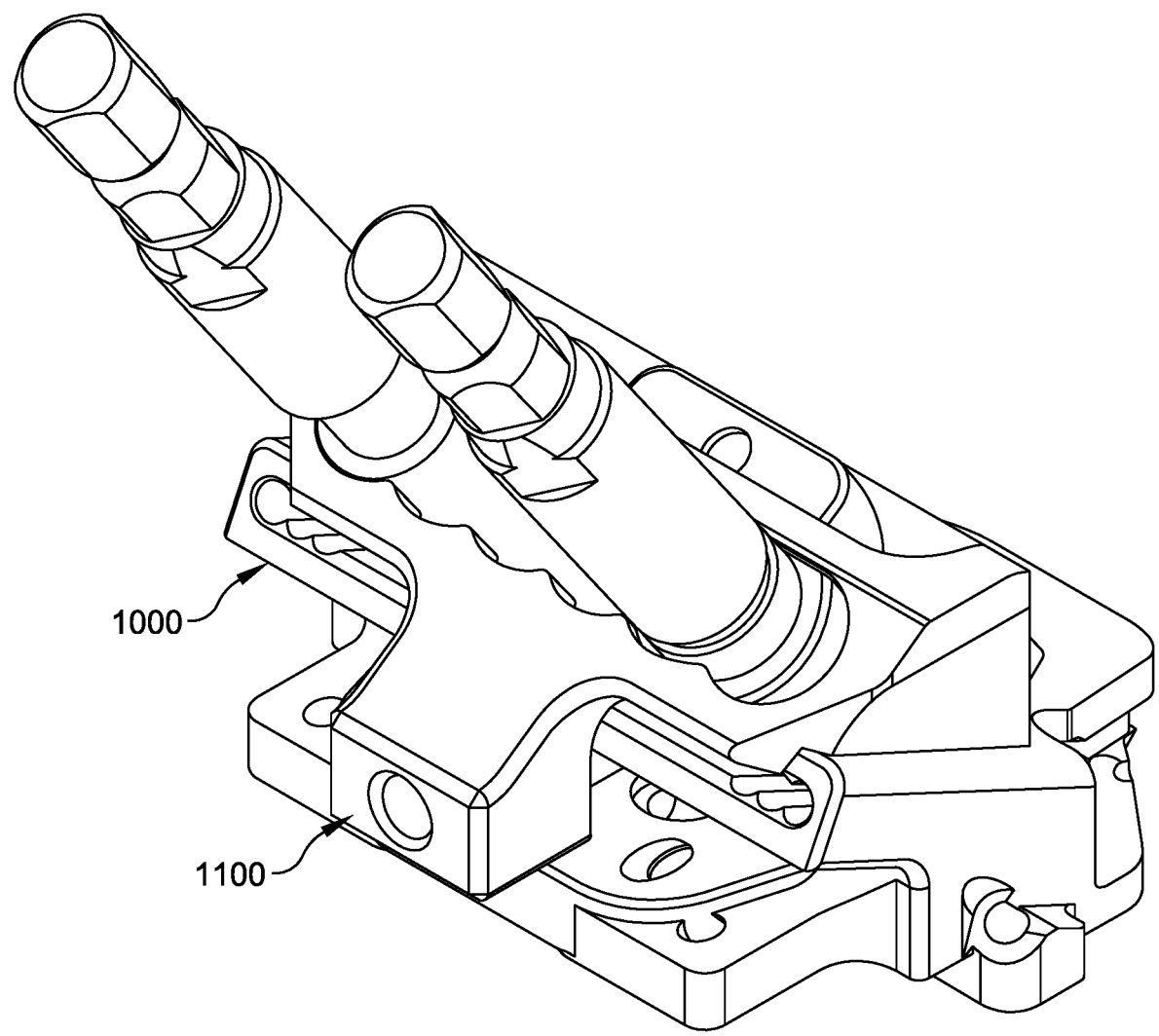
FIG. 120 is an isometric view of the guides illustrated in FIGS. 108-113 and 114-119 coupled together in accordance with some embodiments.
Figure 121:
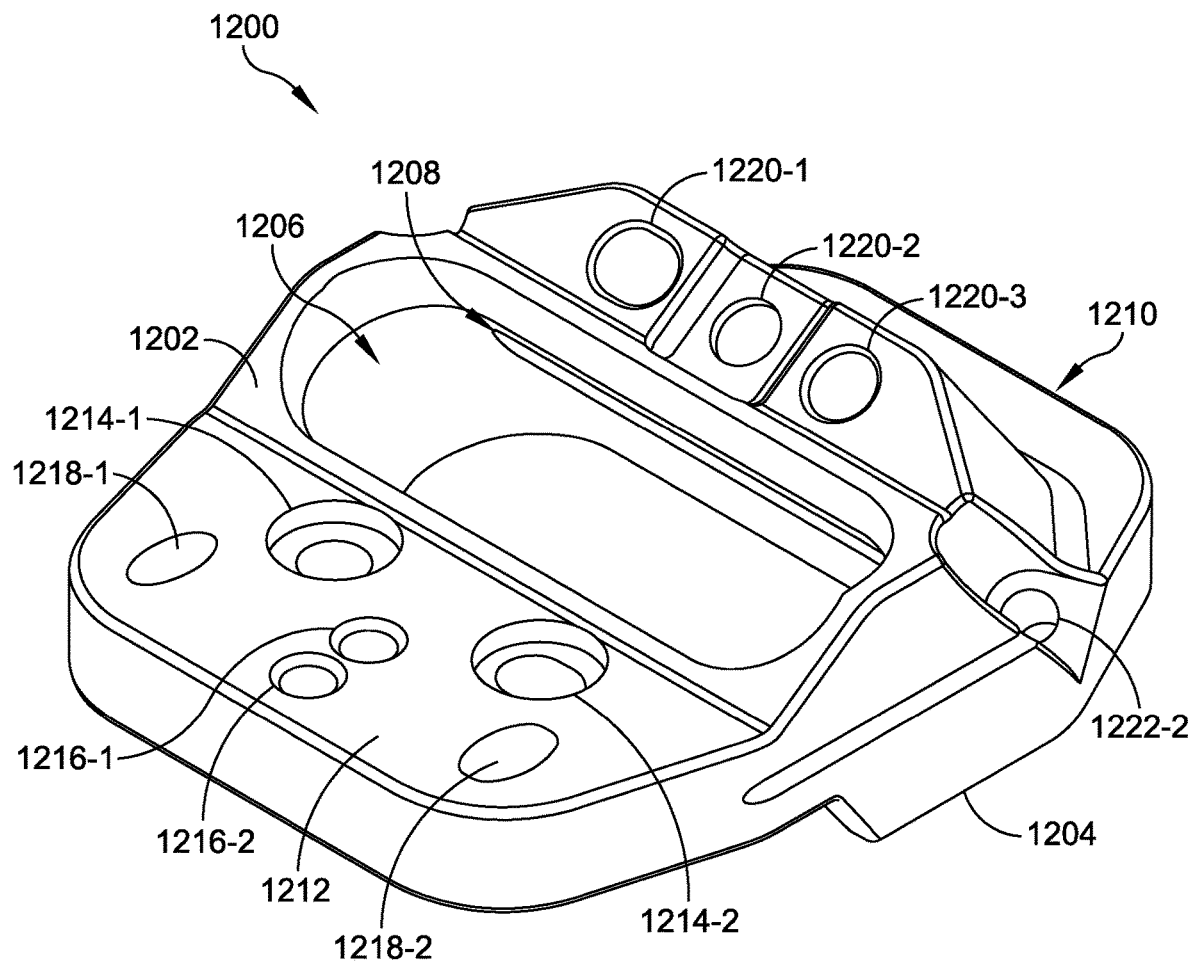
Figure 122:
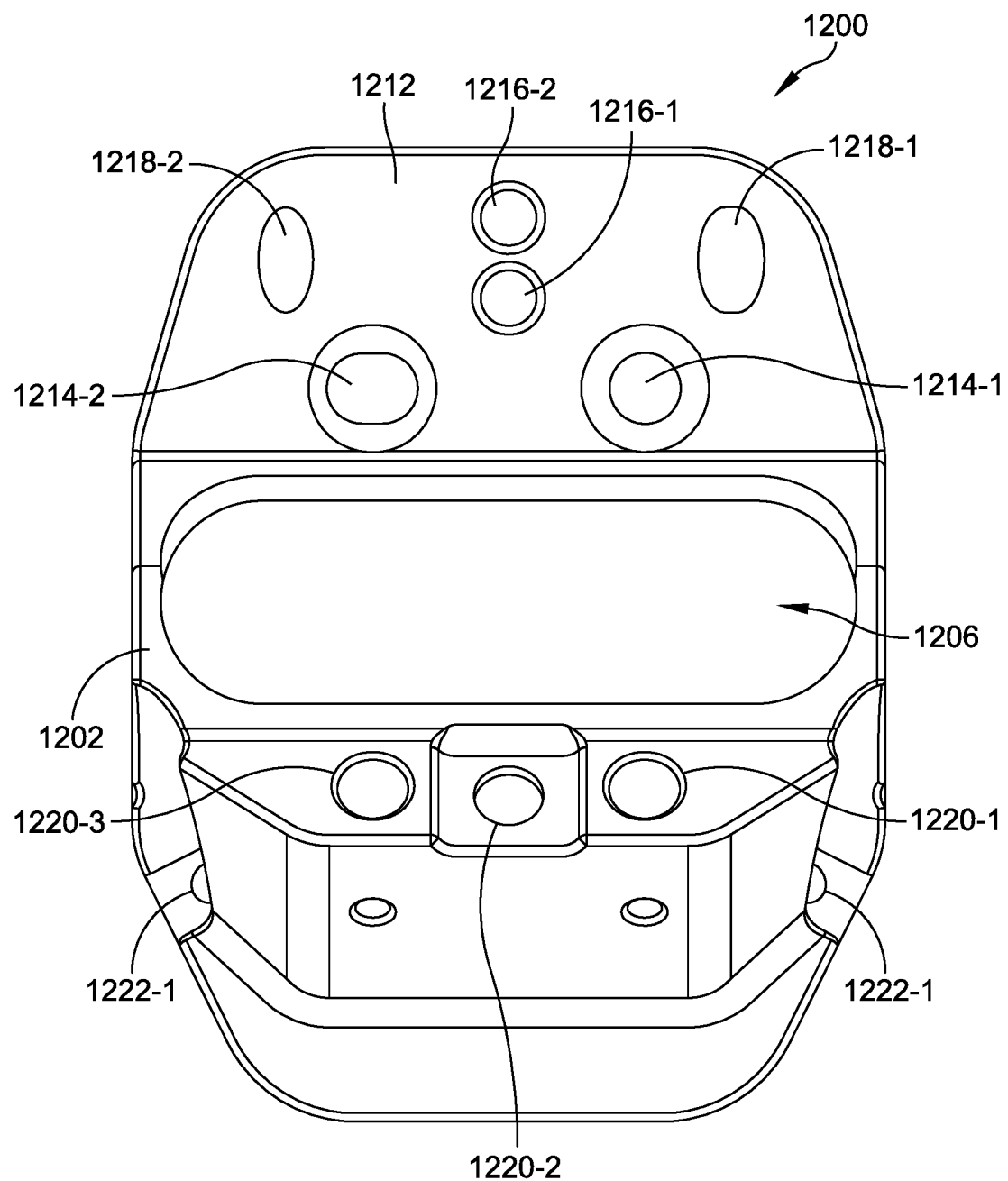
Figure 123:
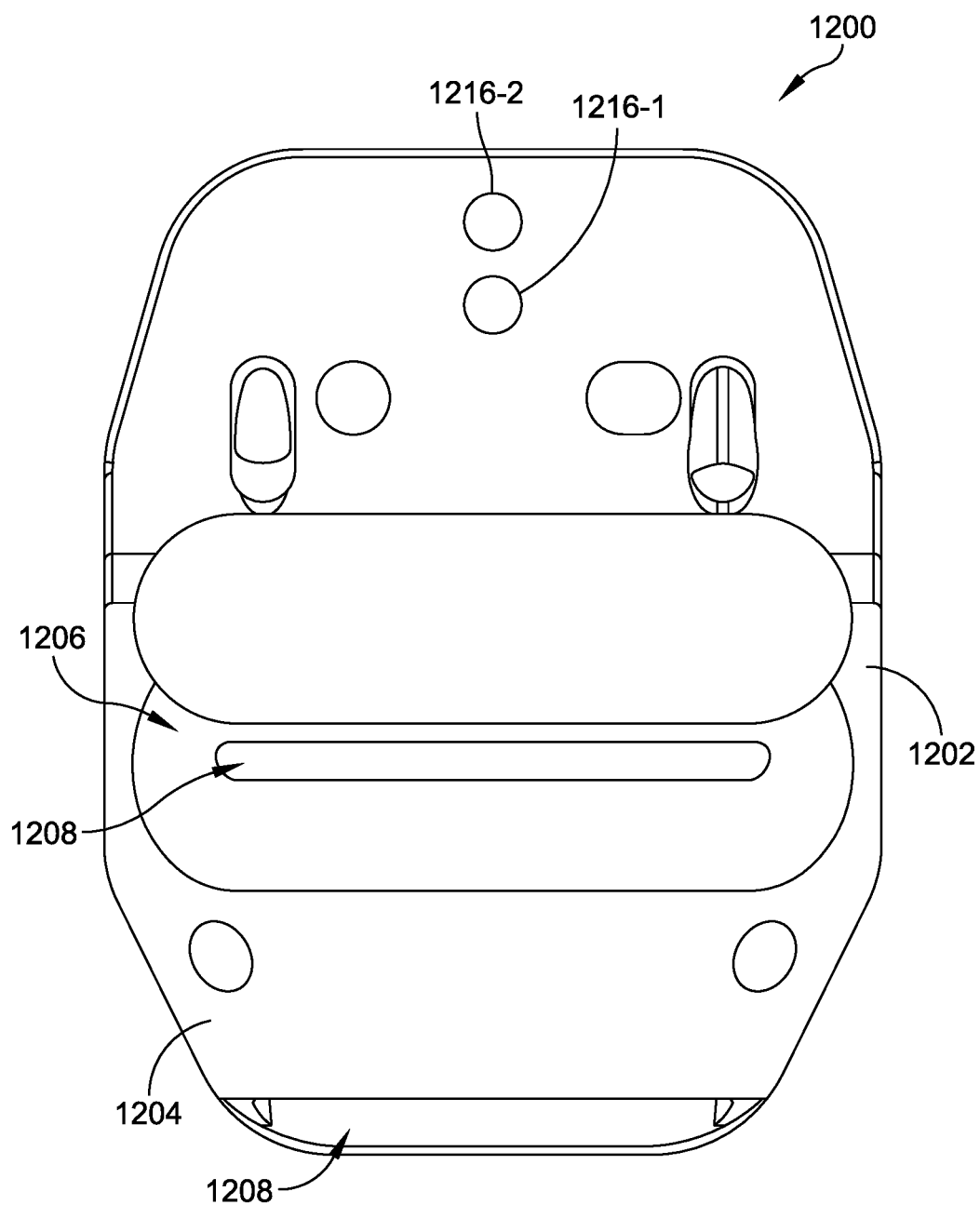
Figure 124:
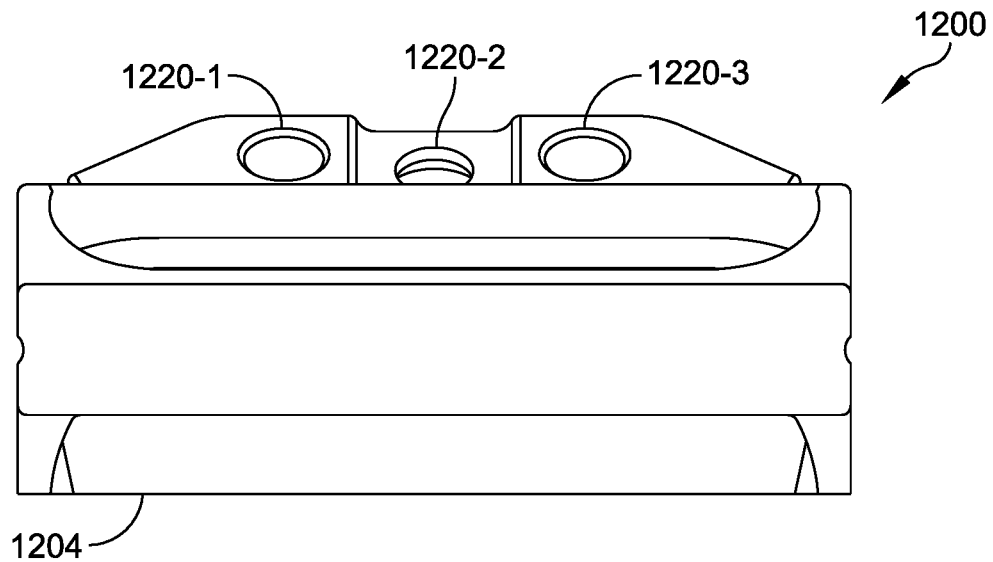
Figure 125:
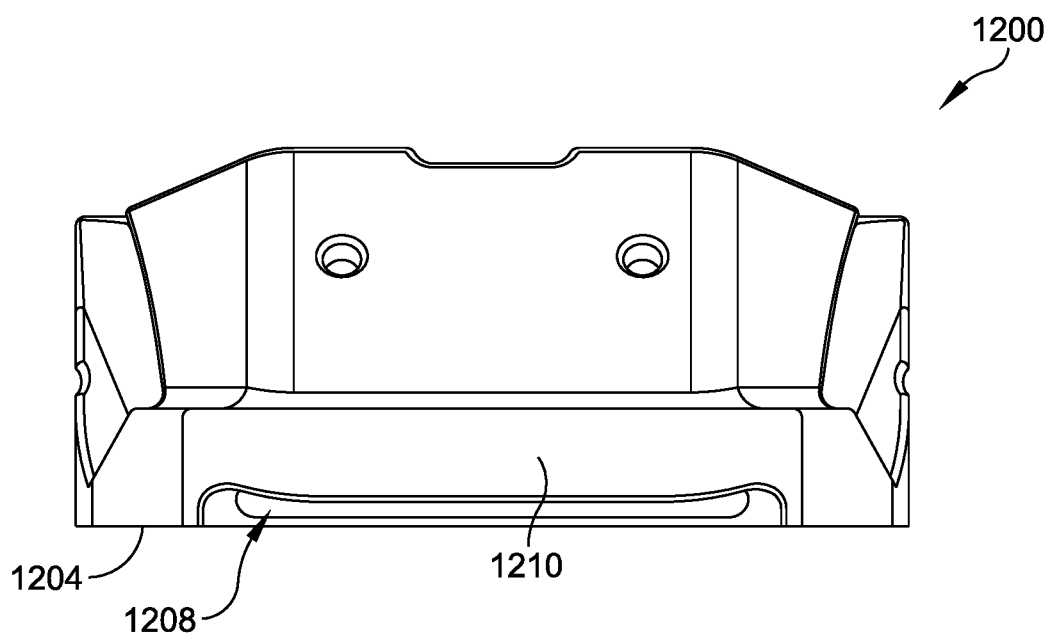
Figure 126:
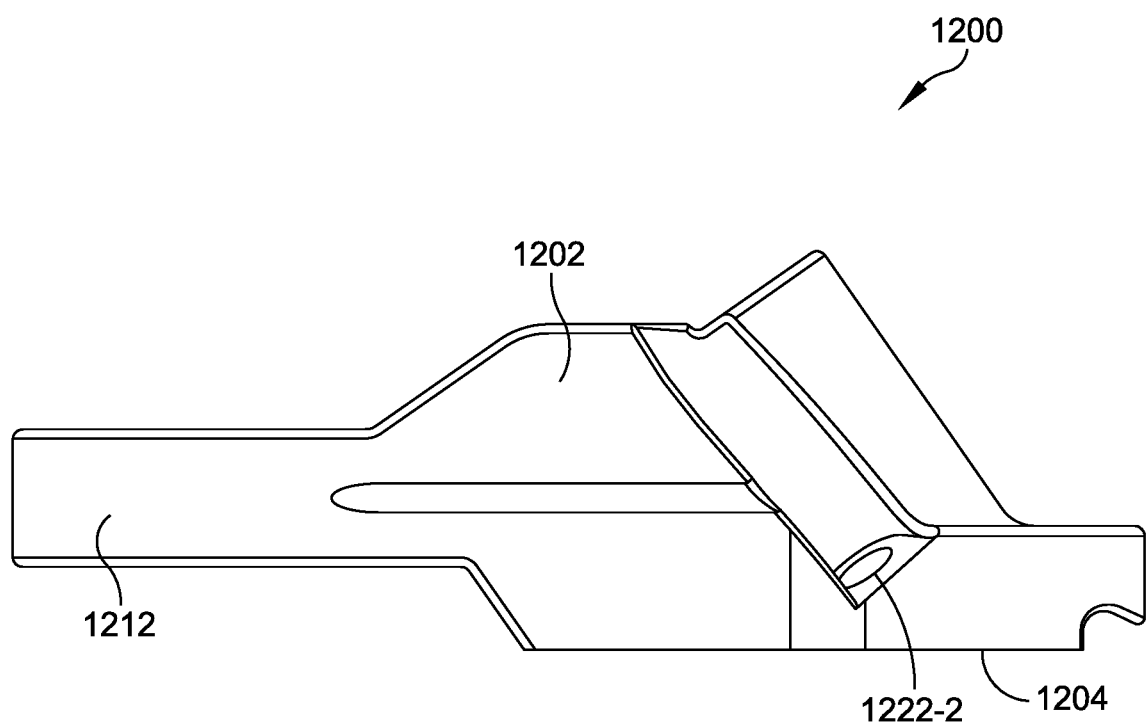
Figure 127:
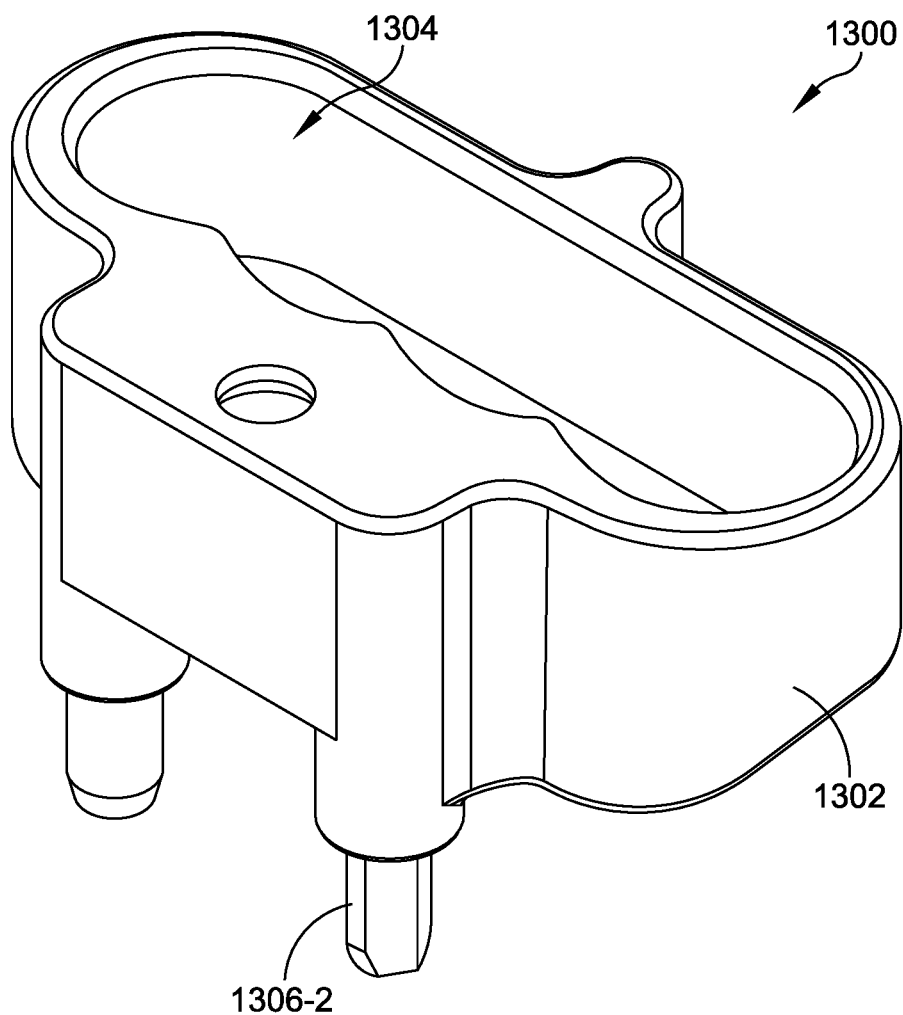
Figure 128:
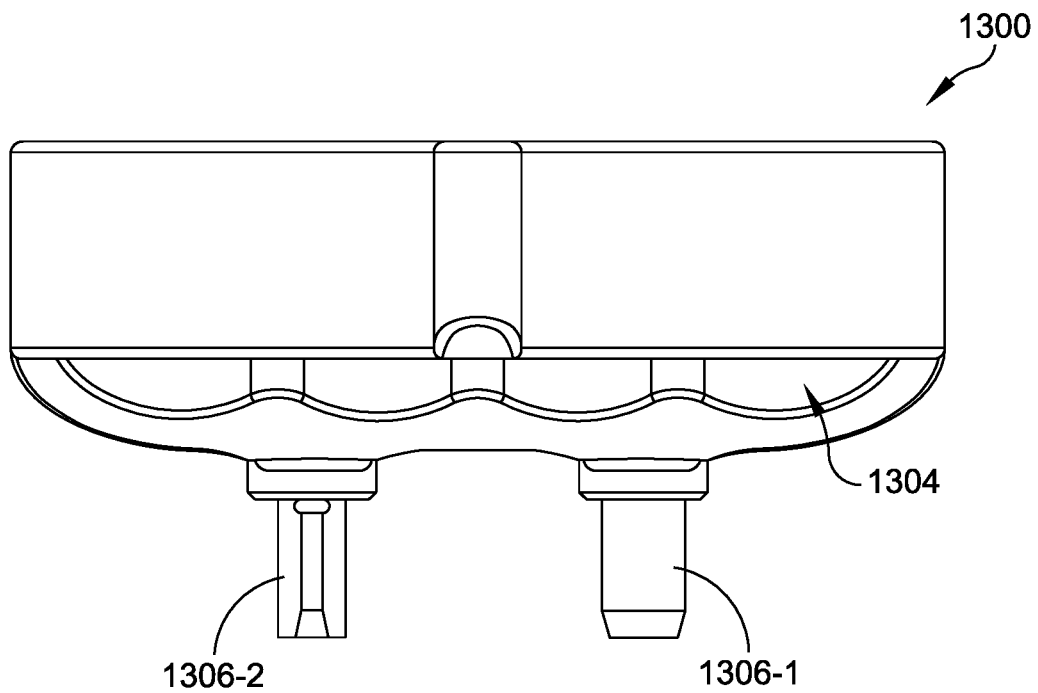
Figure 129:
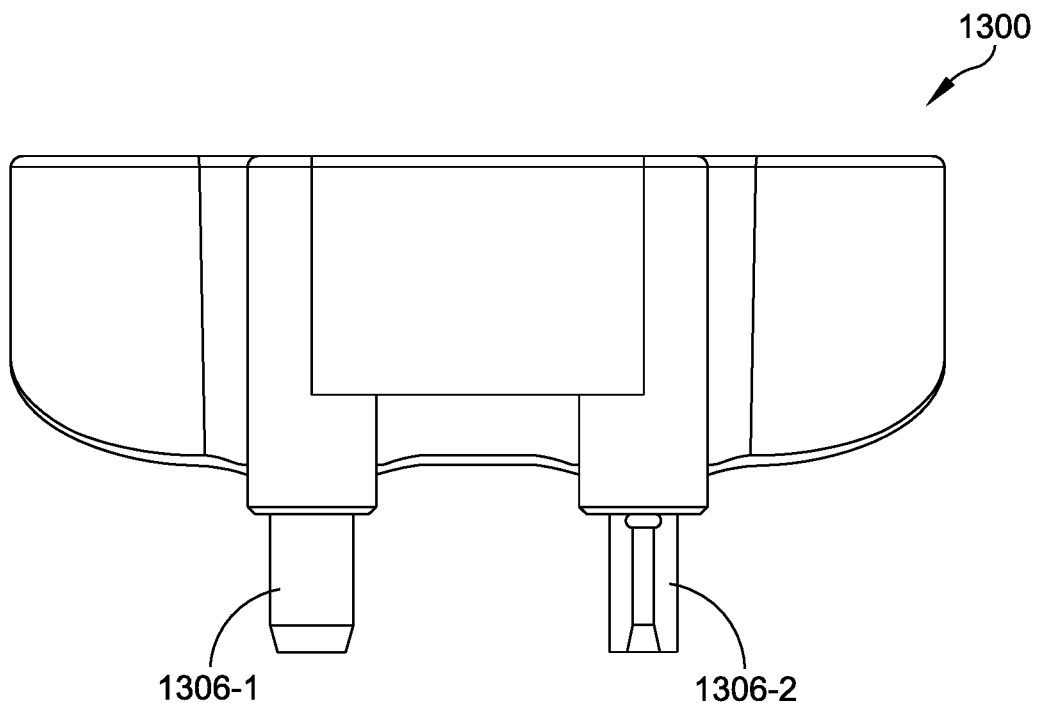
Figure 130:
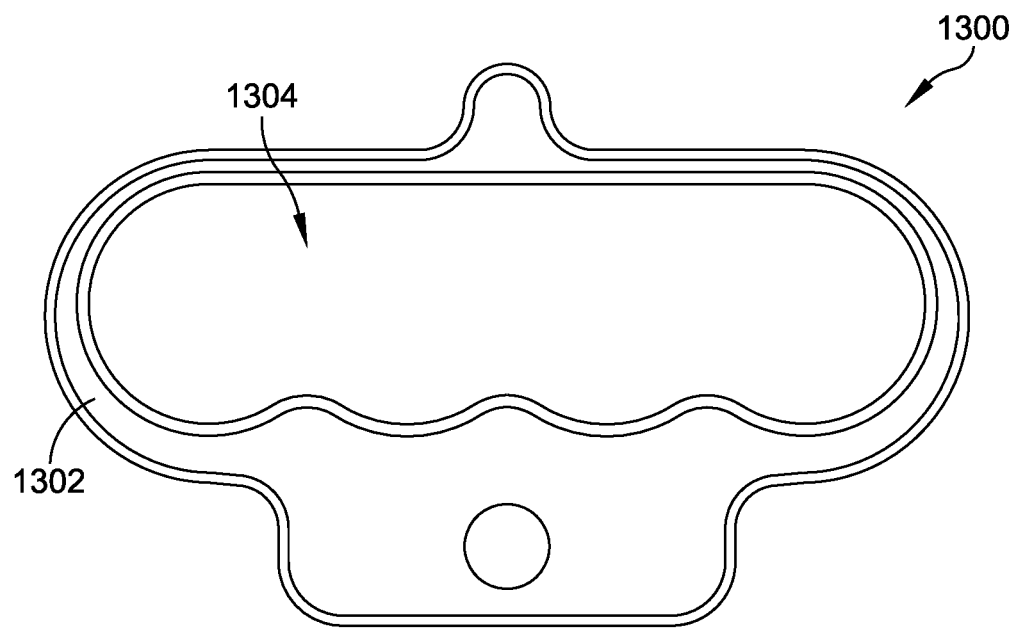
Figure 131:
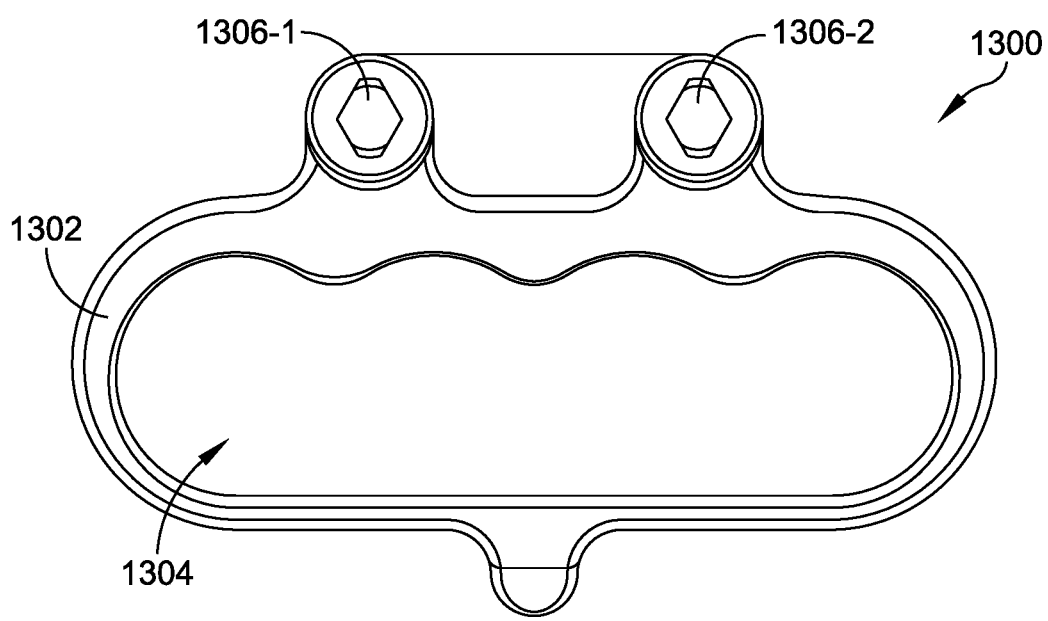
Figure 132:
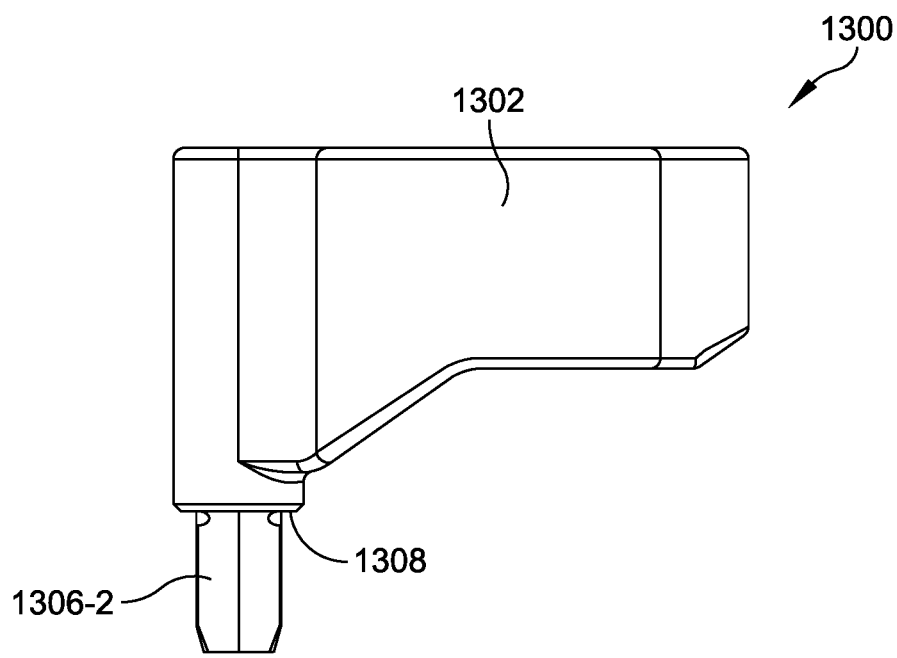
Figure 133:
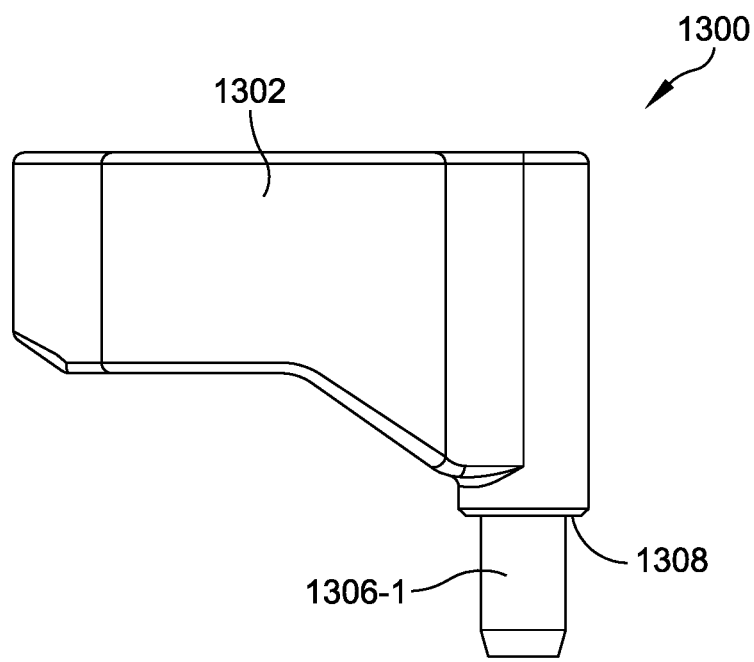

FIGS. 114-119 illustrate one example of a cutting guide 1100 that may be coupled to cutting guide 1000. Guide 1100 has a body 1102 with a leading side 1104 and a trailing side 1106 and defines a pair of enlarged openings 1108, 1110. Openings 1108, 1110 are sized and configured to align with opening 1012 defines by the body 1002 of guide 1000 when guides 1000, 1100 are coupled to one another as shown in FIG. 120.

Figure 115:
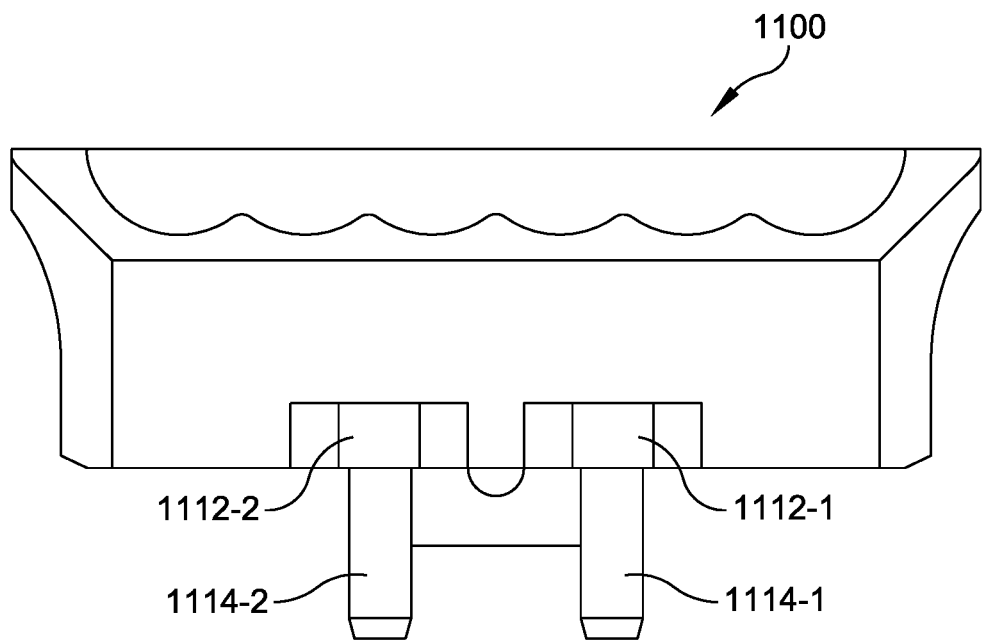
FIG. 115 is a front side view of the cutting guide illustrated in FIG. 114 in accordance with some embodiments
Figure 116:
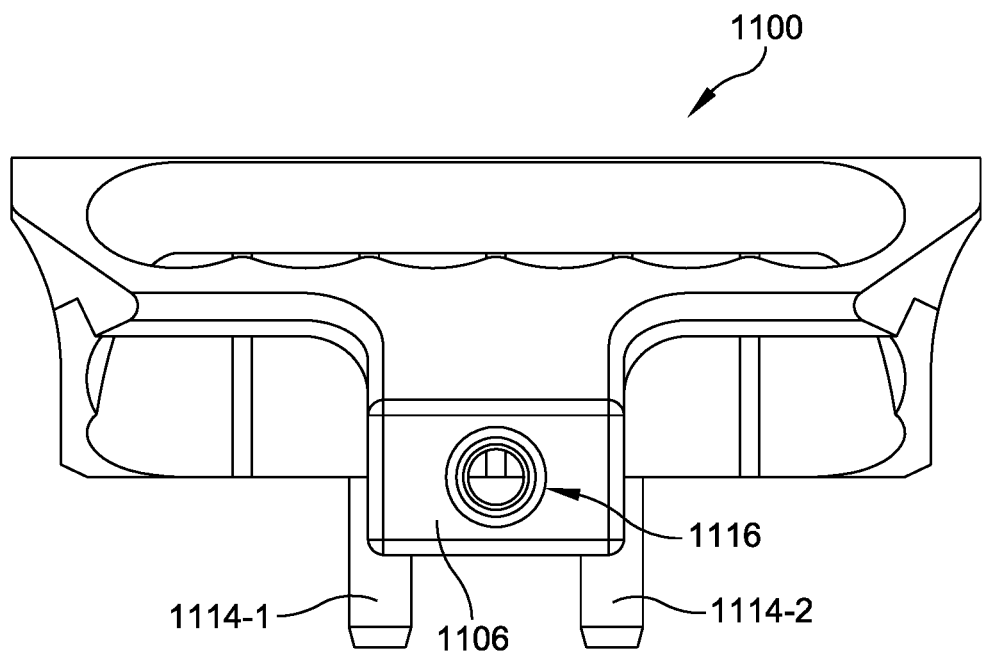
FIG. 116 is a rear side view of the cutting guide illustrated in FIG. 114 in accordance with some embodiments.
Figure 117:
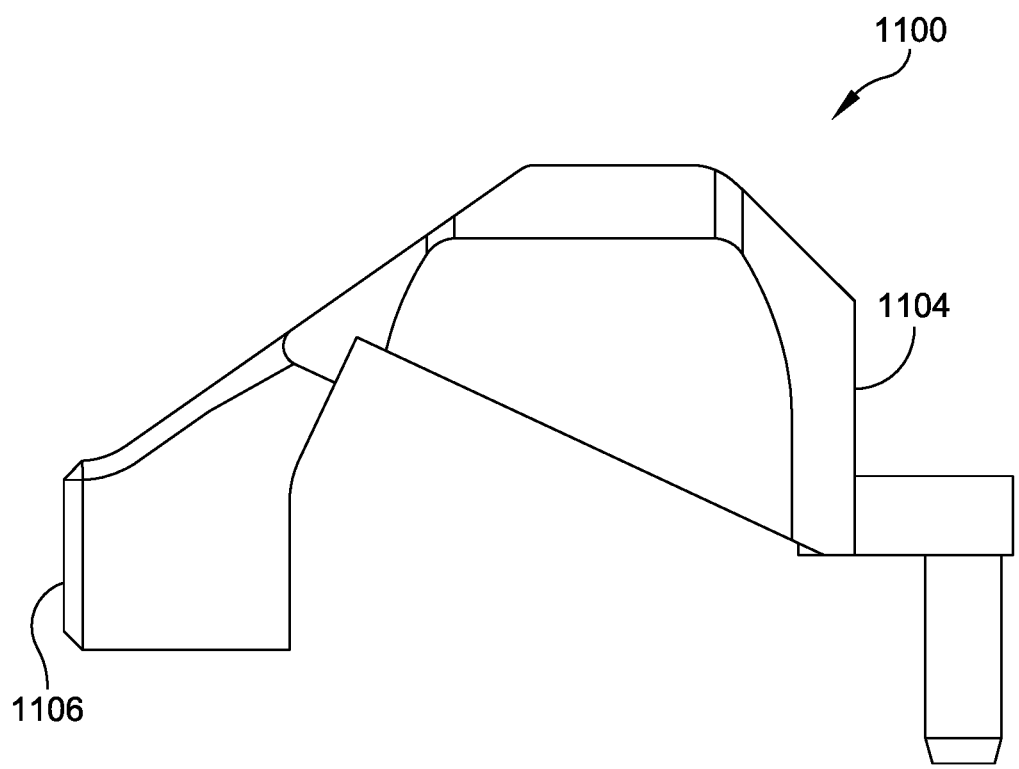
FIG. 117 is a side view of the cutting guide illustrated in FIG. 114 in accordance with some embodiments.
Figure 118:
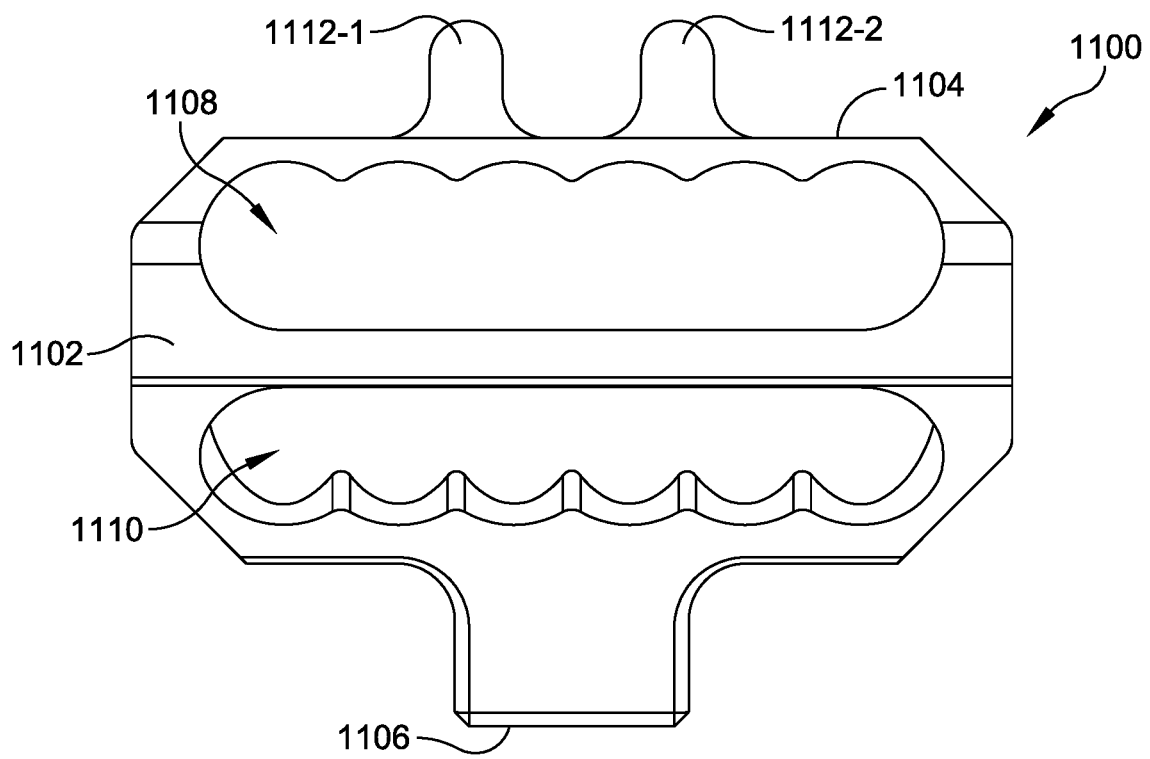
FIG. 118 is a top side view of the cutting guide illustrated in FIG. 114 in accordance with some embodiments.

Leading side 1104 may include one or more feet 1112-1, 1112-2 (collectively, "feet 1112") extending therefrom. Each foot 1112-1, 1112-2 may include a respective coupling member 1114-1, 1114-2 (collectively, "coupling members 1114"), as best seen in FIGS. 115, 116, and 119, which extend from the foot and are sized and configured to be received in a respective mounting hole 1020-1, 1020-2.

Trailing side 1106 defines a hole 1116 that is sized and configured to align with hole 1018 defined by mating portion 1016 of guide 1000. For example, hole 1116 defined by guide 1100 should align with hole 1018 when coupling members 1114 are received within mounting holes 1020 and guides 1000, 1100 are coupled together as shown in FIG. 120.

FIGS. 121-126 illustrate an example of a base component in accordance with some embodiments. Base component 1200 includes a body 1202 having a bottom side or surface 1204 that is configured to be disposed on a surface of a bone, such as a flat formed on a talus. Body 1202 defines an opening 1206 that extends through body 1202 and is sized and configured to receive a rotating cutting tool therein. A slot 1208 also is defined by body 1202 and is positioned within opening 1206 and extends toward the front side 1210.

Body 1202 also includes a rear flange 1212 that may define a first pair of holes 1214-1, 1214-2 (collectively, "holes 1214") and a second pair of holes 1216-1, 1216-2 (collectively, "holes 1216"). A third pair of holes 1218-1, 1218-2 (collectively, "holes 1218") may also be defined along flange 1212. Body 1202 may define additional holes 1220-1, 1220-2, 1220-3 (collectively, "holes 1220") adjacent to opening 1206 and lateral holes 1222-1, 1222-2 (collectively, "holes 1222" or "lateral holes 1222").

FIGS. 127-133 illustrate one example of a cutting guide 1300 that may be coupled to and used with base 1200. Guide 1300 includes a body 1302 defining an opening 1304 that is sized and configured to receive a rotating cutting tool therein. Body 1302 may include one or more legs 1306-1, 1306-2 (collectively, "legs 1306") that extend from a lower surface 1308 of body 1302. Legs 1306 are sized and configured to be received within holes 1214 and 1220 defined by base 1200. When guide 1300 is coupled to base 1200 with legs 1306 received within holes 1214 or holes 1220, the opening 1304 defined by guide 1300 aligns with opening 1206 defined by base 1200. The alignment of openings 1206 and 1304 provides guidance for a rotary cutting tool to make plunge cuts as will be understood by one of ordinary skill in the art.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A tool, comprising:
a base component having a first surface configured to engage a bone, a second surface disposed on an opposite side of the base component with respect to the first surface, and a third surface extending between the first surface and the second surface, the first surface defining a first slot that extends inwardly from a first side of the base component to a second side of the base component, the base component defining a second slot extending inwardly from the third surface and being in communication with the first slot and configured such that a chamfer is formed on the bone by passing a cutting instrument inwardly through the second slot and into the bone, and the second surface defining a passageway; and
an arm component, the arm component having a base from which a peg extends, the peg size and configured to be at least partially received within the passageway defined by the base component for coupling the arm component to the base component, wherein the arm component defines an opening sized and configured to receive a first cutting tool therein.

2. The tool of claim 1, wherein the peg of the arm component is configured to slide along a length of the passageway defined by the base component.

3. The tool of claim 1, wherein a width of the opening is greater than a width of a gap in a coupling end of the arm component that defines the opening.

4. A tool, comprising:
a base component extending from a first end to a second end, the base component defining at least one hole adjacent to the first end and including a beam disposed at the second end, the beam including at least one projection extending along its entire length and projecting perpendicular to its length; and
an arm component for coupling to the base component, the arm component including a coupling end defining a recess for receiving at least a portion of the beam and the at least one projection to couple the arm component to the base component, the arm component defining at least one hole sized and configured to receive a cutting tool therethrough.

5. The tool of claim 4, wherein the hole defines an axis that is parallel to a plane defined by the beam when the arm component is coupled to the base component.

6. The tool of claim 5, wherein the arm component defines a second hole, the second hole defining an axis that is transverse to the plane defined by the beam when the arm component is coupled to the base component.

7. The tool of claim 4, wherein the base component includes at least one stop positioned along a length of the beam.

* * * * *